US010871252B2

(12) United States Patent
Lahousse et al.

(10) Patent No.: US 10,871,252 B2
(45) Date of Patent: Dec. 22, 2020

(54) DEVICE COMPRISING A LIQUID LIPSTICK COMPOSITION IN THE FORM OF AN INVERSE EMULSION, AND A POROUS APPLICATION MEMBER

(71) Applicant: L'OREAL, Paris (FR)

(72) Inventors: Florence Lahousse, Thiais (FR); Eric Caulier, Maignelay (FR); Emilie Henin, Fresnes (FR); Roberto Cavazzuti, Paris (FR)

(73) Assignee: L'OREAL, Paris (FR)

( * ) Notice: Subject to any disclaimer, the term of this patent is extended or adjusted under 35 U.S.C. 154(b) by 22 days.

(21) Appl. No.: 15/872,347

(22) Filed: Jan. 16, 2018

(65) Prior Publication Data

US 2018/0202595 A1 Jul. 19, 2018

Related U.S. Application Data

(63) Continuation of application No. 14/779,811, filed as application No. PCT/EP2014/055977 on Mar. 25, 2014, now abandoned.

(30) Foreign Application Priority Data

Mar. 25, 2013 (FR) ...................................... 13 52649

(51) Int. Cl.
*F16L 43/00* (2006.01)
*F16L 57/00* (2006.01)
(Continued)

(52) U.S. Cl.
CPC .......... *F16L 43/008* (2013.01); *A45D 34/042* (2013.01); *A61K 8/891* (2013.01);
(Continued)

(58) Field of Classification Search
CPC .......... A61K 2800/544; A61K 2800/87; A61K 8/891; A61K 8/895; A61K 8/92;
(Continued)

(56) References Cited

U.S. PATENT DOCUMENTS 4,706,693 A 11/1987 Spector
6,238,116 B1 5/2001 Smith
(Continued)

FOREIGN PATENT DOCUMENTS

CN 1203175 12/1998
EP 0 963 751 12/1999
(Continued)

OTHER PUBLICATIONS

International Search Report dated Nov. 5, 2014 in PCT/EP14/055977 Filed Mar. 25, 2014.
(Continued)

*Primary Examiner* — Trevor Love
(74) *Attorney, Agent, or Firm* — Oblon, McClelland, Maier & Neustadt, L.L.P.

(57) ABSTRACT

An application device, including a container; a composition for making up and/or caring for the lips (P), stored in the container, which is in the form of a liquid emulsion that includes: a) at least 8% by weight, relative to the total weight of the composition, of one or more non-volatile oils; b) at least one film-forming agent selected from the group consisting of alkylcellulose, silicone resin, and a vinyl polymer comprising a carbosiloxane dendrimer-based unit; c) at least 10% by weight of water relative to the total weight of the composition; and an application member that is suitable for applying the composition which has a porous application surface with one or more open-cell or semi-open cell foams, wherein the composition has a viscosity at 25° C. of between 0.005 and 15 Pa.s.

22 Claims, 3 Drawing Sheets

(51) Int. Cl.
*A61K 8/92* (2006.01)
*A61Q 1/04* (2006.01)
*A61K 8/891* (2006.01)
*A61K 8/895* (2006.01)
*C08G 77/442* (2006.01)
*C08L 83/10* (2006.01)
*A45D 34/04* (2006.01)

(52) U.S. Cl.
CPC ............... *A61K 8/895* (2013.01); *A61K 8/92* (2013.01); *A61Q 1/04* (2013.01); *C08G 77/442* (2013.01); *C08L 83/10* (2013.01); *F16L 57/00* (2013.01); *A45D 34/045* (2013.01); *A45D 2200/055* (2013.01); *A45D 2200/1018* (2013.01); *A61K 2800/544* (2013.01); *A61K 2800/87* (2013.01)

(58) Field of Classification Search
CPC ......... A61Q 1/04; C08G 77/442; C08L 83/10; F16L 43/008; F16L 57/00; A45D 34/042; A45D 34/045; A45D 2200/055; A45D 2200/1018
See application file for complete search history.

(56) References Cited

U.S. PATENT DOCUMENTS

| 6,280,748 | B1 | 8/2001 | Morita et al. |
| 7,811,021 | B2 | 10/2010 | Gueret |
| 2002/0054783 | A1 | 5/2002 | Gueret |
| 2004/0247373 | A1 | 12/2004 | Gueret |
| 2005/0106197 | A1 | 5/2005 | Blin et al. |
| 2006/0177391 | A1 | 8/2006 | Swistowski |
| 2009/0317432 | A1 | 12/2009 | Kergosien |
| 2010/0310297 | A1 | 12/2010 | Gueret |
| 2011/0070177 | A1 | 3/2011 | Arnaud et al. |
| 2011/0100866 | A1 | 5/2011 | Gueret |
| 2011/0104222 | A1 | 5/2011 | Iida et al. |
| 2012/0263662 | A1 | 10/2012 | Iimura et al. |

FOREIGN PATENT DOCUMENTS

| EP | 1 518 535 | 3/2005 |
| FR | 2 935 268 | 3/2010 |
| JP | 10-192050 A | 7/1998 |
| JP | 2011-149017 A | 8/2011 |
| WO | WO 2012/038374 A2 | 3/2012 |
| WO | 2012/131083 | 10/2012 |

OTHER PUBLICATIONS

Chinese Office Action dated Jun. 15, 2017 in Patent Application No. 201480018509.7.
Office Action dated Mar. 19, 2018 in Japanese Patent Application No. 2016-504638, 4 pages.

DEVICE COMPRISING A LIQUID LIPSTICK COMPOSITION IN THE FORM OF AN INVERSE EMULSION, AND A POROUS APPLICATION MEMBER

The present application is a continuation of U.S. application Ser. No. 14/779,811 filed Sep. 24, 2015, pending, which is a National Stage of PCT/EP2014/055977 filed Mar. 25, 2014 and claims the benefit of FR 1352649 filed Mar. 25, 2013.

The subject of the present invention is an application device comprising a container, a composition in emulsion form intended to be applied to the lips, and an application member which has a porous application surface.

The present invention relates to the field of making up and/or caring for the lips using fluid compositions.

The development of fluid compositions dedicated to making up and/or caring for the lips, such as liquid lipsticks, which are stable and endowed with satisfactory properties in terms of application (glidance on application, ease of spreading and fineness of the deposit), but also in terms of the makeup effect of the deposit on the lips, for instance the coverage and the absence of migration of the deposit, preferably without becoming tacky, is an ongoing objective.

Generally, the formulations corresponding to liquid galenical formulations conventionally comprise oils, which in particular provide gloss, optionally waxes for structuring the compositions, fillers, in particular for thickening the composition, film-forming polymers, and colorants.

In the more particular case of compositions providing coverage, it is important for the latter to be easy to apply to the lips, precisely and as an even layer. In addition, the deposit is not expected to migrate, which would result in the outline of the lips being made imprecise.

With the conventional lipstick compositions of this type, it is noted that the deposit is relatively thick, thereby giving it a more or less tacky nature, in particular induced by the use of these oils and of the polymers present. This nature is in particular reflected by a phenomenon of the made up lips sticking to one another, which is therefore unpleasant in terms of comfort for the user.

Another difficulty encountered with liquid lipsticks lies in the fact that the composition must be sufficiently fluid to be easily applied, but not too fluid, so as to avoid losing stability of the composition (pigment sedimentation) and losing ease of application (running and/or migration of the composition to the wrinkles and fine lines of the area around the lips).

Compositions which at the same time provide very good coverage of the lips, as a precise deposit, which do not migrate, and for which the tacky nature has been virtually dispensed with, are therefore sought.

These objectives are achieved by the present invention, the subject of which is thus an application device comprising:
 a container;
 a liquid composition, stored in the container, which is in the form of an emulsion and which comprises:
  a) at least 8% by weight, relative to the total weight of the composition, of one or more non-volatile oils;
  b) at least one film-forming agent;
  c) at least 10% by weight of water relative to the total weight of the composition;
 an application member which has a porous application surface.

The present invention also relates to a process for making up and/or caring for the lips, in which the composition of the abovementioned device is applied to the lips by means of the application member.

BRIEF DESCRIPTION OF THE SEVERAL VIEWS OF THE DRAWINGS

Application devices that are particularly suited to this composition will be described with reference to the appended drawings, in which.

Figure 1:
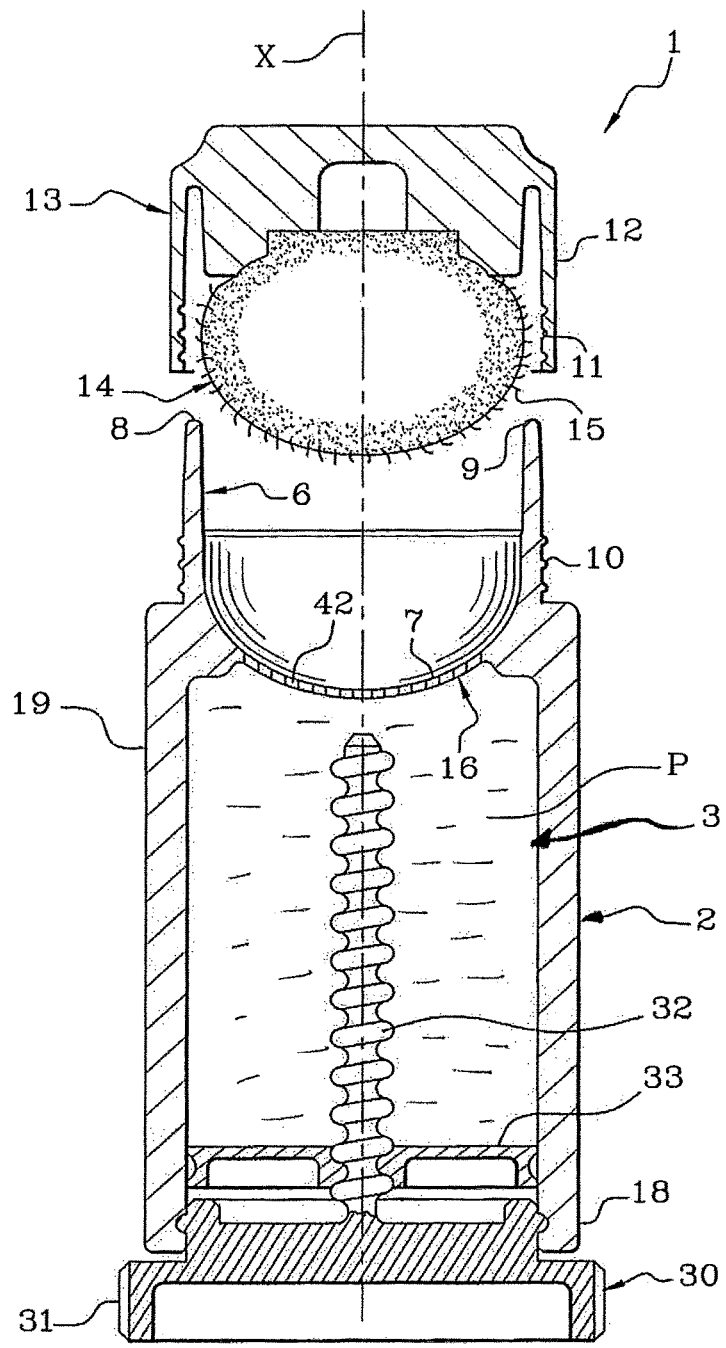
FIG. 1 is a sectional view of an application device according to a first embodiment.

Particularly advantageously, the deposit made on the lips by means of the present invention makes it possible to obtain an extremely thin deposit, in particular of about 5 µm to 30 µm, preferably of less than 20 µm, measured before drying (wet deposit).

This film is so thin that it has the advantage of being virtually imperceptible by the user.

In addition, and this represents a very desired advantage, this deposit is not tacky. It also does not provide a feeling of dryness on the lips.

Furthermore, by virtue of the device used, the deposit can be obtained in a single pass, precisely, with neither running nor migration on application. These qualities of absence of migration of the composition are found over time.

It should be noted that, in the remainder of the description, unless otherwise indicated, the limits indicated for a range are included in said range.

The expressions "at least one" and "several" are used without distinction.

Composition

As indicated previously, the composition according to the invention is liquid and is in the form of an emulsion.

The term "liquid" is intended to mean a fluid texture, the viscosity of which at 25° C. is more particularly between 0.005 and 15 Pa·s, preferably between 0.01 and 10 Pa·s and even more advantageously between 0.05 and 8 Pa·s.

Preferably, the viscosity at 25° C. of a composition according to the invention is between 0.1 and 6 Pa·s.

Protocol for Measuring the Viscosity:

The viscosity measurement is generally performed at 25° C., using a Rheomat RM180 viscometer equipped with a No. 2 or 3 spindle, the measurement being performed after 10 minutes of rotation of the spindle in the composition (after which time stabilization of the viscosity and of the spin speed of the spindle are observed), at a shear rate of 200 rpm.

The composition may be in the form of a direct (oil-in-water) or inverse (water-in-oil) emulsion.

According to one preferred embodiment of the invention, the composition is in the form of an inverse (water-in-oil) emulsion.

Whatever the direction of the emulsion, the composition according to the invention comprises at least 10% by weight of water and preferably from 20% to 60% by weight relative to the total weight of the composition.

It also comprises at least 8% by weight, relative to the total weight of the composition, of one or more non-volatile oils.

Preferably, the content of non-volatile oil(s) is between 10% and 30% by weight relative to the weight of the composition.

Non-Volatile Oils

The non-volatile oil(s) is (are) more particularly chosen from non-volatile silicone oils, which may or may not be phenylated, non-volatile fluoro oils, polar or non-polar non-volatile hydrocarbon-based oils, or mixtures thereof.

The term "oil" is intended to mean a non aqueous compound, non miscible in water, liquid, at 25° C. and atmospheric pressure (760 mmHg; $1.013.10^5$ Pa).

The term "non-volatile" is intended to mean an oil of which the vapour pressure at 25° C. and atmospheric pressure is non-zero and is less than 0.02 mmHg (2.66 Pa) and better still less than $10^{-3}$ mmHg (0.13 Pa).

Silicone Oils

The term "silicone oil" is intended to mean an oil containing at least one silicon atom, and in particular containing Si—O groups.

Non-Volatile Non-Phenylated Silicone Oils

The expression "non-phenylated silicone oil" denotes a silicone oil which does not have a phenyl substituent.

Representative examples of these non-volatile non-phenylated silicone oils which may be mentioned include polydimethylsiloxanes; alkyl dimethicones; vinylmethyl methicones; and also silicones modified with aliphatic groups and/or with functional groups such as hydroxyl, thiol and/or amine groups.

It should be noted that "dimethicone" (INCI name) corresponds to a polydimethylsiloxane (chemical name).

The non-volatile non-phenylated silicone oil is preferably chosen from non-volatile dimethicone oils.

In particular, these oils can be chosen from the following non-volatile oils:

polydimethylsiloxanes (PDMSs),

PDMSs comprising aliphatic groups, in particular alkyl or alkoxy groups, which are pendent and/or at the end of the silicone chain, these groups each comprising from 2 to 24 carbon atoms. By way of example, mention may be made of the cetyl dimethicone sold under the commercial reference Abil Wax 9801 from Evonik Goldschmidt, PDMSs comprising aliphatic groups, or functional groups such as hydroxyl, thiol and/or amine groups, polyalkylmethylsiloxanes substituted with functional groups such as hydroxyl, thiol and/or amine groups, polysiloxanes modified with fatty acids, fatty alcohols or polyoxyalkylenes, and mixtures thereof.

Preferably, these non-volatile non-phenylated silicone oils are chosen from polydimethylsiloxanes; alkyl dimethicones and also PDMSs comprising aliphatic groups, in particular $C_2$-$C_{24}$ alkyl groups, and/or functional groups such as hydroxyl, thiol and/or amine groups.

The non-phenylated silicone oil may be chosen in particular from silicones of formula (I):

$$X-\underset{R_2}{\overset{R_1}{Si}}-O-\left[\underset{R_4}{\overset{R_3}{Si}}-O\right]_n-\left[\underset{R_6}{\overset{R_5}{Si}}-O\right]_p-\underset{R_2}{\overset{R_1}{Si}}-X \quad (I)$$

in which:

$R_1$, $R_2$, $R_5$ and $R_6$ are, together or separately, an alkyl radical containing 1 to 6 carbon atoms, $R_3$ and $R_4$ are, together or separately, an alkyl radical containing from 1 to 6 carbon atoms, a vinyl radical, an amine radical or a hydroxyl radical, X is an alkyl radical containing from 1 to 6 carbon atoms, a hydroxyl radical or an amine radical, n and p are integers chosen so as to have a fluid compound, in particular of which the viscosity at 25° C. is between 9 centistokes (cSt) ($9 \times 10^{-6}$ $m^2/s$) and 800 000 cSt.

As non-volatile non-phenylated silicon oils which can be used according to the invention, mention may be made of those for which:

the substituents $R_1$ to $R_6$ and X represent a methyl group, and p and n are such that the viscosity is 500 000 cSt, for example the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning, the substituents $R_1$ to $R_6$ and X represent a methyl group, and p and n are such that the viscosity is 60 000 cSt, for example the product sold under the name Dow Corning 200 Fluid 60 000 CS by the company Dow Corning, and the product sold under the name Wacker Belsil DM 60 000 by the company Wacker, the substituents $R_1$ to $R_6$ and X represent a methyl group, and p and n are such that the viscosity is 100 cSt or 350 cSt, for example the products sold respectively under the names Belsil DM100 and Dow Corning 200 Fluid 350 CS by the company Dow Corning, the substituents $R_1$ to $R_6$ represent a methyl group, the group X represents a hydroxyl group, and n and p are such that the viscosity is 700 cSt, for example the product sold under the name Baysilone Fluid T0.7 by the company Momentive.

Non-Volatile Phenylated Silicone Oils

The expression "phenylated silicone oil" or "phenyl silicone oil" denotes a silicone oil having at least one phenyl substituent.

These non-volatile phenylated silicone oils can be chosen from those which also have at least one dimethicone fragment, or from those which do not have one.

According to the invention, a dimethicone fragment corresponds to the following unit:

—Si(CH3)2-O—.

The non-volatile phenylated silicone oil may thus be chosen from:

a) phenyl silicone oils optionally having a dimethicone fragment corresponding to the following formula (I):

$$\begin{array}{c} R \\ | \\ R-Si-O \\ | \\ R \end{array} \quad \begin{array}{c} R \\ | \\ R-Si-O-Si-R \\ | \quad \quad | \\ R \quad \quad R \end{array} \quad (I)$$

$$R-\underset{R}{\overset{|}{Si}}-O$$

in which the groups R, which are monovalent or divalent, represent, independently of each other, a methyl or a phenyl, with the proviso that at least one group R represents a phenyl.

Preferably, in this formula, the phenyl silicone oil comprises at least three, for example at least four, at least five or at least six, phenyl groups.

b) phenyl silicone oils optionally having a dimethicone fragment corresponding to the following formula (II):

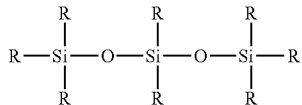
(II)

in which the groups R represent, independently of each other, a methyl or a phenyl, with the proviso that at least one group R represents a phenyl.

Preferably, in this formula, the compound of formula (II) comprises at least three, for example at least four or at least five, phenyl groups.

Mixtures of different phenylorganopolysiloxane compounds described above can be used.

Examples which may be mentioned include mixtures of triphenyl-, tetraphenyl- or pentaphenylorganopolysiloxanes.

Among the compounds of formula (II), mention may more particularly be made of phenyl silicone oils which do not have a dimethicone fragment, corresponding to formula (II) in which at least 4 or at least 5 radicals R represent a phenyl radical, the remaining radicals representing methyls.

Such non-volatile phenyl silicone oils are preferably trimethylpentaphenyltrisiloxane or tetramethyltetraphenyltrisiloxane. They are in particular sold by Dow Corning under the reference PH-1555 HRI or Dow Corning 555 Cosmetic Fluid (chemical name: 1,3,5-trimethyl-1,1,3,5,5-pentaphenyltrisiloxane; INCI name: trimethylpentaphenyltrisiloxane), or the tetramethyltetraphenyltrisiloxane sold under the reference Dow Corning 554 Cosmetic Fluid by Dow Corning can also be used.

They correspond in particular to the following formulae (III), (III'):

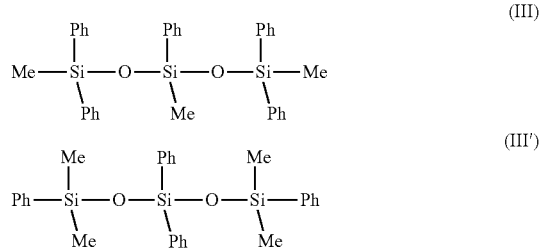

in which Me represents methyl, and Ph represents phenyl.

c) phenyl silicone oils having at least one dimethicone fragment corresponding to the following formula (IV):

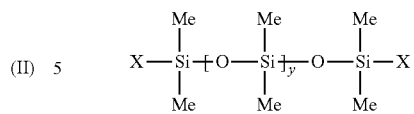
(IV)

in which Me represents methyl, y is between 1 and 1000 and X represents

—CH$_2$—CH(CH$_3$)(Ph).

d) phenyl silicone oils corresponding to formula (V) below, and mixtures thereof:

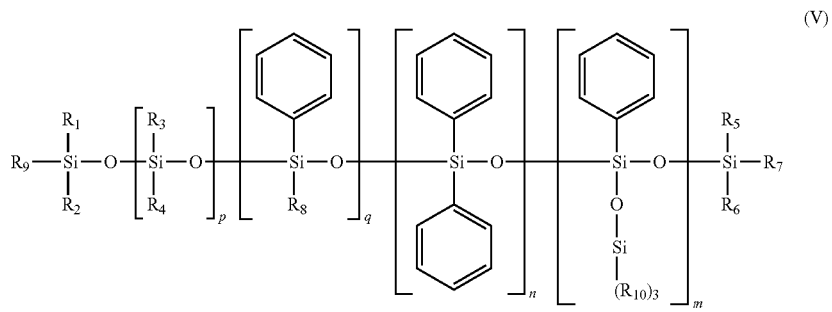
(V)

in which:

R$_1$ to R$_{10}$, independently of each other, are saturated or unsaturated, linear, cyclic or branched C$_1$-C$_{30}$ hydrocarbon-based radicals, m, n, p and q are, independently of each other, integers between 0 and 900, with the proviso that the sum m+n+q is other than 0.

Preferably, the sum m+n+q is between 1 and 100. Advantageously, the sum m+n+p+q is between 1 and 900 and preferably between 1 and 800.

Preferably, q is equal to 0.

More particularly, R$_1$ to R$_{10}$, independently of each other, represent a saturated or unsaturated, preferably saturated, linear or branched C$_1$-C$_{30}$ hydrocarbon-based radical, and in particular a preferably saturated, C$_1$-C$_{20}$, in particular C$_1$-C$_{18}$, hydrocarbon-based radical, or a monocyclic or polycyclic C$_6$-C$_{14}$, and in particular C$_{10}$-C$_{13}$, amyl radical, or an aralkyl radical, the alkyl part of which is preferably C$_1$-C$_3$ alkyl.

Preferably, R$_1$ to R$_{10}$ may each represent a methyl, ethyl, propyl, butyl, isopropyl, decyl, dodecyl or octadecyl radical, or alternatively a phenyl, tolyl, benzyl or phenethyl radical. R$_1$ to R$_{10}$ may in particular be identical, and in addition may be a methyl radical.

According to a first more particular embodiment of formula (V), mention may be made of:

i) phenyl silicone oils optionally having at least one dimethicone fragment corresponding to formula (VI) below, and mixtures thereof:

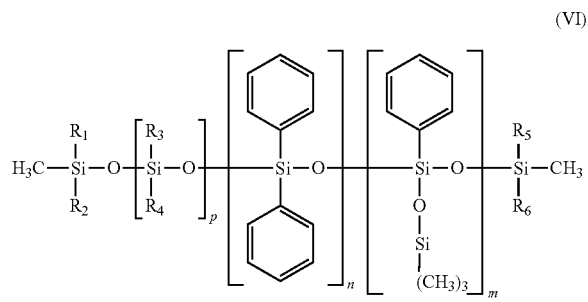
(VI)

in which:
R$_1$ to R$_6$, independently of each other, are saturated or unsaturated, linear, cyclic or branched C$_1$-C$_{30}$ hydrocarbon-based radicals, a preferably C$_6$-C$_{14}$ aryl radical or an aralkyl radical, the alkyl part of which is C$_1$-C$_3$ alkyl, m, n and p are, independently of each other, integers between 0 and 100, with the proviso that the sum n+m is between 1 and 100.

Preferably, R$_1$ to R$_6$, independently of each other, represent a C$_1$-C$_{20}$, in particular C$_1$-C$_{18}$, hydrocarbon-based, preferably alkyl, radical, or a C$_6$-C$_{14}$ aryl radical which is monocyclic (preferably C$_6$) or polycyclic and in particular C$_{10}$-C$_{13}$, or an aralkyl radical (preferably the aryl part is C$_6$ aryl; the alkyl part is C$_1$-C$_3$ alkyl).

Preferably, R$_1$ to R$_6$ may each represent a methyl, ethyl, propyl, butyl, isopropyl, decyl, dodecyl or octadecyl radical, or alternatively a phenyl, tolyl, benzyl or phenethyl radical.

R$_1$ to R$_6$ may in particular be identical, and in addition may be a methyl radical. Preferably, m=1 or 2 or 3, and/or n=0 and/or p=0 or 1 can be applied, in formula (VI).

According to one particular embodiment, the non-volatile phenylated silicone oil is chosen from phenylated silicone oils having at least one dimethicone fragment.

Preferably, such oils correspond to compounds of formula (VI) in which:

A) m=0 and n and p are, independently of each other, integers between 1 and 100.

Preferably, R$_1$ to R$_6$ are methyl radicals.

According to this embodiment, the silicone oil is preferably chosen from a diphenyl dimethicone such as KF-54 from Shin Etsu (400 cSt), KF54HV from Shin Etsu (5000 cSt), KF-50-300CS from Shin Etsu (300 cSt), KF-53 from Shin Etsu (175 cSt) or KF-50-100CS from Shin Etsu (100 cSt).

B) p is between 1 and 100, the sum n+m is between 1 and 100, and n=0.

These phenyl silicone oils optionally having at least one dimethicone fragment correspond more particularly to formula (VII) below:

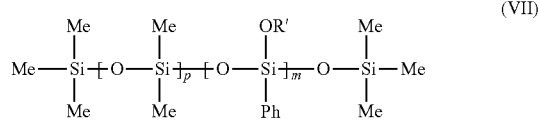
(VII)

in which Me is methyl and Ph is phenyl, OR' represents a group

—OSiMe$_3$ and p is 0 or is between 1 and 1000, and m is between 1 and 1000. In particular, m and p are such that the compound (VII) is a non-volatile oil.

According to a first embodiment of non-volatile phenylated silicone having at least one dimethicone fragment, p is between 1 and 1000 and m is more particularly such that the compound (VII) is a non-volatile oil. Trimethylsiloxyphenyldimethicone, sold in particular under the reference Belsil PDM 1000 by the company Wacker, may, for example, be used.

According to a second embodiment of non-volatile phenylated silicone not having a dimethicone fragment, p is equal to 0 and in is between 1 and 1000, and in particular is such that the compound (VII) is a non-volatile oil.

Phenyltrimethylsiloxytrisiloxane, sold in particular under the reference Dow Corning 556 Cosmetic Grade Fluid (DC556), may, for example, be used.

ii) non-volatile phenyl silicone oils not having a dimethicone fragment corresponding to formula (VIII) below, and mixtures thereof:

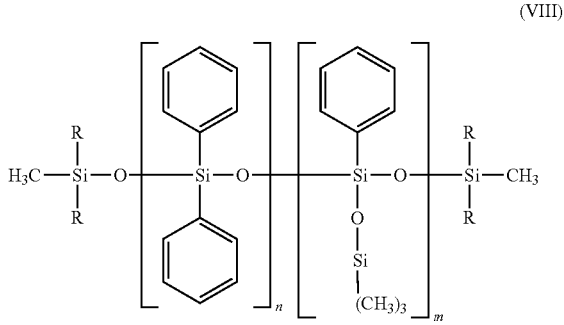
(VIII)

in which:
R, independently of each other, are saturated or unsaturated, linear, cyclic or branched C$_1$-C$_{30}$ hydrocarbon-based radicals, preferably R is a C$_1$-C$_{30}$ alkyl radical, a preferably C$_6$-C$_{14}$ aryl radical, or an aralkyl radical, the alkyl part of which is C$_1$-C$_3$ alkyl, m and n are, independently of each other, integers between 0 and 100, with the proviso that the sum n+m is between 1 and 100.

Preferably, R, independently of each other, represent a saturated or unsaturated, preferably saturated, linear or branched C$_1$-C$_{30}$ hydrocarbon-based radical, and in particular a preferably saturated, C$_1$-C$_{20}$, in particular C$_1$-C$_{18}$ and more particularly C$_4$-C$_{10}$, hydrocarbon-based radical, a monocyclic or polycyclic C$_6$-C$_{14}$, and in particular C$_{10}$-C$_{13}$, aryl radical, or an aralkyl radical of which preferably the aryl part is C$_6$ aryl and the alkyl part is C$_1$-C$_3$ alkyl.

Preferably, the R may each represent a methyl, ethyl, propyl, butyl, isopropyl, decyl, dodecyl or octadecyl radical, or alternatively a phenyl, tolyl, benzyl or phenethyl radical.

The R may in particular be identical, and in addition may be a methyl radical.

Preferably, m=1 or 2 or 3, and/or n=0 and/or p=0 or 1 can be applied, in formula (VIII).

According to one preferred embodiment, n is an integer between 0 and 100 and m is an integer between 1 and 100, with the proviso that the sum n+m is between 1 and 100, in formula (VIII). Preferably, R is a methyl radical.

According to one embodiment, a phenyl silicone oil of formula (VIII) with a viscosity at 25° C. of between 5 and 1500 mm$^2$/s (i.e. 5 to 1500 cSt), and preferably with a viscosity of between 5 and 1000 mm$^2$/s (i.e. 5 to 1000 cSt), may be used.

According to this embodiment, the non-volatile phenyl silicone oil is preferably chosen from phenyl trimethicones (when n=0) such as DC556 from Dow Corning (22.5 cSt), or else from diphenylsiloxyphenyl trimethicone oil (when m and n are between 1 and 100) such as KF56 A from Shin Etsu, or the Silbione 70663V30 oil from Rhone-Poulenc (28 cSt). The values in parentheses represent the viscosities at 25° C.

e) phenyl silicone oils optionally having at least one dimethicone fragment corresponding to the following formula, and mixtures thereof:

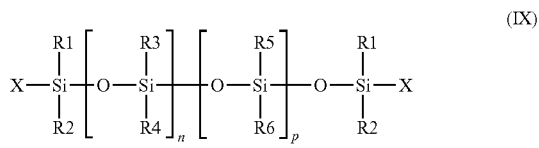

in which:

$R_1$, $R_2$, $R_5$ and $R_6$, which may be identical or different, are an alkyl radical containing 1 to 6 carbon atoms, $R_3$ and $R_4$, which may be identical or different, are an alkyl radical containing from 1 to 6 carbon atoms or an aryl radical (preferably $C_6$-$C_{14}$), with the proviso that at least one of $R_3$ and $R_4$ is a phenyl radical, X is an alkyl radical containing from 1 to 6 carbon atoms, a hydroxyl radical or a vinyl radical, n and p being an integer greater than or equal to 1, chosen so as to give the oil a weight-average molecular weight of less than 200 000 g/mol, preferably less than 150 000 g/mol and more preferably less than 100 000 g/mol.

f) and a mixture thereof.

Non-Volatile Fluoro Oils

The term "fluoro oil" is intended to mean an oil containing at least one fluorine atom.

As examples of fluoro oils, mention may be made of fluorosilicone oils, fluorinated polyethers, fluorosilicones in particular as described in document EP-A-847 752 and perfluoro compounds.

According to the invention, the term "perfluoro compounds" is intended to mean compounds in which all the hydrogen atoms have been replaced with fluorine atoms.

According to one preferred embodiment, the fluoro oil is chosen from perfluoro oils.

As examples of perfluoro oils, mention may be made of perfluorodecalins and perfluoroperhydrophenanthrenes.

According to one preferred embodiment, the fluoro oil is chosen from perfluoroperhydrophenanthrenes, and in particular the Fiflow® products sold by the company Créations Couleurs. In particular, use may be made of the fluoro oil of which the INCI name is Perfluoroperhydrophenanthrene, sold under the reference Fiflow 220 by the company F2 Chemicals.

Polar Non-Volatile Hydrocarbon-Based Oils

The term "hydrocarbon-based oil" is intended to mean an oil formed essentially from, or even constituted by, carbon and hydrogen atoms, and possibly oxygen and nitrogen atoms, and not containing any silicon or fluorine atoms.

It may contain alcohol, ester, ether, carboxylic acid, amine and/or amide groups.

Preferably, the hydrocarbon-based oil, in addition to being free of silicon and fluorine, is free of heteroatoms such as N and P. The hydrocarbon-based oil is therefore different from a silicone oil and from a fluoro oil.

In the present case, the non-volatile hydrocarbon-based oil comprises at least one oxygen atom.

In particular, this non-volatile hydrocarbon-based oil comprises at least one alcohol function (it is then an "alcohol oil") or at least one ester function (it is then an "ester oil").

The ester oils that may be used in the compositions according to the invention may in particular be hydroxylated.

The composition may comprise one or more non-volatile hydrocarbon-based oils, in particular chosen from:

$C_{10}$-$C_{26}$ alcohols preferably monoalcohols.

More particularly, the $C_{10}$-$C_{26}$ alcohols are saturated or unsaturated, and branched or unbranched, and comprise from 10 to 26 carbon atoms.

Preferably, the $C_{10}$-$C_{26}$ alcohols are fatty alcohols, which are preferably branched when they comprise at least 16 carbon atoms.

As examples of fatty alcohols that may be used according to the invention, mention may be made of linear or branched fatty alcohols, of synthetic origin or alternatively of natural origin, for example alcohols derived from plant material (coconut, palm kernel, palm, etc.) or animal material (tallow, etc.).

Needless to say, other long-chain alcohols may also be used, for instance ether alcohols or alternatively "Guerbet" alcohols.

Finally, use may also be made of certain more or less long fractions of alcohols of natural origin, for instance coconut ($C_{12}$ to $C_{16}$) or tallow ($C_{16}$ to $C_{18}$) or compounds of diol or cholesterol type.

Use is preferably made of a fatty alcohol comprising from 10 to 24 carbon atoms and more preferentially from 12 to 22 carbon atoms.

As particular examples of fatty alcohols that may preferably be used, mention may be made in particular of lauryl alcohol, myristyl alcohol, isostearyl alcohol, palmityl alcohol, oleyl alcohol, behenyl alcohol, erucyl alcohol, arachidyl alcohol, 2-butyloctanol, 2-undecylpentadecanol, 2-hexyldecyl alcohol, isocetyl alcohol and octyldodecanol, and mixtures thereof. Preferably, the fatty alcohol is chosen from lauryl alcohol, isostearyl alcohol, oleyl alcohol, 2-butyloctanol, 2-undecylpentadecanol, 2-hexyldecyl alcohol, isocetyl alcohol and octyldodecanol, and mixtures thereof.

According to one advantageous embodiment of the invention, the alcohol is chosen from octyldodecanol;

optionally hydroxylated monoesters, diesters or triesters of a $C_2$-$C_8$ monocarboxylic or polycarboxylic acid and of a $C_2$-$C_8$ alcohol.

In particular:

optionally hydroxylated monoesters of a $C_2$-$C_8$ carboxylic acid and of a $C_2$-$C_8$ alcohol, optionally hydroxylated diesters of a $C_2$-$C_8$ dicarboxylic acid and of a $C_2$-$C_8$ alcohol, such as diisopropyl adipate, 2-diethylhexyl adipate, dibutyl adipate, diisostearyl adipate or 2-diethylhexyl succinate, optionally hydroxylated triesters of a $C_2$-$C_8$ tricarboxylic acid and of a $C_2$-$C_8$ alcohol, such as citric acid esters, such as trioctyl citrate, triethyl citrate, acetyl tributyl citrate, tributyl citrate or acetyl tributyl citrate;

esters of a $C_2$-$C_8$ polyol and of one or more $C_2$-$C_8$ carboxylic acids, such as glycol diesters of monoacids, such as neopentyl glycol diheptanoate, or glycol triesters of monoacids, such as triacetin;

ester oils, in particular having between 18 and 70 carbon atoms.

Examples that may be mentioned include monoesters, diesters or triesters.

The ester oils may be hydroxylated or non-hydroxylated.

The non-volatile ester oil may for example be chosen from:

monoesters comprising between 18 and 40 carbon atoms in total, in particular the monoesters of formula $R_1COOR_2$ in which $R_1$ represents a saturated or unsaturated, linear or branched or aromatic fatty acid residue comprising from 4 to 40 carbon atoms and $R_2$ represents a hydrocarbon-based chain, which is in particular branched, containing from 4 to 40 carbon atoms, on condition that $R_1+R_2 \geq 18$, for instance Purcellin oil (cetostearyl octanoate), isononyl isononanoate, $C_{12}$ to $C_{15}$ alkyl benzoate, 2-ethylhexyl palmitate, octyldodecyl neopentanoate, 2-octyldodecyl stearate, 2-octyldodecyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate or 2-octyldodecyl myristate.

Preferably, they are esters of formula $R_1COOR_2$ in which $R_1$ represents a linear or branched fatty acid residue containing from 4 to 40 carbon atoms and $R_2$ represents a hydrocarbon-based chain that is in particular branched, containing from 4 to 40 carbon atoms, $R_1+R_2$ being such that $R_1+R_2 \geq 18$.

Even more particularly, the ester comprises between 18 and 40 carbon atoms in total.

Preferred monoesters that may be mentioned include isononyl isononanoate, oleyl erucate and/or 2-octyldodecyl neopentanoate;

monoesters of a fatty acid, in particular of 18 to 22 carbon atoms, and in particular of lanolic acid, oleic acid, lauric acid or stearic acid, and of diols, for instance propylene glycol monoisostearate;

diesters, in particular comprising between 18 and 60 carbon atoms in total and in particular between 18 and 50 carbon atoms in total. Use may in particular be made of diesters of a dicarboxylic acid and of monoalcohols, preferably such as diisostearyl malate, or glycol diesters of monocarboxylic acids, such as neopentyl glycol diheptanoate, propylene glycol dioctanoate, diethylene glycol diisononanoate or polyglyceryl-2 diisostearate (in particular such as the compound sold under the commercial reference Dermol DGDIS by the company Alzo);

hydroxylated monoesters and diesters, preferably with a total carbon number ranging from 18 to 70, for instance polyglyceryl-3 diisostearate, isostearyl lactate, octyl hydroxystearate, octyldodecyl hydroxystearate, diisostearyl malate or glyceryl stearate;

triesters, in particular comprising between 35 and 70 carbon atoms in total, in particular such as triesters of a tricarboxylic acid, such as triisostearyl citrate, or tridecyl trimellitate, or glycol triesters of monocarboxylic acids such as polyglyceryl-2 triisostearate;

tetraesters, in particular with a total carbon number ranging from 35 to 70, such as pentaerythritol or polyglycerol tetraesters of a monocarboxylic acid, for instance pentaerythrityl tetrapelargonate, pentaerythrityl tetraisoslearate, pentaerythrityl tetraisononanoate, glyceryl tris(2-decyl)tetradecanoate, polyglyceryl-2 tetraisostearate or pentaerythrityl tetrakis(2-decyl)tetradecanoate;

polyesters obtained by condensation of an unsaturated fatty acid dimer and/or trimer and of diol, such as those described in patent application FR 0 853 634, in particular such as dilinoleic acid and 1,4-butanediol. Mention may in particular be made in this respect of the polymer sold by Biosynthis under the name Viscoplast 14436H (INCI name: dilinoleic acid/butanediol copolymer), or else copolymers of polyols and of dimer diacids, and esters thereof, such as Hailucent ISDA;

esters and polyesters of diol dimer and of monocarboxylic or dicarboxylic acid, such as esters of diol dimer and of fatty acid and esters of diol dimer and of dicarboxylic acid dimer, in particular which may be obtained from a dicarboxylic acid dimer derived in particular from the dimerization of an unsaturated fatty acid in particular of $C_8$ to $C_{34}$, especially of $C_{12}$ to $C_{22}$, in particular of $C_{16}$ to $C_{20}$ and more particularly of $C_{18}$, such as esters of dilinoleic diacids and of dilinoleic diol dimers, for instance those sold by the company Nippon Fine Chemical under the trade names Lusplan DD-DA5® and DD-DA7®;

polyesters resulting from the esterification of at least one triglyceride of hydroxylated carboxylic acid(s) with an aliphatic monocarboxylic acid and with an aliphatic dicarboxylic acid, which is optionally unsaturated, for instance the succinic acid and isostearic acid castor oil sold under the reference Zenigloss by Zenitech;

hydrocarbon-based vegetable oils such as fatty acid triglycerides (which are liquid at ambient temperature), in particular of fatty acids containing from 7 to 40 carbon atoms, such as heptanoic or octanoic acid triglycerides or jojoba oil; mention may be made in particular of saturated triglycerides such as capiylic/capric triglycerides and mixtures thereof, for example such as the product sold under the reference Myritol 318 from Cognis, glyceryl triheptanoate, glyceryl trioctanoate, and $C_{18}$-$C_{36}$ acid triglycerides such as those sold under the reference Dub TGI 24 by Stéarineries Dubois, and unsaturated triglycerides such as castor oil, olive oil, ximenia oil or pracaxi oil;

vinylpyrrolidone/l-hexadecene copolymers, for instance the product sold under the name Antaron V-216 (also known as Ganex V216) by the company ISP (MW=7300 g/mol);

$C_{12}$-$C_{26}$ fatty acids, preferably $C_{12}$-$C_{22}$ fatty acids, which are preferably unsaturated, such as oleic acid, linoleic acid or linolenic acid, and mixtures thereof;

dialkyl carbonates, the 2 alkyl chains possibly being identical or different, such as dicaprylyl carbonate sold under the name Cetiol CC® by Cognis;

and mixtures thereof.

Non-Polar Non-Volatile Hydrocarbon-Based Oils

The composition according to the invention can also comprise at least one non-polar non-volatile hydrocarbon-based oil.

These oils may be of vegetable, mineral or synthetic origin.

For the purposes of the present invention, the term "non-polar oil" is intended to mean an oil of which the solubility parameter at 25° C., $\delta_a$, is equal to 0 $(J/cm^3)^{1/2}$.

The definition and calculation of the solubility parameters in the Hansen three-dimensional solubility space are described in the paper by C. M. Hansen: "The three-dimensional solubility parameters", J. Paint Technol., 39, 105 (1967).

According to this Hansen space:

$\delta_D$ characterizes the London dispersion forces derived from the formation of dipoles induced during molecular impacts;

$\delta_P$ characterizes the Debye interaction forces between permanent dipoles and also the Keesom interaction forces between induced dipoles and permanent dipoles;

$\delta_h$ characterizes the specific interaction forces (such as hydrogen bonding, acid/base, donor/acceptor, etc.); and $\delta_a$ is determined by the equation: $\delta_a = (\delta_p^2 + \delta_h^2)^{1/2}$.

The parameters $\delta_p$, $\delta_h$, $\delta_D$ and $\delta_a$ are expressed in $(J/cm^3)^{1/2}$.

The term "hydrocarbon-based oil" is intended to mean an oil formed essentially from, or even constituted of, carbon and hydrogen atoms, and optionally oxygen and nitrogen atoms, and not containing any silicon or fluorine atoms. It may contain alcohol, ester, ether, carboxylic acid, amine and/or amide groups. Preferably, the non-polar hydrocarbon oils are chosen from oils formed essentially from hydrogen atoms and carbon atoms.

Preferably, the non-polar non-volatile hydrocarbon-based oil may be chosen from linear or branched hydrocarbons of mineral or synthetic origin, such as:

liquid paraffin or derivatives thereof,
squalane,
isoeicosane,
naphthalene oil,
polybutenes or hydrogenated polybutenes such for instance as Indopol H-100 (molar mass or MW=965 g/mol), Indopol H-300 (MW=1340 g/mol) and Indopol H-1500 (MW=2160 g/mol) sold or manufactured by the company Amoco,
polyisobutenes or hydrogenated polyisobutenes, particularly hydrogenated, such as for example Parleam® sold by the company Nippon Oil Fats, Panalane H-300 E sold or manufactured by the company Amoco (MW=1340 g/mol), Viseal 20000 sold or manufactured by the company Synteal (MW=6000 g/mol) and Rewopal PIB 1000 sold or manufactured by the company Witco (MW=1000 g/mol), or alternatively Parleam Lite sold by NOF Corporation,
decene/butene copolymers, polybutene/polyisobutene copolymers, in particular Indopol L-14,
polydecenes and hydrogenated polydecenes such as for instance, Puresyn 10 (MW=723 g/mol) and Puresyn 150 (MW=9200 g/mol) sold or manufactured by the company Mobil Chemicals, or alternatively Puresyn 6 sold by ExxonMobil Chemical),
and mixtures thereof.

In accordance with one particular variant of the invention, the composition comprises at least one non-volatile oil chosen from non-volatile silicone oils, polar or non-polar, non-volatile hydrocarbon-based oils, or mixtures thereof.

In accordance with this preferred embodiment, said non-volatile silicone oils are chosen from phenylated silicones, or even more preferably from non-volatile phenylated silicones not having a dimethicone fragment. More particularly, the non-volatile phenylated silicone oils not having a dimethicone fragment are chosen from (I), with radicals R such that the silicone has no dimethicone fragment; (II) with radicals R such that the silicone has no dimethicone fragment, in particular formulae (III) and (III'); (V) with p=0; (VI) with p=0; (VII) with p=0; (VIII); (IX) with radicals R such that the silicone has no dimethicone fragment; or mixtures thereof.

Furthermore, preferably, the non-volatile phenylated silicone oils are chosen from those of formula (II), more particularly non-volatile phenyl silicone oils of formula (III) or (III').

In addition, the non-volatile hydrocarbon-based oil(s) is (are) more particularly chosen from polar non-volatile oils, such as for example $C_{10}$-$C_{26}$ alcohols, or ester oils; from non-polar oils; and mixtures thereof.

Preferably, the composition comprises at least one polar oil are or chosen from $C_{10}$-$C_{26}$ alcohols; hydroxylated monoesters and diesters; monoesters comprising between 18 and 40 carbon atoms in total; triesters comprising between 35 and 70 carbon atoms in total, or mixtures thereof, or at least one non-polar oil chosen from hydrogenated or non-hydrogenated poly(iso)butylenes, and also mixtures thereof.

Preferably, the composition comprises at least one polar oil, more particularly octyldodecanol.

In accordance with one particularly advantageous embodiment of the invention, the composition comprises at least one non-volatile oil chosen from non-volatile phenylated silicone oils, preferably such as those which have just been described in detail, and polar non-volatile hydrocarbon-based oils, or mixtures thereof.

Film-Forming Agent

Moreover, the composition according to the invention comprises at least one film-forming agent.

The term "film-forming polymer" is intended to mean a polymer that is capable of forming, by itself or in the presence of an auxiliary film-forming agent, a continuous deposit on a support, in particular on keratin materials.

More particularly, the content of film-forming agent(s) represents from 0.5% to 30% by weight of active material and preferably from 1% to 20% by weight, relative to the total weight of the composition.

As examples of film-forming polymers, mention may be made of synthetic polymers of polycondensate type or of radical type; silicone resins; alkylcelluloses; and combinations thereof.

Polycondensates

Among the polycondensates, mention may thus be made of anionic, cationic, non-ionic or amphoteric polyurethanes, polyurethane-acrylics, polyurethane-polyvinylpyrrolidones, polyester-polyurethanes, polyether-polyurethanes, polyureas, polyurea/polyurethanes, and mixtures thereof.

The polyurethane may be, for example, an aliphatic, cycloaliphatic or aromatic polyurethane, polyurea/urethane or polyurea copolymer comprising, alone or as a mixture:

at least one block of aliphatic and/or cycloaliphatic and/or aromatic polyester origin, and/or
at least one substituted or unsubstituted, branched or unbranched silicone block, for example polydimethylsiloxane or polymethylphenylsiloxane, and/or
at least one block comprising fluoro groups.

The polyurethanes as defined may also be obtained from branched or unbranched polyesters or from alkyds comprising mobile hydrogens, which are modified by reaction with a diisocyanate and a difunctional organic compound (for example dihydroxy, diamino or hydroxyamino), also comprising either a carboxylic acid or carboxylate group, or a sulfonic acid or sulfonate group, or alternatively a neutralizable tertiary amine group or a quaternary anunonium group.

As polyurethane that can be used according to the invention, mention may be made of those sold under the name Ncorez R-981 by the company Zeneca and under the names Sancure 875, Avalure UR 425 and Sancure 861 by the company Sanncor.

Among the polycondensates, mention may also be made of polyesters, polyesteramides, fatty-chain polyesters, polyamides and epoxyester resins.

The polyesters may be obtained, in a known manner, by polycondensation of aliphatic or aromatic diacids with aliphatic or aromatic polyols. As aliphatic diacids, use may be made of succinic acid, glutaric acid, adipic acid, pimelic acid, suberic acid or sebacic acid. As aromatic diacids, use may be made of terephthalic acid or isophthalic acid, or alternatively a derivative such as phthalic anhydride. As polyols, use may be made of ethylene glycol, propylene glycol, diethylene glycol, neopentyl glycol, cyclohexanedimethanol, 4,4'-(1-methylpropylidene)bisphenol, glycerol, pentaerythritol, sorbitol and trimethylolpropane.

The polyesteramides may be obtained in a manner analogous to that of the polyesters, by polycondensation of diacids with diamines or amino alcohols. Diamines that may be used are ethylenediamine, hexamethylenediamine and meta- or para-phenylenediamine. An amino alcohol that may be used is monoethanolamine.

As monomer bearing an anionic group which may be used during the polycondensation, mention may be made, for example, of dimethylolpropionic acid, trimellitic acid or a derivative such as trimellitic anhydride, the sodium salt of pentanediol-3-sulfonic acid and the sodium salt of 5-sulfo-1,3-benzenedicarboxylic acid.

The fatty-chain polyesters may be obtained using fatty-chain diols during the polycondensation. The epoxyester resins may be obtained by polycondensation of fatty acids with a condensate comprising α,ω-diepoxy end groups.

Free-Radical Polymers

The term "free-radical polymer" is intended to mean a polymer obtained by polymerization of unsaturated and in particular ethylenically unsaturated monomers, each monomer being capable of homopolymerizing (unlike polycondensates). The polymers of free-radical type may in particular be vinyl polymers or copolymers, in particular acrylic polymers.

The vinyl polymers may result from the polymerization of one or more ethylenically unsaturated monomers containing at least one acid group and/or esters of these acid monomers and/or amides of these acid monomers.

Use is preferably made of anionic free-radical polymers, i.e. monomers having at least one monomer comprising an acid group. As monomer bearing an acid group, use may be made of α,β-ethylenic unsaturated carboxylic acids such as acrylic acid, methacrylic acid, crotonic acid, maleic acid or itaconic acid. (Meth)acrylic acid and crotonic acid are in particular used, and more especially (meth)acrylic acid.

The esters of acid monomers are advantageously chosen from (meth)acrylic acid esters (also known as (meth)acrylates), in particular alkyl (meth)acrylates, in particular $C_1$-$C_{20}$ and preferably $C_1$-$C_8$ alkyl (meth)acrylates, aryl (meth)acrylates, in particular $C_6$-$C_{10}$ aryl (meth)acrylates, and hydroxyalkyl (meth)acrylates, in particular $C_2$-$C_6$ hydroxyalkyl (meth)acrylates.

Among the alkyl (meth)acrylates that may be mentioned are methyl methacrylate, ethyl methacrylate, butyl methacrylate, isobutyl methacrylate, 2-ethylhexyl methacrylate and lauryl methacrylate.

Mention may be made, among hydroxyalkyl (meth)acrylates, of hydroxyethyl acrylate, 2-hydroxypropyl acrylate, hydroxyethyl methacrylate or 2-hydroxypropyl methacrylate. Mention may be made, among aryl (meth)acrylates, of benzyl acrylate and phenyl acrylate.

According to the present invention, the alkyl group of these esters can be either fluorinated or perfluorinated, i.e. some or all of the hydrogen atoms of the alkyl group are replaced with fluorine atoms.

Examples of amides of the acid monomers that may be mentioned are (meth)acrylamides, and in particular N-alkyl (meth)acrylamides, in particular of a $C_2$-$C_{12}$ alkyl. Among the N-alkyl(meth)acrylamides that may be mentioned are N-ethylacrylamide, N-t-butylacrylamide and N-t-octylacrylamide.

The vinyl polymers may also result from the homopolymerization or copolymerization of monomers chosen from vinyl esters and styrene monomers. In particular, these monomers may be polymerized with acid monomers and/or esters thereof and/or amides thereof, such as those mentioned previously. Examples of vinyl esters that may be mentioned are vinyl acetate, vinyl neodecanoate, vinyl pivalate, vinyl benzoate and vinyl t-butylbenzoate. Styrene monomers that may be mentioned include styrene and α-methylstyrene.

The list of monomers given above is not limiting, and it is possible to use any monomer known to those skilled in the art included in the categories of acrylic and vinyl monomers (including monomers modified with a silicone chain).

As acrylic polymer that can be used according to the invention, mention may be made of those sold under the names c XK-90, Neocryl A-1070 or A-1090, Neocryl BT-62, Neocryl A-1079 or Neocryl A-523 by the company Zeneca, or Dow Latex 432 by the company Dow Chemical.

Mention may also be made of the polymers resulting from the free-radical polymerization of one or more free-radical monomers inside and/or partially at the surface of preexisting particles of at least one polymer chosen from the group consisting of polyurethanes, polyureas, polyesters, polyesteramides and/or alkyds. These polymers are generally referred to as "hybrid polymers".

In order to improve the water resistance of the polymeric film, it is preferable to use polymers resulting from the polymerization of ethylenically unsaturated monomers, and in particular (meth)acrylic, vinyl, styrene and (meth)acrylate polymers, including copolymers, and mixtures thereof.

Among the free-radical polymers, vinyl polymers comprising at least one carbosiloxane dendrimer-based unit and film-forming ethylenic block copolymers are quite particularly preferred.

Vinyl Polymer Comprising at Least One Carbosiloxane Dendrimer-Based Unit

The vinyl polymer has a backbone and at least one side chain, which comprises a carbosiloxane dendrimer-based unit having a carbosiloxane dendrimer structure.

The term "carbosiloxane dendrimer structure" in the context of the present invention represents a molecular structure with branched groups of high molecular weights, said structure having high regularity in the radial direction starting from the bond to the backbone. Such carbosiloxane dendrimer structures are described in the form of a highly branched siloxane-silylalkylene copolymer in Japanese patent application JP 9-171 154.

A vinyl polymer according to the invention may contain carbosiloxane dendrimer-based units that may be represented by the following general formula (I):

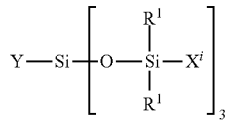
(I)

in which:
$R^1$ represents an aryl group containing from 5 to 10 carbon atoms or an alkyl group containing from 1 to 10 carbon atoms;
$X^i$ represents a silylalkyl group which, when i=1, is represented by formula (II):

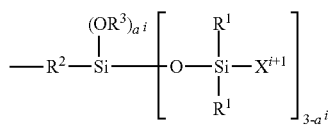
(II)

in which:
$R^1$ is as defined above in formula (I),
$R^2$ represents an alkylene radical containing from 2 to 10 carbon atoms,
$R^3$ represents an alkyl group containing from 1 to 10 carbon atoms,
$X^{i+i}$ is chosen from: a hydrogen atom, an alkyl group containing from 1 to 10 carbon atoms, an aryl group containing from 5 to 10 carbon atoms and a silylalkyl group defined above of formula (II) with i=i+1,
i is an integer from 1 to 10 which represents the generation of said silylalkyl group, and
$a^i$ is an integer from 0 to 3;
Y represents a radical-polymerizable organic group chosen from:
organic groups containing a methacrylic group or an acrylic group, said organic groups being represented by the formulae:

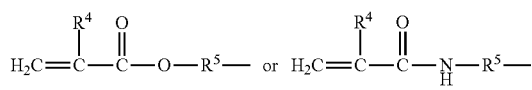

in which:
$R^4$ represents a hydrogen atom or an alkyl group containing from 1 to 10 carbon atoms; and
$R^5$ represents an alkylene group containing from 1 to 10 carbon atoms, such as a methylene group, an ethylene group, a propylene group or a butylene group, methylene and propylene groups being preferred; and
organic groups containing a styryl group of formula:

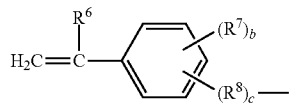

in which:
$R^6$ represents a hydrogen atom or an alkyl group containing from 1 to 10 carbon atoms, such as a methyl group, an ethyl group, a propyl group or a butyl group, the methyl group being preferred:
$R^7$ represents an alkyl group containing from 1 to 10 carbon atoms;
$R^8$ represents an alkylene group containing from 1 to 10 carbon atoms, such as a methylene group, an ethylene group, a propylene group or a butylene group, the ethylene group being preferred;
b is an integer from 0 to 4; and
c is 0 or 1, such that, if c is 0, —$(R^8)_c$— represents a bond.

According to one embodiment, $R^1$ may represent an aryl group containing from 5 to 10 carbon atoms or an alkyl group containing from 1 to 10 carbon atoms. The alkyl group may preferably be represented by a methyl group, an ethyl group, a propyl group, a butyl group, a pentyl group, an isopropyl group, an isobutyl group, a cyclopentyl group or a cyclohexyl group. The aryl group may preferably be represented by a phenyl group and a naphthyl group. The methyl and phenyl groups are more particularly preferred, and the methyl group is preferred among all.

According to one embodiment, $R^2$ represents an alkylene group containing from 2 to 10 carbon atoms, in particular a linear alkylene group, such as an ethylene, propylene, butylene or hexylene group; or a branched alkylene group, such as a methylmethylene, methylethylene, 1-methylpentylene or 1,4-dimethylbutylene group.

The ethylene, methylethylene, hexylene, 1-methylpentylene and 1,4-dimethylbutylene groups are preferred among all.

According to one embodiment, $R^3$ is chosen from methyl, ethyl, propyl, butyl and isopropyl groups.

In formula (II), i indicates the number of generations and thus corresponds to the number of repeats of the silylalkyl group.

For example, when the generation number is equal to 1, the carbosiloxane dendrimer may be represented by the general formula shown below, in which Y, $R^1$, $R^2$ and $R^3$ are as defined above, $R^{12}$ represents a hydrogen atom or is identical to $R^1$; $a^1$ is identical to $a^i$. Preferably, the total average number of groups $OR^3$ in a molecule is within the range from 0 to 7.

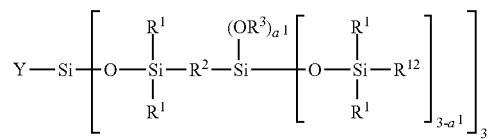

When the generation number is equal to 2, the carbosiloxane dendrimer may be represented by the general formula below, in which Y, $R^1$, $R^2$, $R^3$ and $R^{12}$ are the same as defined above; $a^1$ and $a^2$ represent the $a^i$ of the indicated generation. Preferably, the total average number of groups $OR^3$ in a molecule is within the range from 0 to 25.

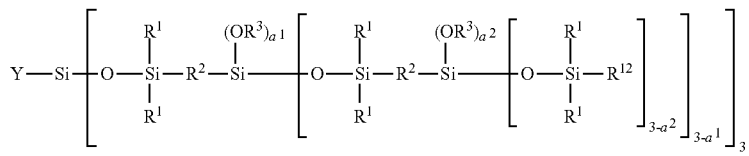

When the generation number is equal to 3, the carbosiloxane dendrimer is represented by the general formula below, in which Y, $R^2$, $R^3$ and $R^{12}$ are the same as defined above; $a^1$, $a^2$ and $a^3$ represent the $a^i$ of the indicated generation. Preferably, the total average number of groups $OR^3$ in a molecule is within the range from 0 to 79.

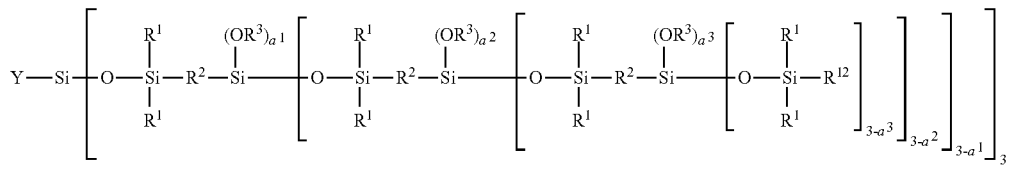

A vinyl polymer containing at least one carbosiloxane dendrimer-based unit has a molecular side chain containing a carbosiloxane dendrimer structure, and may be the product of polymerization of:
(A) from 0 to 99.9 parts by weight of a vinyl monomer; and
(B) from 100 to 0.1 parts by weight of a carbosiloxane dendrimer containing a radical-polymerizable organic group, represented by general formula (I) as defined above.

The monomer of vinyl type that is the component (A) in the vinyl polymer having at least one carbosiloxane dendrimer-based unit is a monomer of vinyl type that contains a radical-polymerizable vinyl group.

There is no particular limitation as regards such a monomer.

The following are examples of this monomer of vinyl type: methyl methacrylate, ethyl methacrylate, n-propyl methacrylate, isopropyl methacrylate or a methacrylate of an analagous lower alkyl; glycidyl methacrylate; butyl methacrylate, butyl acrylate, n-butyl methacrylate, isobutyl methacrylate, tert-butyl acrylate, tert-butyl methacrylate, n-hexyl methacrylate, cyclohexyl methacrylate, 2-ethylhexyl acrylate, 2-ethylhexyl methacrylate, octyl methacrylate, lauryl methacrylate, stearyl acrylate, stearyl methacrylate or a higher-analogue methacrylate; vinyl acetate, vinyl propionate or a vinyl ester of an analagous lower fatty acid; vinyl caproate, vinyl 2-ethylhexoate, vinyl laurate, vinyl stearate or an ester of a higher fatty acid analogue; styrene, vinyltoluene, benzyl methacrylate, phenoxyethyl methacrylate, vinylpyrrolidone or similar vinylaromatic monomers; methacrylamide, N-methylolmethacrylamide, N-methoxymethylmethacrylamide, isobutoxymethoxymethacrylamide, N,N-dimethylmethacrylamide or similar monomers of vinyl type containing amide groups; hydroxyethyl methacrylate, hydroxypropyl alcohol methacrylate or similar monomers of vinyl type containing hydroxyl groups; acrylic acid, methacrylic acid, itaconic acid, crotonic acid, fumaric acid, maleic acid or similar monomers of vinyl type containing a carboxylic acid group; tetrahydrofurfuryl methacrylate, butoxyethyl methacrylate, ethoxydiethylene glycol methacrylate, polyethylene glycol methacrylate, polypropylene glycol monomethacrylate, hydroxybutyl vinyl ether, cetyl vinyl ether, 2-ethylhexyl vinyl ether or a similar monomer of vinyl type with ether bonds; methacryloxypropyltrimethoxysilane, polydimethylsiloxane containing a methacrylic group on one of its molecular ends, polydimethylsiloxane containing a styryl group on one of its molecular ends, or a similar silicone compound containing unsaturated groups; butadiene; vinyl chloride; vinylidene chloride; methacrylonitrile; dibutyl fumarate; anhydrous maleic acid; anhydrous succinic acid; methacryl glycidyl ether; an organic salt of an amine, an ammonium salt, and an alkali metal salt of methacrylic acid, of itaconic acid, of crotonic acid, of maleic acid or of fumaric acid; a radical-polymerizable unsaturated monomer containing a sulfonic acid group such as a styrenesulfonic acid group; a quaternary ammonium salt derived from methacrylic acid, such as 2-hydroxy-3-methacryloxypropyltrimethylammonium chloride; and a methacrylic acid ester of an alcohol containing a tertiary amine group, such as a methacrylic acid ester of diethylamine.

Multifunctional vinyl monomers may also be used.

The following represent examples of such compounds: trimethylolpropane trimethacrylate, pentaerythrityl trimethacrylate, ethylene glycol dimethacrylate, tetraethylene glycol dimethacrylate, polyethylene glycol dimethacrylate, 1,4-butanediol dimethacrylate, 1,6-hexanediol dimethacrylate, neopentyl glycol dimethacrylate, trimethylolpropanetrioxyethyl methacrylate, tris(2-hydroxyethyl)isocyanurate dimethacrylate, tris(2-hydroxyethyl)isocyanurate trimethacrylate, polydimethylsiloxane capped with styryl groups containing divinylbenzene groups on both ends, or similar silicone compounds containing unsaturated groups.

A carbosiloxane dendrimer, which is the component (B), may be represented by formula (I) as defined above.

The following represent the preferred examples of group Y of formula (I): an acryloxymethyl group, a 3-acryloxypropyl group, a methacryloxymethyl group, a 3-methacryloxypropyl group, a 4-vinylphenyl group, a 3-vinylphenyl group, a 4-(2-propenyl)phenyl group, a 3-(2-propenyl)phenyl group, a 2-(4-vinylphenyl)ethyl group, a 2-(3-vinylphenyl)ethyl group, a vinyl group, an allyl group, a methallyl group and a 5-hexenyl group.

A carbosiloxane dendrimer according to the present invention can be represented by the formulae having the average structures below:

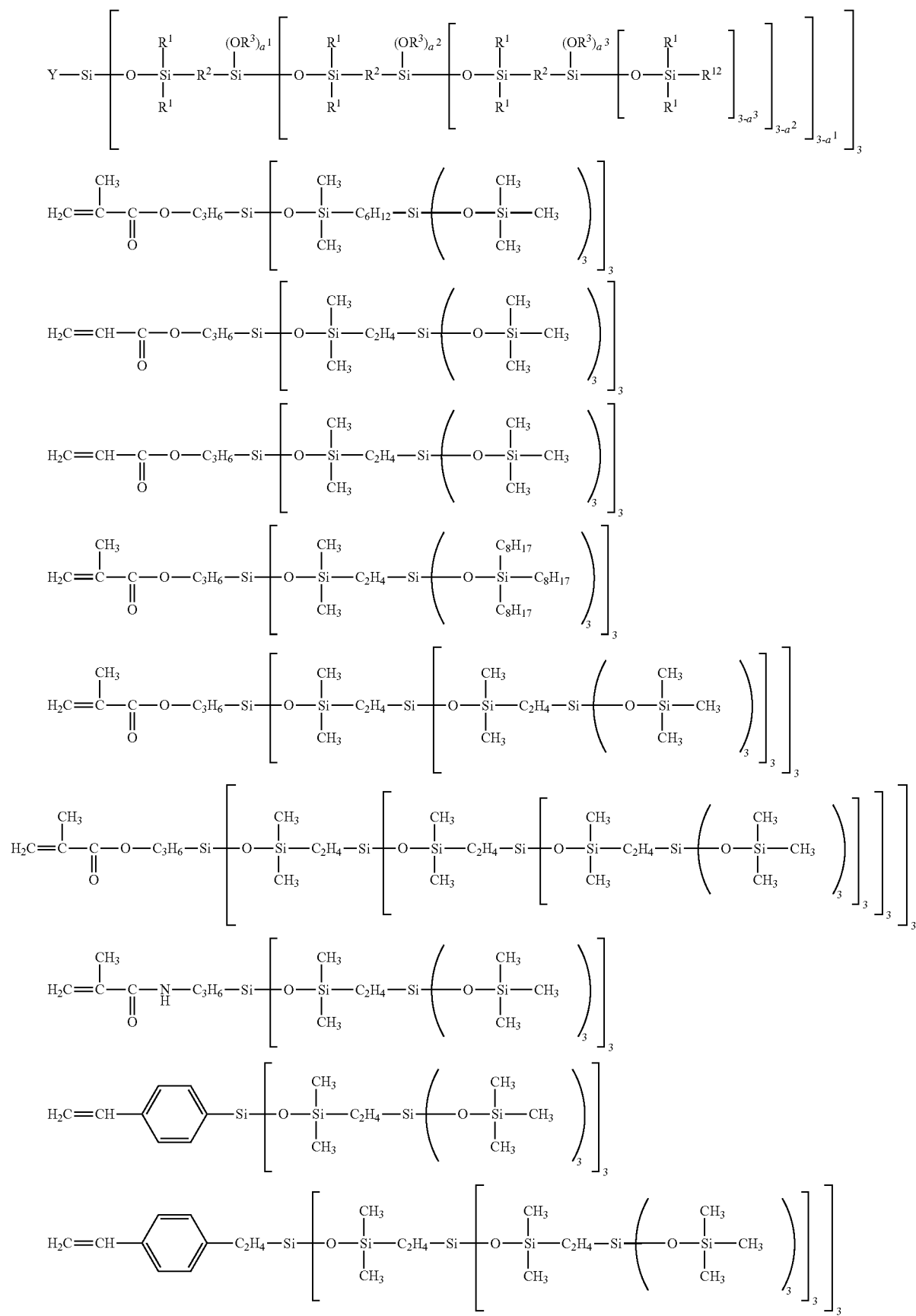

-continued

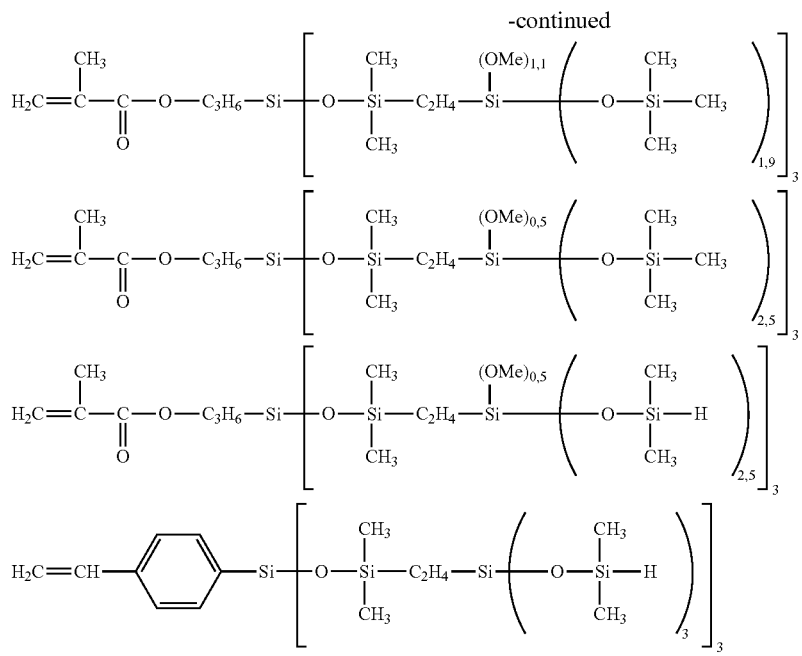

Thus, according to one embodiment, the carbosiloxane dendrimer of the composition according to the present invention is represented by the following formula:

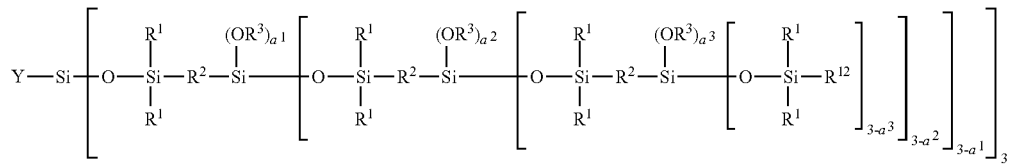

in which:

Y, $R^1$, $R^2$ and $R^3$ are as defined in formulae (I) and (II) above;

$a^1$, $a^2$ and $a^3$ correspond to the definition of $a^i$ according to formula (II); and $R^{12}$ is H, an aryl group containing from 5 to 10 carbon atoms or an alkyl group containing from 1 to 10 carbon atoms.

According to one embodiment, the carbosiloxane dendrimer of the composition according to the present invention is represented by one of the following formulae:

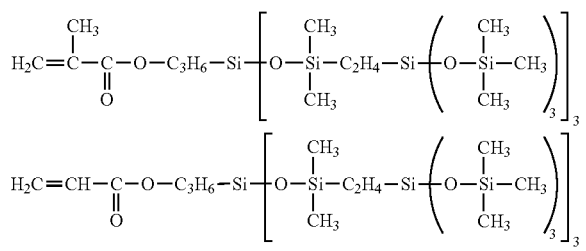

The vinyl polymer comprising the carbosiloxane dendrimer according to the invention may be manufactured according to the process for manufacturing a branched silalkylene siloxane described in Japanese patent application Hei 9-171 154.

For example, it may be produced by subjecting an organosilicon compound containing a hydrogen atom linked to a silicon atom, represented by the following general formula (IV):

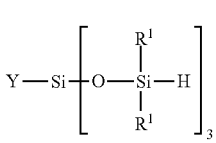

$R^1$ being as defined above in formula (I), and an organosilicon compound containing an alkenyl group, to a hydrosilylation reaction.

In the above formula, the organosilicon compound may be represented by 3-methacryloxypropyltris(dimethylsiloxy)silane, 3-acryloxypropyltris(dimethylsiloxy)silane and 4-vinylphenyltris(dimethylsiloxy)silane. The organosilicon compound that contains an alkenyl group may be represented by vinyltris(trimethylsiloxy)silane, vinyltris(dimethylphenylsiloxy)silane, and 5-hexenyltris(trimethylsiloxy)silane.

The hydrosilylation reaction is performed in the presence of a chloroplatinic acid, a complex of vinylsiloxane and of platinum, or a similar transition metal catalyst.

A vinyl polymer containing at least one carbosiloxane dendrimer-based unit may be chosen from polymers such that the carbosiloxane dendrimer-based unit is a carbosiloxane dendritic structure represented by formula (III):

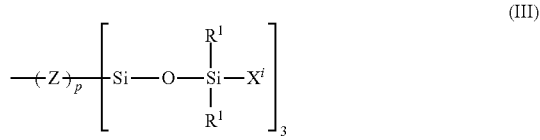

(III)

in which Z is a divalent organic group, "p" is 0 or 1, $R^1$ is as defined above in formula (IV) and $X^i$ is a silylalkyl group represented by formula (II) as defined above.

In a vinyl polymer containing at least one carbosiloxane dendrimer-based unit, the polymerization ratio between the components (A) and (B), in terms of the weight ratio between (A) and (B), is within a range from 0/100 to 99.9/0.1, or even from 0.1/99.9 to 99.9/0.1 and preferably within a range from 1/99 to 99/1. A ratio between the components (A) and (B) of 0/100 means that the compound becomes a homopolymer of component (B).

A vinyl polymer containing at least one carbosiloxane dendrimer-based unit may be obtained by copolymerization of the components (A) and (B), or by polymerization of the component (B) alone.

The polymerization may be a free-radical polymerization or an ionic polymerization, but free-radical polymerization is preferred.

The polymerization may be performed by bringing about a reaction between the components (A) and (B) in a solution for a period of from 3 to 20 hours in the presence of a radical initiator at a temperature of from 50° C. to 150° C.

A suitable solvent for this purpose is hexane, octane, decane, cyclohexane or a similar aliphatic hydrocarbon; benzene, toluene, xylene or a similar aromatic hydrocarbon; diethyl ether, dibutyl ether, tetrahydrofuran, dioxane or ethers; acetone, methyl ethyl ketone, methyl isobutyl ketone, diisobutyl ketone or similar ketones; methyl acetate, ethyl acetate, butyl acetate, isobutyl acetate or similar esters; methanol, ethanol, isopropanol, butanol or similar alcohols; octamethylcyclotetrasiloxane, decamethylcyclopentasiloxane, hexamethyldisiloxane, octamethyltrisiloxane or a similar organosiloxane oligomer.

A radical initiator may be any compound known in the art for standard free-radical polymerization reactions. The specific examples of such radical initiators are 2,2'-azobis (isobutyronitrile), 2,2'-azobis(2-methylbutyronitrile), 2,2'-azobis(2,4-dimethylvaleronitrile) or similar compounds of azobis type; benzoyl peroxide, lauroyl peroxide, tert-butyl peroxybenzoate, tert-butyl peroxy-2-ethylhexanoate or a similar organic peroxide. These radical initiators may be used alone or in a combination of two or more. The radical initiators may be used in an amount of from 0.1 to 5 parts by weight per 100 parts by weight of the components (A) and (B). A chain-transfer agent may be added. The chain-transfer agent may be 2-mercaptoethanol, butyl mercaptan, n-dodecyl mercaptan, 3-mercaptopropyltrimethoxysilane, a polydimethylsiloxane containing a mercaptopropyl group or a similar compound of mercapto type; methylene chloride, chloroform, carbon tetrachloride, butyl bromide, 3-chloropropyltrimethoxysilane or a similar halogenated compound.

In the manufacture of the polymer of vinyl type, after the polymerization, the unreacted residual vinyl monomer may be removed under conditions of heating under vacuum.

To facilitate the preparation of starting material for cosmetic products, the number-average molecular weight of the vinyl polymer containing a carbosiloxane dendrimer may be chosen within the range between 3000 and 2 000 000 and preferably between 5000 and 800 000. It may be a liquid, a gum, a paste, a solid, a powder, or any other form. The preferred forms are solutions consisting of the dilution of a dispersion or of a powder in solvents.

The vinyl polymer may be a dispersion of a polymer of vinyl type having a carbosiloxane dendrimer structure in its side molecular chain, in a liquid such as a silicone oil, an organic oil, an alcohol or water.

The silicone oil may be a dimethylpolysiloxane having the two molecular ends capped with trimethylsiloxy groups, a copolymer of methylphenylsiloxane and of dimethylsiloxane having the two molecular ends capped with trimethylsiloxy groups, a copolymer of methyl-3,3,3-trifluoropropylsiloxane and of dimethylsiloxane having the two molecular ends capped with trimethylsiloxy groups, or similar unreactive linear silicone oils, and also hexamethylcyclotrisiloxane, octamethylcyclotetrasiloxane, decamethylcyclopentasiloxane, dodecamethylcyclohexasiloxane or a similar cyclic compound. In addition to the unreactive silicone oils, modified polysiloxanes containing functional groups such as silanol groups, amino groups and polyether groups on the ends or within the molecular side chains may be used.

The organic oils may be isododecane, liquid paraffin, isoparaffin, hexyl laurate, isopropyl myristate, myristyl myristate, cetyl myristate, 2-octyldodecyl myristate; isopropyl palmitate, 2-ethylhexyl palmitate, butyl stearate, decyl oleate, 2-octyldodecyl oleate, myristyl lactate, cetyl lactate, lanolin acetate, stearyl alcohol, cetostearyl alcohol, oleyl alcohol, avocado oil, almond oil, olive oil, cocoa oil, jojoba oil, gum oil, sunflower oil, soybean oil, camellia oil, squalane, castor oil, cottonseed oil, coconut oil, egg yolk oil, polypropylene glycol monooleate, neopentyl glycol 2-ethylhexanoate or a similar glycol ester oil; triglyceryl isostearate, the triglyceride of a fatty acid of coconut oil, or a similar oil of a polyhydric alcohol ester; polyoxyethylene lauryl ether, polyoxypropylene cetyl ether or a similar polyoxyalkylene ether.

The alcohol may be any type that is suitable for use in combination with a cosmetic product starting material. For example, it may be methanol, ethanol, butanol, isopropanol or similar lower alcohols.

A solution or a dispersion of the alcohol should have a viscosity within the range from 10 to $10^9$ mPa at 25° C. To improve the sensory use properties in a cosmetic product, the viscosity should be within the range from 100 to $5\times10^8$ mPa·s.

The solutions and dispersions may be readily prepared by mixing a vinyl polymer containing at least one carbosiloxane dendrimer-based unit with a silicone oil, an organic oil, an alcohol or water. The liquids may be present in the polymerization step. In this case, the unreacted residual vinyl monomer should be completely removed by heat treatment of the solution or dispersion under atmospheric pressure or reduced pressure.

In the case of a dispersion, the dispersity of the polymer of vinyl type may be improved by adding a surfactant.

Such an agent may be hexylbenzenesulfonic acid, octylbenzenesulfonic acid, decylbenzenesulfonic acid, dodecylbenzenesulfonic acid, cetylbenzenesulfonic acid, myristylbenzenesulfonic acid or anionic surfactants of the sodium salts of these acids; octyltrimethylammonium hydroxide, dodecyltrimethylammonium hydroxide, hexadecyltrimethylammonium hydroxide, octyldimethylbenzylammonium hydroxide, decyldimethylbenzylammonium hydroxide, dioctadecyldimethylammonium hydroxide, beef tallow-trimethylammonium hydroxide, coconut oil-trimethylammonium hydroxide, or a similar cationic surfactant; a polyoxyalkylene alkyl ether, a polyoxyalkylenealkylphenol, polyoxyalkylene alkyl ester, the sorbitol ester of polyoxyalkylene, polyethylene glycol, polypropylene glycol, an ethylene oxide additive of diethylene glycol trimethylnonanol, and non-ionic surfactants of polyester type, and also mixtures.

In the dispersion, a mean particle diameter of the polymer of vinyl type may be within a range of between 0.001 and 100 microns and preferably between 0.01 and 50 microns. The reason for this is that, outside the recommended range, a cosmetic product mixed with the emulsion will not have a nice enough feel on the lips or to the touch, nor sufficient spreading properties nor a pleasant feel.

A vinyl polymer contained in the dispersion or the solution may have a concentration within a range of between 0.1% and 95% by weight and preferably between 5% and 85% by weight. However, to facilitate the handling and the preparation of the mixture, the range should preferably be between 10% and 75% by weight.

A vinyl polymer that is suitable for use in the invention may also be one of the polymers described in the examples of patent application EP 0 963 751.

According to one preferred embodiment, a vinyl polymer grafted with a carbosiloxane dendrimer may be the product of polymerization of:

(A1) from 0 to 99.9 parts by weight of one or more acrylate or methacrylate monomer(s); and (B1) from 100 to 0.1 parts by weight of an acrylate or methacrylate monomer of a tris[tri(trimethylsilyoxy)silylethyldimethylsiloxy]silylpropyl carbosiloxane dendrimer.

The monomers (A1) and (B1) correspond respectively to specific monomers (A) and (B).

According to one embodiment, a vinyl polymer containing at least one carbosiloxane dendrimer-based unit may comprise a tris[tri(trimethylsilyoxy)silylethyldimethylsiloxy] silylpropyl carbosiloxane dendrimer-based unit corresponding to one of the formulae:

The fluoro organic groups may be obtained by replacing with fluorine atoms all or some of the hydrogen atoms of methyl, ethyl, propyl, isopropyl, butyl, isobutyl, tert-butyl, pentyl, neopentyl, hexyl, cyclohexyl, heptyl, octyl, nonyl, decyl, undecyl, dodecyl, tridecyl, tetradecyl, hexadecyl and octadecyl groups and other alkyl groups of 1 to 20 carbon atoms, and also alkyloxyalkylene groups of 6 to 22 carbon atoms.

The groups represented by the formula $-(CH_2)_x-(CF_2)_y-R^{13}$ are suggested as examples of fluoroalkyl groups obtained by substituting fluorine atoms for hydrogen atoms of alkyl groups. In the formula, the index "x" is 0, 1, 2 or 3, and "y" is an integer from 1 to 20. $R^{13}$ is an atom or a group chosen from a hydrogen atom, a fluorine atom, $-(CH(CF_3)_2-$ or $CF(CF_3)_2$. Such fluorine-substituted alkyl groups are exemplified by linear or branched polyfluoroalkyl or perfluoroalkyl groups represented by the formulae shown below: $-CF_3$, $-C_2F_5$, $-nC_3F_7$, $-CF(CF_3)_2$, $-nC_4F_9$, $CF_2CF(CF_3)_2$, $-nC_5F_{11}$, $-nC_6F_{13}$, $-nC_8F_{17}$, $CH_2-CF_3$, $-(CH(CF_3)_2$, $CH_2CH(CF_3)_2-CH_2(CF_2)_2F$, $-CH_2(CF_2)_3F$, $-CH_2(CF_2)_4F$, $CH_2(CF_2)_6F$, $CH_2(CF_2)_8F$, $-CH_2CH_2CF_3$, $-CH_2CH_2(CF_2)_2F$, $-CH_2CH_2(CF_2)_3F$, $-CH_2CH_2(CF_2)_4F$, $-CH_2CH_2(CF_2)_6F$, $-CH_2-CH_2(CF_2)_8F$, $-CH_2-CH_2(CF_2)_{10}F$, $-CH_2CH_2(CF_2)_{12}F$, $CH_2CH_2(CF_2)_{14}F$, $-CH_2CH_2(CF_2)_{16}F$, $-CH_2CH_2CH_2CF_3$, $-CH_2CH_2CH_2(CF_2)_2F$, $-CH_2CH_2CH_2(CF_2)_2H$, $-CH_2(CF_2)_4H$ and $-CH_2CH_2(CF_2)_3H$.

The groups represented by $-CH_2CH_2-(CF_2)_m-CFR^{14}-[OCF_2CF(CF_3)]_n-OC_3F_7$ are suggested as fluoroalkyloxyfluoroalkylene groups obtained by substituting fluorine atoms for hydrogen atoms of alkyloxyalkylene groups. In the formula, the index "m" is 0 or 1, "n" is 0, 1, 2, 3, 4 or 5, and $R^{14}$ is a fluorine atom or $CF_3$. Such fluoroalkyloxyfluoroalkylene groups are exemplified by the perfluoroalkyloxyfluoroalkylene groups represented by the formulae shown below: $-CH_2CH_2CF(CF_3)-[OCF_2CF(CF_3)]_n-OC_3F_7$, $-CH_2CH_2CF_2CF_2-[OCF_2CF(CF_3)]_n-OC_3F_7$.

The number-average molecular weight of the vinyl polymer used in the present invention may be between 3000 and 2 000 000 and more preferably between 5000 and 800 000.

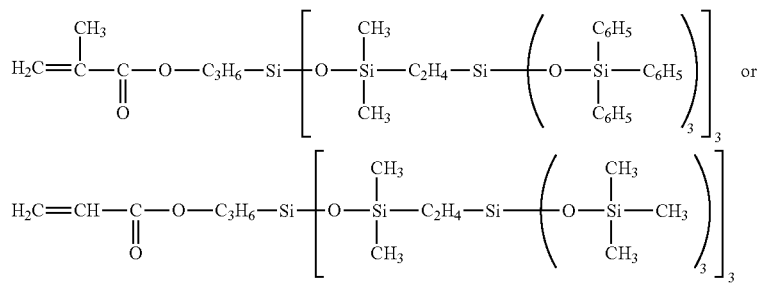

According to one preferred mode, a vinyl polymer containing at least one carbosiloxane dendrimer-based unit used in the invention comprises at least one butyl acrylate monomer.

According to one embodiment, a vinyl polymer may also comprise at least one fluoro organic group.

Structures in which the polymerized vinyl units constitute the backbone and carbosiloxane dendritic structures and also fluoro organic groups are attached to side chains are particularly preferred.

This type of fluorinated vinyl polymer may be obtained by addition:
of a vinyl monomer (M2) without a fluoro organic group, on a vinyl monomer (M1) containing fluoro organic groups, and
a carbosiloxane dendrimer (B) as defined above, of general formula (I) as defined above, by subjecting them to a copolymerization.

Thus, according to one embodiment, a composition of the invention may comprise a vinyl polymer which has at least one carbosiloxane dendrimer-based unit and which results from the copolymerization of a vinyl monomer (M1) as defined above, optionally of a vinyl monomer (M2) as defined above, and of a carbosiloxane dendrimer (B) as defined above, said vinyl polymer having a copolymerization ratio between the monomer (M1) and the monomer (M2) of 0.1 to 100:99.9 to 0% by weight, and a copolymerization ratio between the sum of the monomers (M1) and (M2) and the monomer (B) of 0.1 to 99.9:99.9 to 0.1% by weight.

The vinyl monomers (M1) containing fluoro organic groups in the molecule are preferably monomers represented by the general formula:

$$(CH_2)=CR^{15}COOR^f.$$

In this formula, $R^{15}$ is a hydrogen atom or a methyl group and $R^f$ is a fluoro organic group exemplified by the fluoroalkyl and fluoroalkyloxyfluoroalkylene groups described above. The compounds represented by the formulae presented below are suggested as specific examples of the component (M1). In the formulae presented below, "z" is an integer from 1 to 4.

$CH_2=CCH_3COO-CF_3$, $CH_2=CCH_3COO-C_2F_5$, $CH_2=CCH3COO-nC_3F_7$,
$CH_2=CCH_3COO-CF(CF_3)_2$, $CH_2=CCH_3COO-nC_4F_9$,
$CH_2=CCH_3COO-CF(CF_3)_2$, $CH_2=CCH_3COO-nC_5F_{11}$,
$CH_2=CCH_3COO-nC_6F_{13}$, $CH_2=CCH_3COO-nC_8F_{17}$, $CH_2=CCH_3COO-CH_2CF_3$,
$CH_2=CCH_3COO-CH(CF_3)_2$, $CH_2=CCH3COO-CH_2CH(CF_3)_2$,
$CH_2=CCH_3COO-CH_2(CF_2)_2F$, $CH_2=CCH_3COO-CH_2(CF_2)_2F$,
$CH_2=CCH_3COO-CH_2(CF_2)_4F$, $CH_2=CCH_3COO-CH_2(CF_2)_6F$,
$CH_2=CCH_3COO-CH_2(CF_2)_8F$, $CH_2=CCH_3COO-CH_2CH_2CF_3$,
$CH_2=CCH_3COO-CH_2CH_2(CF_2)_2F$,
$CH_2=CCH_3COO-CH_2CH_2(CF_2)_3F$,
$CH_2=CCH_3COO-CH_2CH_2(CF_2)_4F$,
$CH_2=CCH_3COO-CH_2CH_2(CF_2)_6F$,
$CH_2=CCH_3COO-CH_2CH_2(CF_2)_8F$,
$CH_2=CCH_3COO-CH_2CH_2(CF_2)_{10}F$,
$CH_2=CCH_3COO-CH_2CH_2(CF_2)_{12}F$, $CH_2=CCH_3COO-CH_2CH_2(CF_2)_{14}F$,
$CH_2=CCH_3COO-CH_2CH_2(CF_2)_{16}F$, $CH_2=CCH_3COO-CH_2CH_2CH_2CF_3$,
$CH_2=CCH_3COO-CH_2CH_2CH_2(CF_2)_2H$, $CH_2=CCH_3COO-CH_2(CF_2)_2H$,
$CH_2=CCH_3COO-CH_2(CF_2)_4F$, $CH_2=CCH_3COO-CH_2(CF_2)_3F$,
$CH_2=CCH_3COO-CH_2CH_2CF_3CF2-[OCF_2-CF(CF_3)]z-OC_3F_7$,
$CH_2=CCH_3COO-CH_2CH_2CF_2CF_2-[OCF_2-CF(CF_3)]z-OC_3F_7$,
$CH_2=CHCOO-CF_3$, $CH2=CHCOO-C_2F_5$, $CH_2=CHCOO-nC_3F_7$,
$CH_2=CHCOO-nC_3F_2$, $CH_2=CHCOO-nC_4F_9$, $CH_2=CHCOO-CH_2CF_3$,
$CH_2=CHCOO-nC_5F_{11}$, $CH_2=CHCOO-nC_6F_{13}$, $CH_2=CHCOO-nC_8F_{17}$,
$CH_2=CHCOO-CH_2CF_3$, $CH_2=CHCOO-CH(CF_3)_2$, $CH_2=CHCOO-CH_2CH(CF_3)_2$,
$CH_2=CHCOO-CH_2(CF_2)_2F$, $CH_2=CHCOO-CH_2(CF_2)_3F$,
$CH_2=CHCOO-CH_2(CF_2)_4F$, $CH_2=CHCOO-CH_2(CF_2)_6F$,
$CH_2=CHCOO-CH_2(CF_2)_8F$, $CH_2=CHCOO-CH_2CH_2CF_3$,
$CH_2=CHCOO-CH_2CH_2(CF_2)_2F$, $CH_2=CHCOO-CH_2CH_2(CF_2)_3F$,
$CH_2=CHCOO-CH_2CH_2(CF_2)_4F$, $CH_2=CHCOO-CH_2CH_2(CF_2)_6F$,
$CH_2=CHCOO-CH_2CH_2(CF_2)_8F$, $CH_2=HCOO-CH_2CH_2(CF_2)_{10}F$,
$CH_2=CHCOO-CH_2CH_2-(CF_2)_{12}F$,
$CH_2=CHCOO-CH_2CH_2(CF_2)_{14}F$,
$CH_2=CHCOO-CH_2CH_2(CF_2)_{16}F$, $CH_2=CHCOO-CH_2CH_2CH_2CF_3$,
$CH_2=CHCOO-CH_2CH_2CH_2(CF_2)_2F$, $CH_2=CHCOO-CH_2CH_2CH_2(CF_2)_2H$,
$CH_2=CHCOO-CH_2(CF_2)_4H$, $CH_2=CHCOO-CH_2CH_2(CF_2)_3H$,
$CH_2=CHCOO-CH_2CH_2CF(CF_3)-$, $[OCF_2-CF(CF_3)]_z-OC_3F_7$,
$CH_2=CHCOO-CH_2CH_2CF_2CF_2(CF_3)-[OCF_2-CF(CF_3)]_2-OC_3F_7$.

Among these, the vinyl polymers represented by the formulae presented below are preferable:

$CH_2=CHCOO-CH_2CH_2(CF_2)_6F$, $CH_2=CHCOO-CH_2CH_2(CF_2)_8F$,
$CH_2=CCH_3COO-CH_2CH_2(CF_2)_6F$, $CH_2=CCH_3COO-CH_2CH_2(CF_2)_4F$,
$CH_2=CHCOO-CH_2CF_3$, $CH_2=CCH_3COO-CH_2CF_3$.

The vinyl polymers represented by the formulae presented below are particularly preferable:

$CH_2=CHCOO-CH_2CF_3$, $CH_2=CCHCOO-CH_2CF_3$.

The vinyl monomers (M2) not containing any organofluorine groups in the molecule may be any monomers containing radical-polymerizable vinyl groups which are exemplified, for example, by methyl acrylate, methyl methacrylate, ethyl acrylate, ethyl methacrylate, n-propyl acrylate, n-propyl methacrylate, isopropyl acrylate, isopropyl methacrylate, and other lower alkyl acrylates or methacrylates; glycidyl acrylate, glycidyl methacrylate; n-butyl acrylate, n-butyl methacrylate, isobutyl acrylate, isobutyl methacrylate, tert-butyl acrylate, tert-butyl methacrylate, n-hexyl acrylate, n-hexyl methacrylate, cyclohexyl acrylate, cyclohexyl methacrylate, 2-ethylhexyl acrylate, 2-ethylhexyl methacrylate, octyl acrylate, octyl methacrylate, lauryl acrylate, lauryl methacrylate, stearyl acrylate, stearyl methacrylate, and other higher acrylates and methacrylates; vinyl acetate, vinyl propionate and other lower fatty acid vinyl esters; vinyl butyrate, vinyl caproate, vinyl 2-ethylhexanoate, vinyl laurate, vinyl stearate, and other higher fatty acid esters; styrene, vinyltoluene, benzyl acrylate, benzyl methacrylate, phenoxyethyl acrylate, phenoxyethyl methacrylate, vinylpyrrolidone, and other vinyl aromatic monomers; dimethylaminoethyl acrylate, dimethylaminoethyl methacrylate, diethylaminoethyl acrylate, diethylaminoethyl methacrylate, and other aminovinyl monomers, acrylamide, methacrylamide, N-methylolacrylamide, N-methylo lmethacrylamide, N-methoxymethylacrylamide, N-methoxymethylmethacrylamide, isobutoxymethoxyacrylamide, isobutoxymethoxymethacrylamide, N,N-dimethylacrylamide, N,N-dimethylmethacrylamide, and other vinylamide monomers; hydroxyethyl acrylate, hydroxyethyl methacrylate, acrylic acid hydroxypropyl alcohol, methacrylic acid hydroxypropyl alcohol, and other hydroxyvinyl monomers; acrylic acid, methacrylic acid, itaconic acid, crotonic acid, fumaric acid, maleic acid, and other vinylcarboxylic acid monomers; tetrahydrofurfuryl acrylate, tetrahydrofurfuryl methacrylate, butoxyethyl acrylate, butoxyethyl methacrylate, ethoxydiethylene glycol acrylate, ethoxydiethylene glycol methacrylate, polyethylene glycol acrylate, polyethylene glycol methacrylate, polypropylene glycol monoacrylate, polypropylene glycol monomethacrylate, hydroxybutyl vinyl ether, cetyl vinyl ether, 2-ethylhexyl vinyl ether, and other vinyl monomers containing an ether bond; acryloxypropyltrimethoxysilane, methacryloxypropyltrimethoxysilane, polydimethylsiloxanes containing acryl or methacryl groups at one of the ends, polydimethylsiloxanes containing alkenylaryl groups at one of the ends and other silicone compounds containing unsaturated groups; butadiene; vinyl chloride; vinylidene chloride, acrylonitrile, methacrylonitrile; dibutyl fumarate; maleic anhydride; dodecylsuccinic anhydride; acryl glycidyl ether, methacryl glycidyl ether, 3,4-epoxycyclohexylmethyl acrylate, 3,4-epoxycyclohexylmethyl methacrylate, alkali metal salts, ammonium salts and organic amine salts of acrylic acid, of methacrylic acid, of itaconic acid, of crotonic acid, of fumaric acid, of maleic acid and of other radical-polymerizable unsaturated carboxylic acids, radical-polymerizable unsaturated monomers containing sulfonic acid groups, such as styrene sulfonic acid and also the alkali metal salts thereof, the ammonium salts thereof and the organic amine salts thereof; the quaternary ammonium salts derived from acrylic acid or methacrylic acid, such as 2-hydroxy-3-methacryloxypropyltrimethylammonium chloride, methacrylic acid esters of a tertiary amine alcohol, such as the diethylamine ester of methacrylic acid and quaternary ammonium salts thereof.

In addition, it is also possible to use as vinyl monomers (M2) the polyfunctional vinyl monomers illustrated, for example, by trimethylolpropane triacrylate, trimethylolpropane trimethacrylate, pentaerythrityl triacrylate, pentaerythrityl trimethacrylate, ethylene glycol diacrylate, ethylene glycol dimethacrylate, tetraethylene glycol diacrylate, tetraethylene glycol dimethacrylate, polyethylene glycol diacrylate, polyethylene glycol dimethacrylate, 1,4-butanediol diacrylate, 1,4-butanediol dimethacrylate, 1,6-hexanediol diacrylate, 1,6-hexanediol dimethacrylate, neopentyl glycol diacrylate, neopentyl glycol dimethacrylate, trimethylolpropanetrioxyethyl acrylate, trimethylolpropanetrioxyethyl methacrylate, tris(2-hydroxyethyl)isocyanurate diacrylate, tris(2-hydroxyethyl)isocyanurate dimethacrylate, tris(2-hydroxyethyl)isocyanurate triacrylate, tris(2-hydroxyethyl)isocyanurate trimethacrylate, polydimethylsiloxane in which the two ends of the molecular chain are blocked with alkenylaryl groups, and other silicone compounds containing unsaturated groups.

As regards the ratio mentioned above in which (M1) and (M2) are copolymerized, the weight ratio between (M1) and (M2) is preferably within the range 1:99 to 100:0.

Y can be chosen, for example, from organic groups containing acrylic or methacrylic groups, organic groups containing an alkenylaryl group, or alkenyl groups containing from 2 to 10 carbon atoms.

The organic groups containing acrylic or methacrylic groups and the alkenylaryl groups are as defined above.

Among the compounds (B), mention may, for example, be made of the following compounds:

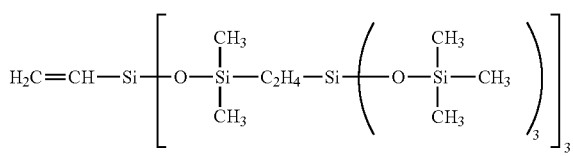

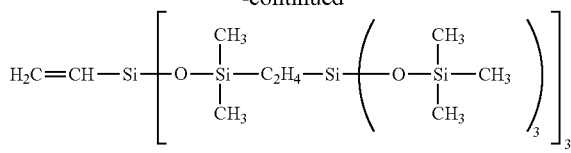

The carbosiloxane dendrimers (B) may be prepared using the process for preparing siloxane/silalkylene branched copolymers described in document EP 1 055 674.

For example, they may be prepared by subjecting organic alkenyl silicone compounds and silicone compounds comprising hydrogen atoms bonded to the silicon, represented by formula (IV) as defined above, to a hydrosilylation reaction.

The copolymerization ratio (by weight) between the monomer (B) and the monomers (M1) and (M2) is preferably within the range of 1:99 to 99:1 and even more preferably within the range of 5:95 to 95:5.

Amino groups may be introduced into the side chains of the vinyl polymer using, included in the component (M2), vinyl monomers containing amino groups, such as dimethylaminoethyl acrylate, dimethylaminoethyl methacrylate, diethylaminoethyl acrylate and diethylaminoethyl methacrylate, followed by performing a modification with potassium acetate monochloride, ammonium acetate monochloride, the aminomethylpropanol salt of monochloroacetic acid, the triethanolamine salt of monobromoacetic acid, sodium monochloropropionate, and other alkali metal salts of halogenated fatty acids; otherwise, carboxylic acid groups may be introduced into the side chains of the vinyl polymer using, included in the component (M2), vinyl monomers containing carboxylic acids, such as acrylic acid, methacrylic acid, itaconic acid, crotonic acid, fumaric acid and maleic acid, and the like, followed by neutralizing the product with triethylamine, diethylamine, triethanolamine and other amines.

A fluorinated vinyl polymer may be one of the polymers described in the examples of patent application WO 03/045 337.

According to one preferred embodiment, a vinyl polymer grafted in the sense of the present invention may be conveyed in an oil or a mixture of oils, which is/are preferably volatile, chosen in particular from silicone oils and hydrocarbon-based oils, and mixtures thereof.

According to one particular embodiment, a silicone oil that is suitable for use in the invention may be cyclopentasiloxane.

According to another particular embodiment, a hydrocarbon-based oil that is suitable for use in the invention may be isododecane.

Vinyl polymers grafted with at least one carbosiloxane dendrimer-based unit that may be particularly suitable for use in the present invention are the polymers sold under the names TIB 4-100, TIB 4-101, TIB 4-120, TIB 4-130, TIB 4-200, FA 4002 ID (TIB 4-202), TIB 4-220 and FA 4001 CM (TIB 4-230) by the company Dow Corning.

According to one embodiment, the composition according to the present invention comprises the vinyl polymer having at least one carbosiloxane dendrimer-based unit in an active material content of from 0.5% to 20%, in particular from 1% to 15%, more particularly from 1.5% to 10% and preferably from 3% to 5% by weight, relative to the total weight of said composition.

Film-Forming Block Ethylenic Copolymer

According to another embodiment of the invention, the composition comprises, as film-forming agent, at least one block ethylenic copolymer (also known as a block ethylenic polymer), in particular containing at least a first block with a glass transition temperature (Tg) of greater than or equal to 40° C. and being totally or partly derived from one or more first monomers, which are such that the homopolymer prepared from these monomers has a glass transition temperature of greater than or equal to 40° C., and at least a second block with a glass transition temperature of less than or equal to 20° C. and being derived totally or partly from one or more second monomers, which are such that the homopolymer prepared from these monomers has a glass transition temperature of less than or equal to 20° C., said first block and said second block being connected together via a random intermediate segment comprising at least one of said first constituent monomers of the first block and at least one of said second constituent monomers of the second block, and said block copolymer having a polydispersity index I of greater than 2.

The block polymer used according to the invention thus comprises at least one first block and at least one second block.

The term "at least one block" is intended to mean one or more blocks.

The term "block polymer" is intended to mean a polymer comprising at least two different blocks and preferably at least three different blocks.

The term "ethylenic polymer" is intended to mean a polymer obtained by polymerization of monomers comprising an ethylenic unsaturation.

The block ethylenic polymer used according to the invention is prepared exclusively from monofunctional monomers.

This means that the block ethylenic polymer used according to the present invention does not contain any multifunctional monomers, which make it possible to break the linearity of a polymer so as to obtain a branched or even crosslinked polymer, as a function of the content of multifunctional monomer. The polymer used according to the invention does not, either, contain any macromonomers (the term "macromonomer" is intended to mean a monofunctional monomer containing pendent groups of polymeric nature, and preferably having a molecular mass of greater than 500 g/mol, or alternatively a polymer comprising on only one of its ends a polymerizable (or ethylenically unsaturated) end group), which are used in the preparation of a grafted polymer.

It is pointed out that, in the text hereinabove and hereinbelow, the terms "first" and "second" blocks do not in any way condition the order of said blocks in the structure of the polymer.

The first block and the second block of the polymer used in the invention may be advantageously mutually incompatible.

The term "mutually incompatible blocks" is intended to mean that the mixture formed from a polymer corresponding to the first block and from a polymer corresponding to the second block is not miscible in the polymerization solvent that is in major amount by weight for the block polymer, at ambient temperature (25° C.) and atmospheric pressure ($10^5$ Pa), for a content of the mixture of said polymers of greater than or equal to 5% by weight, relative to the total weight of the mixture of said polymers and of said polymerization solvent, it being understood that:

i) said polymers are present in the mixture in a content such that the respective weight ratio ranges from 10/90 to 90/10, and that ii) each of the polymers corresponding to the first and second blocks has an average (weight-average or number-average) molecular weight equal to that of the block polymer ±15%.

In the case of a mixture of polymerization solvents, and in the event that two or more solvents are present in identical weight proportions, said polymer mixture is immiscible in at least one of them.

Needless to say, in the case of a polymerization performed in a single solvent, this solvent is the solvent that is in major amount.

The block polymer according to the invention comprises at least a first block and at least a second block that are connected together via an intermediate segment comprising at least one constituent monomer of the first block and at least one constituent monomer of the second block. The intermediate segment (also known as the intermediate block) has a glass transition temperature Tg that is between the glass transition temperatures of the first and second blocks.

The intermediate segment is a block comprising at least one constituent monomer of the first block and at least one constituent monomer of the second block of the polymer, and allows these blocks to be "compatibilized".

Advantageously, the intermediate segment comprising at least one constituent monomer of the first block and at least one constituent monomer of the second block of the polymer is a random polymer.

Preferably, the intermediate block is derived essentially from constituent monomers of the first block and of the second block.

The term "essentially" is intended to mean at least at 85%, preferably at least at 90%, better still at 95% and even better still at 100%.

The block polymer according to the invention is advantageously a film-forming block ethylenic polymer.

The term "ethylenic polymer" is intended to mean a polymer obtained by polymerization of monomers comprising an ethylenic unsaturation.

Preferentially, the polymer according to the invention does not comprise any silicon atoms in its backbone. The term "backbone" is intended to mean the main chain of the polymer, as opposed to the pendent side chains.

Preferably, the polymer according to the invention is not water-soluble, i.e. the polymer is not soluble in water or in a mixture of water and linear or branched lower monoalcohols containing from 2 to 5 carbon atoms, for instance ethanol, isopropanol or n-propanol, without modifying the pH, at an active material content of at least 1% by weight, at ambient temperature (25° C.).

Preferably, the polymer according to the invention is not an elastomer.

The term "non-elastomeric polymer" is intended to mean a polymer which, when it is subjected to a stress intended to pull it (for example by 30% relative to its initial length), does not return to a length substantially identical to its initial length when the stress ceases.

More specifically, the term "non-elastomeric polymer" denotes a polymer with an instantaneous recovery $R_i < 50\%$ and a delayed recovery $R_{2h} < 70\%$ after having been subjected to a 30% elongation. Preferably, $R_i < 30\%$ and $R_{2h} < 50\%$.

More specifically, the non-elastomeric nature of the polymer is determined according to the following protocol:

A polymer film is prepared by pouring a solution of the polymer in a Teflon-coated mould, followed by drying for 7 days in an environment conditioned at 23±5° C. and 50±10% relative humidity.

A film about 100 μm thick is thus obtained, from which are cut rectangular test specimens (for example using a punch) 15 mm wide and 80 mm long.

This sample is subjected to a tensile stress using a machine sold under the reference Zwick, under the same temperature and humidity conditions as for the drying.

The test specimens are pulled at a speed of 50 mm/min and the distance between the jaws is 50 mm, which corresponds to the initial length ($l_0$) of the test specimen.

The instantaneous recovery Ri is determined in the following manner:
the test specimen is pulled by 30% ($\varepsilon_{max}$), i.e. about 0.3 times its initial length ($l_0$),
the stress is released by applying a return speed equal to the tensile speed, i.e. 50 mm/min, and the residual elongation of the test specimen is measured as a percentage, after returning to zero stress load ($\varepsilon_i$).

The percentage instantaneous recovery ($R_i$) is given by the following formula:

$$R_i = ((\varepsilon_{max} - \varepsilon_i)/\varepsilon_{max}) \times 100$$

To determine the delayed recovery, the percentage residual elongation of the test specimen ($\varepsilon_{2h}$) is measured after 2 hours, 2 hours after returning to zero stress load.

The percentage delayed recovery ($R_{2h}$) is given by the following formula:

$$R_{2h} = ((\varepsilon_{max} - \varepsilon_{2h})/\square\varepsilon_{max}) \times 100$$

Purely by way of indication, a polymer according to one embodiment of the invention preferably has an instantaneous recovery $R_i$ of 10% and a delayed recovery $R_{2h}$ of 30%.

The polydispersity index of the polymer of the invention is greater than 2.

Advantageously, the block polymer used in the compositions according to the invention has a polydispersity index I of greater than 2, for example ranging from 2 to 9, preferably greater than or equal to 2.5, for example ranging from 2.5 to 8 and better still greater than or equal to 2.8, and in particular ranging from 2.8 to 6.

The polydispersity index I of the polymer is equal to the ratio of the weight-average mass Mw to the number-average mass Mn.

The weight-average molar mass (Mw) and number-average molar mass (Mn) are determined by gel permeation liquid chromatography (THF solvent, calibration curve established with linear polystyrene standards, refractometric detector).

The weight-average mass (Mw) of the polymer according to the invention is preferably less than or equal to 300 000; it ranges, for example, from 35 000 to 200 000 and better still from 45 000 to 150 000 g/mol.

The number-average mass (Mn) of the polymer according to the invention is preferably less than or equal to 70 000; it ranges, for example, from 10 000 to 60 000 and better still from 12 000 to 50 000 g/mol.

Preferably, the polydispersity index of the polymer according to the invention is greater than 2, for example ranging from 2 to 9, preferably greater than or equal to 2.5, for example ranging from 2.5 to 8, and better still greater than or equal to 2.8, and in particular ranging from 2.8 to 6.

First Block with a Tg of Greater than or Equal to 40° C.

The block with a Tg of greater than or equal to 40° C. has, for example, a Tg ranging from 40 to 150° C., preferably greater than or equal to 50° C., for example ranging from 50° C. to 120° C. and better still greater than or equal to 60° C., for example ranging from 60° C. to 120° C.

The glass transition temperatures indicated for the first and second blocks may be theoretical Tg values determined from the theoretical Tg values of the constituent monomers of each of the blocks, which may be found in a reference manual such as the Polymer Handbook, 3rd Edition, 1989, John Wiley, according to the following relationship, known as Fox's law:

$$1/Tg = \sum_i (\varpi_i / Tg_i)$$

$\varpi_i$ being the mass fraction of the monomer i in the block under consideration and $Tg_i$ being the glass transition temperature of the homopolymer of the monomer i.

Unless otherwise indicated, the Tg values indicated for the first and second blocks in the present patent application are theoretical Tg values.

The difference between the glass transition temperatures of the first and second blocks is generally greater than 10° C., preferably greater than 20° C. and better still greater than 30° C.

The block with a Tg of greater than or equal to 40° C. may be a homopolymer or a copolymer.

The block with a Tg of greater than or equal to 40° C. may be derived totally or partially from one or more monomers which are such that the homopolymer prepared from these monomers has a glass transition temperature of greater than or equal to 40° C. This block may also be referred to as a "rigid block".

In the case where this block is a homopolymer, it is derived from monomers which are such that the homopolymers prepared from these monomers have glass transition temperatures of greater than or equal to 40° C. This first block may be a homopolymer consisting of only one type of monomer (for which the Tg of the corresponding homopolymer is greater than or equal to 40° C.).

In the case where the first block is a copolymer, it may be totally or partially derived from one or more monomers, the nature and concentration of which are chosen such that the Tg of the resulting copolymer is greater than or equal to 40° C.

The copolymer may comprise, for example:
monomers which are such that the homopolymers prepared from these monomers have Tg values of greater than or equal to 40° C., for example a Tg ranging from 40° C. to 150° C., preferably greater than or equal to 50° C., for example ranging from 50° C. to 120° C. and better still greater than or equal to 60° C., for example ranging from 60° C. to 120° C., and
monomers which are such that the homopolymers prepared from these monomers have Tg values of less than 40° C., chosen from monomers with a Tg of between 20° C. and 40° C. and/or monomers with a Tg of less than or equal to 20° C., for example a Tg ranging from −100° C. to 20° C., preferably less than 15° C., in particular ranging from −80° C. to 15° C. and better still less than 10° C., for example ranging from −50° C. to 0° C., as described later.

The first monomers of which the homopolymers have a glass transition temperature of greater than or equal to 40° C. are chosen, preferably, from the following monomers, also known as the main monomers:

the methacrylates of formula $CH_2=C(CH_3)-COOR_1$ in which $R_1$ represents a linear or branched unsubstituted alkyl group containing from 1 to 4 carbon atoms, such as a methyl, ethyl, propyl or isobutyl group, or R, represents a $C_4$ to $C_{12}$ cycloalkyl group, preferably a $C_8$ to $C_{12}$ cycloalkyl, such as isobornyl methacrylate, the acrylates of formula $CH_2=CH-COOR_2$ in which $R_2$ represents a $C_4$ to $C_{12}$ cycloalkyl group such as an isobornyl group or a tert-butyl group, (meth)acrylamides of formula:

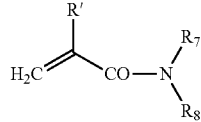

in which $R_7$ and $R_8$, which may be identical or different, each represent a hydrogen atom or a linear or branched $C_1$ to $C_{12}$ alkyl group such as an n-butyl, t-butyl, isopropyl, isohexyl, isooctyl or isononyl group; or $R_7$ represents H and $R_8$ represents a 1,1-dimethyl-3-oxobutyl group, and R' denotes H or methyl. Examples of monomers that may be mentioned include N-butylacrylamide, N-tert-butylacrylamide, N-isopropylacrylamide, N,N-dimethylacrylamide and N,N-dibutylacrylamide, and mixtures thereof.

The first block is advantageously obtained from at least one acrylate monomer of formula $CH_2=CH-COOR_2$ and from at least one methacrylate monomer of formula $CH_2=C(CH_3)-COOR_2$ in which $R_2$ represents a $C_4$ to $C_{12}$ cycloalkyl group, preferably a $C_8$ to $C_{12}$ cycloalkyl, such as isobornyl. The monomers and the proportions thereof are preferably chosen such that the glass transition temperature of the first block is greater than or equal to 40° C.

According to one embodiment, the first block is obtained from:

i) at least one acrylate monomer of formula $CH_2=CH-COOR_2$ in which $R_2$ represents a $C_4$ to $C_{12}$ cycloalkyl group, preferably a $C_8$ to $C_{12}$ cycloalkyl group, such as isobornyl,
ii) and at least one methacrylate monomer of formula $CH2=C(CH_3)-COOR'_2$ in which $R'_2$ represents a $C_4$ to $C_{12}$ cycloalkyl group, preferably a $C_8$ to $C_{12}$ cycloalkyl group, such as isobornyl.

According to one embodiment, the first block is obtained from at least one acrylate monomer of formula $CH_2=CH-COOR_2$ in which $R_2$ represents a $C_8$ to $C_{12}$ cycloalkyl group, such as isobornyl, and from at least one methacrylate monomer of formula $CH_2=C(CH_3)-COOR'_2$ in which $R'_2$ represents a $C_8$ to $C_{12}$ cycloalkyl group, such as isobornyl.

Preferably, $R_2$ and $R'_2$ represent, independently or simultaneously, an isobornyl group.

Preferably, the block copolymer comprises from 50% to 80% by weight of isobornyl methacrylate/acrylate, from 10% to 30% by weight of isobutyl acrylate and from 2% to 10% by weight of acrylic acid.

The first block may be obtained exclusively from said acrylate monomer and from said methacrylate monomer.

The acrylate monomer and the methacrylate monomer are preferably in mass proportions of between 30/70 and 70/30, preferably between 40/60 and 60/40 and in particular of the order of 50/50.

The proportion of the first block advantageously ranges from 20% to 90% by weight of the polymer, better still from 30% to 80% and even better still from 60% to 80%.

According to one embodiment, the first block is obtained by polymerization of isobornyl methacrylate and isobornyl acrylate.

Second Block with a Glass Transition Temperature of Less than 20° C.

The second block advantageously has a glass transition temperature Tg of less than or equal to 20° C., for example, a Tg ranging from –100° C. to 20° C., preferably less than or equal to 15° C., in particular ranging from –80° C. to 15° C. and better still less than or equal to 10° C., for example ranging from –100° C. to 10° C., in particular ranging from –30° C. to 10° C.

The second block is totally or partially derived from one or more second monomers, which are such that the homopolymer prepared from these monomers has a glass transition temperature of less than or equal to 20° C.

This block may also be referred to as a "flexible block".

The monomer with a Tg of less than or equal to 20° C. (known as the second monomer) is preferably chosen from the following monomers:

the acrylates of formula $CH_2=CHCOOR_3$,
  $R_3$ representing a linear or branched, unsubstituted $C_1$ to $C_{12}$ alkyl group, with the exception of the tert-butyl group, in which one or more heteroatoms chosen from O, N and S are optionally intercalated,
the methacrylates of formula $CH_2=C(CH_3)-COOR_4$,
  $R_4$ representing a linear or branched, unsubstituted $C_6$ to $C_{12}$ alkyl group, in which one or more heteroatoms chosen from O, N and S are optionally intercalated;
the vinyl esters of formula $R_5-COO-CH=CH_2$,
  in which $R_5$ represents a linear or branched $C_4$ to $C_{12}$ alkyl group;
ethers of vinyl alcohol and of a $C_4$ to $C_{12}$ alcohol,
N—($C_4$ to $C_{12}$)alkyl acrylamides, such as N-octylacrylamide,
and mixtures thereof.

The preferred monomers with a Tg of less than or equal to 20° C. are isobutyl acrylate, 2-ethylhexyl acrylate or mixtures thereof in all proportions.

Each of the first and second blocks may contain in small proportion at least one constituent monomer of the other block.

Thus, the first block may contain at least one constituent monomer of the second block, and vice versa.

Each of the first and/or second blocks may comprise, in addition to the monomers indicated above, one or more other monomers known as additional monomers, which are different from the main monomers mentioned above.

The nature and amount of this or these additional monomer(s) are chosen such that the block in which they are present has the desired glass transition temperature.

This additional monomer is chosen, for example, from:
ethylenically unsaturated monomers comprising at least one tertiary amine function, for instance 2-vinylpyridine, 4-vinylpyridine, dimethylaminoethyl methacrylate, diethylaminoethyl methacrylate and dimethylaminopropylmethacrylamide, and salts thereof,
the methacrylates of formula $CH_2=C(CH_3)-COOR_6$,
  in which $R_6$ represents a linear or branched alkyl group containing from 1 to 4 carbon atoms, such as a methyl, ethyl, propyl or isobutyl group, said alkyl group being substituted with one or more substituents chosen from hydroxyl groups (for instance 2-hydroxypropyl methacrylate and 2-hydroxyethyl methacrylate) and halogen atoms (Cl, Br, I or F), such as trifluoroethyl methacrylate, the methacrylates of formula $CH_2\!=\!C(CH_3)\!-\!COOR_9$, $R_9$ representing a linear or branched $C_6$ to $C_{12}$ alkyl group in which one or more heteroatoms chosen from O, N and S are optionally intercalated, said alkyl group being substituted with one or more substituents chosen from hydroxyl groups and halogen atoms (Cl, Br, I or F);

acrylates of formula $CH_2\!=\!CHCOOR_{10}$, $R_{10}$ representing a linear or branched $C_1$ to $C_{12}$ alkyl group substituted with one or more substituents chosen from hydroxyl groups and halogen atoms (Cl, Br, I or F), such as 2-hydroxypropyl acrylate and 2-hydroxyethyl acrylate, or $R_{10}$ represents a $C_1$ to $C_{12}$ alkyl-O-POE (polyoxyethylene) with repetition of the oxyethylene unit 5 to 10 times, for example methoxy-POE, or $R_{10}$ represents a polyoxyethylenated group comprising from 5 to 10 ethylene oxide units.

In particular, the first block may comprise as additional monomer:

(meth)acrylic acid, preferably acrylic acid,
tert-butyl acrylate,
the methacrylates of formula $CH_2\!=\!C(CH_3)\!-\!COOR_1$,
    in which $R_1$ represents a linear or branched unsubstituted alkyl group containing from 1 to 4 carbon atoms, such as a methyl, ethyl, propyl or isobutyl group,
(meth)acrylamides of formula:

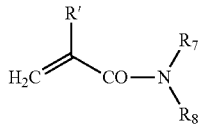

in which $R_7$ and $R_8$, which may be identical or different, each represent a hydrogen atom or a linear or branched $C_1$ to $C_{12}$ alkyl group such as an n-butyl, t-butyl, isopropyl, isohexyl, isooctyl or isononyl group; or $R_7$ represents H and $R_8$ represents a 1,1-dimethyl-3-oxobutyl group, and R' denotes H or methyl.

Examples of monomers that may be mentioned include N-butylacrylamide, N-tert-butylacrylamide, N-isopropylacrylamide, N,N-dimethylacrylamide and N,N-dibutylacrylamide, and mixtures thereof.

Preferably, the additional monomer is acrylic acid.

The additional monomer may represent 0.5% to 30% by weight relative to the weight of the polymer. According to one embodiment, the polymer of the invention does not contain any additional monomer.

Preferably, the polymer of the invention comprises at least isobornyl acrylate and isobornyl methacrylate monomers in the first block and isobutyl acrylate and acrylic acid monomers in the second block.

Preferably, the polymer comprises at least isobornyl acrylate and isobornyl methacrylate monomers in equivalent weight proportion in the first block and isobutyl acrylate and acrylic acid monomers in the second block.

Preferably, the polymer comprises at least isobornyl acrylate and isobornyl methacrylate monomers in equivalent weight proportion in the first block, and isobutyl acrylate and acrylic acid monomers in the second block, the first block representing 70% by weight of the polymer.

Preferably, the polymer comprises at least isobornyl acrylate and isobornyl methacrylate monomers in equivalent weight proportion in the first block and isobutyl acrylate and acrylic acid monomers in the second block. Preferably, the block with a Tg of greater than 40° C. represents 70% by weight of the polymer, and acrylic acid represents 5% by weight of the polymer.

According to one embodiment, the first block does not comprise any additional monomer.

According to one preferred embodiment, the second block comprises acrylic acid as additional monomer. In particular, the second block is advantageously obtained from an acrylic acid monomer and from at least one other monomer with a Tg of less than or equal to 20° C.

According to one preferred embodiment, the invention relates to a cosmetic composition for making up and/or caring for keratin materials, comprising, in a physiologically acceptable medium, at least one copolymer comprising at least one acrylate monomer of formula $CH_2\!=\!CH\!-\!COOR_2$, in which $R_2$ represents a $C_8$ to $C_{12}$ cycloalkyl group and/or at least one methacrylate monomer of formula $CH_2\!=\!C(CH_3)\!-\!COOR'_2$, in which $R'_2$ represents a $C_8$ to $C_{12}$ cycloalkyl group, at least one second acrylate monomer of formula $CH_2\!=\!CHCOOR_3$, in which $R_3$ represents a linear or branched, unsubstituted $C_1$ to $C_{12}$ alkyl group, with the exception of the tert-butyl group, and at least one acrylic acid monomer, said composition also comprising, in particular, at least one non-volatile hydrocarbon-based ester oil comprising at least 16 carbon atoms and having a molar mass of less than 650 g/mol, and said composition comprising less than 10% by weight of volatile oil of which the flash point is less than or equal to 80° C., relative to the total weight of the composition.

Preferably, the copolymer used in the compositions according to the invention is obtained from at least one isobornyl methacrylate monomer, at least one isobornyl acrylate monomer, at least one isobutyl acrylate monomer and at least one acrylic acid monomer.

Preferably, the copolymer used in the invention comprises from 50% to 80% by weight of isobornyl methacrylate/acrylate mixture, from 10% to 30% by weight of isobutyl acrylate and from 2% to 10% by weight of acrylic acid.

The block copolymer may advantageously comprise more than 2% by weight of acrylic acid monomers, and in particular from 2% to 15% by weight, for example from 3% to 15% by weight, in particular from 4% to 15% by weight or even from 4% to 10% by weight of acrylic acid monomers, relative to the total weight of said copolymer.

The constituent monomers of the second block and the proportions thereof are chosen such that the glass transition temperature of the second block is less than or equal to 20° C.

Intermediate Segment

The intermediate segment (also known as the intermediate block) connects the first block and the second block of the polymer used according to the present invention. The intermediate segment results from the polymerization:

i) of the first monomer(s), and optionally of the additional monomer(s), which remain available after their polymerization to a maximum degree of conversion of 90% to form the first block, ii) and of the second monomer(s), and optionally of the additional monomer(s), added to the reaction mixture.

The formation of the second block is initiated when the first monomers no longer react or are no longer incorporated into the polymer chain either because they are all consumed or because their reactivity no longer allows them to be.

Thus, the intermediate segment comprises the first available monomers, resulting from a degree of conversion of these first monomers of less than or equal to 90%, during the introduction of the second monomer(s) during the synthesis of the polymer.

The intermediate segment of the block polymer is a random polymer (which may also be referred to as a random block). This means that it comprises a random distribution of the first monomer(s) and of the second monomer(s) and also of the additional monomer(s) optionally present.

Thus, the intermediate segment is a random block, as are the first block and the second block if they are not homopolymers (i.e. if they are both formed from at least two different monomers).

Process for Preparing the Copolymer

The block ethylenic copolymer according to the invention is prepared by free radical polymerization, according to the techniques that are well known for this type of polymerization.

The free radical polymerization is performed in the presence of an initiator, the nature of which is adapted, in a known manner, as a function of the desired polymerization temperature and of the polymerization solvent. In particular, the initiator may be chosen from initiators bearing a peroxide function, redox couples or other free radical polymerization initiators known to those skilled in the art.

In particular, examples of initiators bearing a peroxide function that may be mentioned include:
a. peroxyesters such as tert-butyl peroxyacetate, tert-butyl perbenzoate, tert-butyl peroxy-2-ethylhexanoate (Trigonox 21S from Akzo Nobel) or 2,5-bis (2-ethylhexanoylperoxy)-2,5-dimethylhexane (Trigonox 141 from Akzo Nobel);
b. peroxydicarbonates such as diisopropyl peroxydicarbonate;
c. peroxy ketones such as methyl ethyl ketone peroxide;
d. hydroperoxides such as aqueous hydrogen peroxide solution ($H_2O_2$) or tert-butyl hydroperoxide;
e. diacyl peroxides such as acetyl peroxide or benzoyl peroxide;
f. dialkyl peroxides such as di-tert-butyl peroxide;
g. inorganic peroxides such as potassium peroxodisulfate ($K_2S_2O_8$).

As initiator in the form of a redox couple, mention may be made of the potassium thiosulfate+potassium peroxodisulfate couple, for example.

According to one preferred embodiment, the initiator is chosen from organic peroxides comprising from 8 to 30 carbon atoms. Preferably, the initiator used is 2,5-bis(2-ethylhexanoylperoxy)-2,5-dimethylhexane sold under the reference Trigonox® 141 by the company Akzo Nobel.

The block copolymer used according to the invention is prepared by free radical polymerization and not by controlled or living polymerization. In particular, the polymerization of the block ethylenic copolymer is performed in the absence of control agents, and in particular in the absence of control agents conventionally used in living or controlled polymerization processes, such as nitroxides, alkoxyamines, dithioesters, dithiocarbamates, dithiocarbonates or xanthates, trithiocarbonates or copper-based catalysts, for example.

As mentioned previously, the intermediate segment is a random block, as are the first block and the second block if they are not homopolymers (i.e. if they are both formed from at least two different monomers).

The block copolymer may be prepared by free radical polymerization, and in particular by a process that consists in mixing, in the same reactor, a polymerization solvent, an initiator, at least one monomer with a glass transition temperature of greater than or equal to 40° C., and at least one monomer with a glass transition temperature of less than or equal to 20° C., according to the following sequence:
some of the polymerization solvent and optionally some of the initiator and of the monomers for the first addition are poured into the reactor, and the mixture is heated to a reaction temperature of between 60° C. and 120° C.,
said at least one first monomer with a Tg of greater than or equal to 40° C. and optionally some of the initiator are then poured in, in a first addition, and the mixture is left to react for a time T corresponding to a maximum degree of conversion of said monomers of 90%,
further polymerization initiator and said at least one second monomer with a glass transition temperature of less than or equal to 20° C. are then poured into the reactor, in a second addition, and the mixture is left to react for a time T' after which the degree of conversion of said monomers reaches a plateau,
the reaction mixture is brought back to ambient temperature.

Preferably, the copolymer may be prepared by free radical polymerization, in particular by a process that consists in mixing, in the same reactor, a polymerization solvent, an initiator, an additional monomer, in particular acrylic acid, at least one monomer with a glass transition temperature of less than or equal to 20° C., at least one acrylate monomer of formula $CH_2=CH-COOR_2$ in which $R_2$ represents a $C_4$ to $C_{12}$ cycloalkyl group and at least one methacrylate monomer of formula $CH_2=C(CH_3)-COOR'_2$ in which $R'_2$ represents a $C_4$ to $C_{12}$ cycloalkyl group, according to the following sequence of steps:
some of the polymerization solvent and optionally some of the initiator and of the monomers for the first addition are poured into the reactor, and the mixture is heated to a reaction temperature of between 60° C. and 120° C.,
said at least one acrylate monomer of formula $CH_2=CH-COOR_2$ and said at least one methacrylate monomer of formula $CH_2=C(CH_3)-COOR'_2$, as monomers with a Tg of greater than or equal to 40° C., and optionally some of the initiator, are then poured in, in a first addition, and the mixture is left to react for a time T corresponding to a maximum degree of conversion of said monomers of 90%,
further polymerization initiator, the acrylic acid monomer and said at least one monomer with a glass transition temperature of less than or equal to 20° C. are then poured into the reactor, in a second addition, and the mixture is left to react for a time T' after which the degree of conversion of said monomers reaches a plateau,
the reaction mixture is brought back to ambient temperature.

The term "polymerization solvent" is intended to mean a solvent or a mixture of solvents. In particular, as polymerization solvents that may be used, mention may be made of:
ketones that are liquid at ambient temperature, such as methyl ethyl ketone, methyl isobutyl ketone, diisobutyl ketone, isophorone, cyclohexanone or acetone;
propylene glycol ethers that are liquid at ambient temperature, such as propylene glycol monomethyl ether, propylene glycol monomethyl ether acetate or dipropylene glycol n-butyl monoether;
short-chain esters (containing from 3 to 8 carbon atoms in total), such as ethyl acetate, methyl acetate, propyl acetate, n-butyl acetate or isopentyl acetate;
ethers that are liquid at ambient temperature, such as diethyl ether, dimethyl ether or dichlorodiethyl ether;
alkanes that are liquid at ambient temperature, such as decane, heptane, dodecane, isododecane, cyclohexane or isohexadecane;
aromatic cyclic compounds that are liquid at ambient temperature, such as toluene and xylene; aldehydes that are liquid at ambient temperature, such as benzaldehyde and acetaldehyde, and mixtures thereof.

Conventionally, the polymerization solvent is a volatile oil with a flash point of less than 80° C. The flash point is measured in particular according to standard ISO 3679.

The polymerization solvent may be chosen in particular from ethyl acetate, butyl acetate, alcohols such as isopropanol or ethanol, and aliphatic alkanes such as isododecane, and mixtures thereof. Preferably, the polymerization solvent is a mixture of butyl acetate and isopropanol or isododecane.

According to another embodiment, the copolymer may be prepared by free radical polymerization according to a preparation process that consists in mixing, in the same reactor, a polymerization solvent, an initiator, at least one monomer with a glass transition temperature of less than or equal to 20° C. and at least one monomer with a Tg of greater than or equal to 40° C., according to the following sequence of steps:
  some of the polymerization solvent and optionally some of the initiator and of the monomers for the first addition are poured into the reactor, and the mixture is heated to a reaction temperature of between 60° C. and 120° C.,
  said at least one monomer with a glass transition temperature of less than or equal to 20° C. and optionally some of the initiator are then poured in, in a first addition, and the mixture is left to react for a time T corresponding to a maximum degree of conversion of said monomers of 90%,
  further polymerization initiator and said at least one monomer with a Tg of greater than or equal to 40° C. are then poured into the reactor, in a second addition, and the mixture is left to react for a time T' after which the degree of conversion of said monomers reaches a plateau,
  the reaction mixture is brought back to ambient temperature.

According to one preferred embodiment, the copolymer may be prepared by free radical polymerization according to a preparation process that consists in mixing, in the same reactor, a polymerization solvent, an initiator, an acrylic acid monomer, at least one monomer with a glass transition temperature of less than or equal to 20° C., at least one monomer with a Tg of greater than or equal to 40° C., and in particular, as monomers with a Tg of greater than or equal to 40° C., at least one acrylate monomer of formula $CH_2$=CH—$COOR_2$ in which $R_2$ represents a $C_4$ to $C_{12}$ cycloalkyl group and at least one methacrylate monomer of formula $CH_2$=C($CH_3$)—COOR' in which $R'_2$ represents a $C_4$ to $C_{12}$ cycloalkyl group, according to the following sequence of steps:
  some of the polymerization solvent and optionally some of the initiator and of the monomers for the first addition are poured into the reactor, and the mixture is heated to a reaction temperature of between 60° C. and 120° C.,
  the acrylic acid monomer and said at least one monomer with a glass transition temperature of less than or equal to 20° C. and optionally some of the initiator are then poured in, in a first addition, and the mixture is left to react for a time T corresponding to a maximum degree of conversion of said monomers of 90%,
  further polymerization initiator, said at least one acrylate monomer of formula $CH_2$=CH—$COOR_2$ and said at least one methacrylate monomer of formula $CH_2$=C($CH_3$)—$COOR'_2$, as monomer with a Tg of greater than or equal to 40° C., are then poured into the reactor, in a second addition, and the mixture is left to react for a time T' after which the degree of conversion of said monomers reaches a plateau,
  the reaction mixture is brought back to ambient temperature.

The polymerization temperature is preferably about 90° C.

The reaction time after the second addition is preferably between 3 and 6 hours.

Alkylcelluloses

The appropriate alkylcelluloses that can be used in the context of the invention are more particularly those of which the alkyl residue comprises between 1 and 6 carbon atoms, preferably between 2 and 6 carbon atoms, even more preferably between 2 and 3 carbon atoms, and better still ethylcellulose.

The alkylcellulose is more particularly a cellulose alkyl ether comprising a chain consisting of β-anhydroglucose units linked together via acetal bonds. Each anhydroglucose unit contains three replaceable hydroxyl groups, all or some of these hydroxyl groups being able to react according to the following reaction:

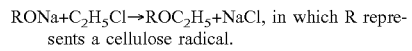
RONa+$C_2H_5$Cl→RO$C_2H_5$+NaCl, in which R represents a cellulose radical.

Total substitution of the three hydroxyl groups would lead, for each anhydroglucose unit, to a degree of substitution of 3, in other words to a content of alkoxy groups of 54.88%.

The ethylcellulose polymers used in a cosmetic composition according to the invention are preferentially polymers with a degree of substitution with ethoxy groups ranging from 2.5 to 2.6 per anhydroglucose unit, in other words comprising a content of ethoxy groups ranging from 44% 20 to 50%.

Silicone Resins

More generally, the term "resin" is intended to mean a compound of which the structure is three-dimensional. "Silicone resins" are also referred to as "siloxane resins". Thus, for the purposes of the present invention, a polydimethylsiloxane is not a silicone resin.

The nomenclature of silicone resins (also known as siloxane resins) is known under the name "MDTQ", the resin being described as a function of the various siloxane monomer units it comprises, each of the letters "MDTQ" characterizing a type of unit. Such resins are described, for example, in the *Encyclopedia of Polymer Science and Engineering*, vol. 15, John Wiley and Sons, New York, (1989), pp. 265-270, and U.S. Pat. No. 2,676,182, U.S. Pat. No. 3,627,851, U.S. Pat. No. 3,772,247, U.S. Pat. No. 5,248,739 or U.S. Pat. No. 5,082,706, U.S. Pat. No. 5,319,040, U.S. Pat. No. 5,302,685 and U.S. Pat. No. 4,935,484.

The appropriate resins are more particularly MQ resins.

The letter "M" represents the monofunctional unit of formula R1R2R3SiO$_{1/2}$, the silicon atom being bonded to only one oxygen atom in the polymer comprising this unit.

The letter "D" means a difunctional unit R1R2SiO$_{2/2}$ in which the silicon atom is bonded to two oxygen atoms.

The letter "T" represents a trifunctional unit of formula R1SiO$_{3/2}$.

In the unit M defined previously, R represents a hydrocarbon-based (in particular alkyl) radical containing from 1 to 10 carbon atoms, a phenyl group, a phenylalkyl group or a hydroxyl group.

Finally, the letter "Q" means a tetrafunctional unit SiO$_{4/2}$ in which the silicon atom is bonded to four oxygen atoms, which are themselves bonded to the rest of the polymer.

Various silicone resins with different properties may be obtained from these different units, the properties of these polymers varying as a function of the type of monomer (or unit), the nature and number of the radical R, the length of the polymer chain, the degree of branching and the size of the pendent chains.

As silicone resins that may be used in the compositions according to the invention, use may be made, for example, of silicone resins of MQ type, of T type or of MQT type.

By way of example of silicone resins of MQ type, mention may be made of:
  alkyl siloxysilicates of formula [(R1)$_3$SiO$_{1/2}$]$_x$(SiO$_{4/2}$)$_y$ (MQ units) in which x and y are integers ranging from 50 to 80, and such that the group R1 represents a radical as defined previously, and is preferably an alkyl group containing from 1 to 8 carbon atoms, preferably a methyl group;
  as examples of solid silicone resins of MQ type of trimethyl siloxysilicate type, mention may be made of those sold under the reference SR1000 by the company General Electric, under the reference TMS 803 by the company Wacker, or under the name KF-7312J by the company Shin-Etsu or DC 749 or DC 593 by the company Dow Corning;
  as silicone resins comprising MQ siloxysilicate units, mention may also be made of phenylalkylsiloxysilicate resins, such as phenylpropyldimethylsiloxysilicate (Silshine 151 sold by the company General Electric). The preparation of such resins is described in particular in patent U.S. Pat. No. 5,817,302.

By way of example of these silicone resins of T type, mention may be made of:
  polysilsesquioxanes of formula (RSiO$_{3/2}$).x (T units) in which x is greater than 100 and such that the group R is an alkyl group containing from 1 to 10 carbon atoms. Preferably, use may be made of the polymethylsilsesquioxane resins in which R represents a methyl group, for instance those sold by the company Wacker under the reference Resin MK, such as Belsil PMS MK: a polymer comprising CH$_3$SiO$_{3/2}$ repeat units (T units), also possibly comprising up to 1% by weight of (CH$_3$)$_2$SiO$_{3/2}$ units (D units) and having an average molecular weight of around 10 000,
  by the company Shin-Etsu under the reference KR-220L, which are composed of T units of formula CH$_3$SiO$_{312}$ and have Si—OH (silanol) end groups, under the reference KR-242A, which comprise 98% of T units and 2% of dimethyl D units and have Si—OH end groups, or alternatively under the reference KR-251 comprising 88% of T units and 12% of dimethyl D units and have Si—OH end groups.

MQT resins:
  Resins comprising MQT units that are in particular known are those mentioned in document U.S. Pat. No. 5,110,890.
  A preferred form of resins of MQT type are MQT-propyl (also known as MQT$^{Pr}$) resins. Such resins that may be used in the compositions according to the invention are in particular those described and prepared in patent application WO 2005/075 542, the content of which is incorporated herein by way of reference.
  The MQ-T-propyl resin preferably comprises the units:
  (i) (R$^1_3$SiO$_{1/2}$)$_a$
  (R$^2_2$SiO$_{2/2}$)$_b$
  (iii) (R$^3$SiO$_{3/2}$)$_c$ and
  (iv) (SiO$_{4/2}$)$_d$
  with
  R$^1$, R$^2$ and R$^3$ independently representing a hydrocarbon-based (in particular alkyl) radical containing from 1 to 10 carbon atoms, a phenyl group, a phenylalkyl group or alternatively a hydroxyl group and preferably an alkyl radical containing from 1 to 8 carbon atoms or a phenyl group,
  a being between 0.05 and 0.5,
  b being between zero and 0.3,
  c being greater than zero,
  d being between 0.05 and 0.6,
  a+b+c+d=1,
  on condition that more than 40 mol % of the groups R$^3$ of the siloxane resin are propyl groups.
  Preferably, the siloxane resin comprises the units:
  (i) (R$^1_3$SiO$_{1/2}$)$_a$
  (iii) (R$^3$SiO$_{3/2}$)$_c$ and
  (iv) (SiO$_{4/2}$)$_d$
  with
  R$^1$ and R$^3$ independently representing an alkyl group containing from 1 to 8 carbon atoms, R$^1$ preferably being a methyl group and R$^3$ preferably being a propyl group,
  a being between 0.05 and 0.5 and preferably between 0.15 and 0.4,
  c being greater than zero, preferably between 0.15 and 0.4,
  d being between 0.05 and 0.6, preferably between 0.2 and 0.6 or alternatively between 0.2 and 0.55,
  a+c+d=1,
  on condition that more than 40 mol % of the groups R$^3$ of the siloxane resin are propyl groups.
  The siloxane resins that may be used according to the invention may be obtained via a process comprising the reaction of:
  A) an MQ resin comprising at least 80 mol % of (R$^1_3$SiO$_{1/2}$)$_a$ and (SiO$_{4/2}$)$_d$ units,
    R$^1$ representing an alkyl group containing from 1 to 8 carbon atoms, an aryl group, a carbinol group or an amino group,
    a and d being greater than zero,
    the ratio a/d being between 0.5 and 1.5;
    and
  B) a propyl T resin comprising at least 80 mol % of (R$^3$SiO$_{3/2}$)$_c$, units,
    R$^3$ representing an alkyl group containing from 1 to 8 carbon atoms, an aryl group, a carbinol group or an amino group,
    c being greater than zero,
    on condition that at least 40 mol % of the groups R$^3$ are propyl groups,
    in which the A/B weight ratio is between 95/5 and 15/85 and preferably the A/B weight ratio is 30/70.

Advantageously, the A/B weight ratio is between 95/5 and 15/85. Preferably, the A/B ratio is less than or equal to 70/30. These preferred ratios have proven to allow comfortable deposits due to the absence of percolation of the rigid particles of MQ resin in the deposit.

The film-forming polymer may also be present in the composition in the form of particles dispersed in an aqueous phase, which is generally known as a latex or pseudolatex. The techniques for preparing these dispersions are well known to those skilled in the art.

As an aqueous dispersion of film-forming polymer, use may be made of the acrylic dispersions sold under the names Neocryl XK-90®, Neocryl A-1070®, Neocryl A-1090®, Neocryl BT-62®, Neocryl A–1079° and Neocryl A-523® by the company Avecia-Neoresins, Dow Latex 432° by the company Dow Chemical, Daitosol 5000 AD® or Daitosol 5000 SJ® by the company Daito Kasey Kogyo; Syntran 5760® by the company Interpolymer Allianz Opt®, Rohm and Haas, or else the aqueous dispersions of polyurethane which are sold under the names Neorez R-981® and Neorez R-974® by the company Avecia-Neoresins, Avalure UR-405®, Avalure UR-410®, Avalure UR-425®, Avalure UR-450®, Sancure 875°, Avalure UR-445® and Sancure 2060® by the company Noveon, Impranil 85° by the company Bayer, Aquamere H-1511® by the company Hydromer; the sulfopolyesters sold under the brand name Eastman AQ® by the company Eastman Chemical Products, vinyl dispersions, for instance Mexomere PAM®, aqueous dispersions of polyvinyl acetate, for instance Vinybran® from the company Nisshin Chemical or those sold by the company Union Carbide, aqueous dispersions of terpolymer of vinylpyrrolidone, dimethylaminopropylmethacrylamide and lauryldimethylpropylmethacrylamidoammonium chloride, such as Styleze W from ISP, aqueous dispersions of polyurethane/polyacrylic hybrid polymers, such as those sold under the references Hybridur® by the company Air Products or Duromer® from National Starch, core/shell-type dispersions: for example, those sold by the company Atofina under the reference Kynar (core: fluoro-shell: acrylic) or else those described in document U.S. Pat. No. 5,188,899 (core: silica-shell: silicone), and mixtures thereof.

According to one particular mode, the alkylcellulose (preferably ethylcellulose) may be used in a composition of the invention in the form of particles dispersed in an aqueous phase, like a dispersion of latex or pseudolatex type. The techniques for preparing these latex dispersions are well known to those skilled in the art.

The product sold by the company FMC Biopolymer under the name Aquacoat ECD-30, which consists of a dispersion of ethylcellulose in a proportion of about 26.2% by weight in water and stabilized with sodium lauryl sulfate and cetyl alcohol, is most particularly suitable for use as an aqueous dispersion of ethylcellulose.

Preferably, the film-forming polymer is chosen from vinyl polymers comprising at least one carbosiloxane dendrimer-based unit; film-forming block ethylenic copolymers; alkyl-celluloses; silicone resins, or combinations thereof.

Surfactants

According to a particular embodiment of the invention, the composition comprises at least one surfactant.

A surfactant or a mixture of surfactants may be present at from 0.05% to 20% by weight and preferably from 0.5% to 10% by weight, relative to the weight of the composition.

More particularly, the suitable surfactants may be chosen from non-ionic, anionic, cationic and amphoteric surfactants, and mixtures thereof.

For the choice of these surfactants, reference may be made to the document "Encyclopaedia of Chemical Technology, Kirk-Othmer", volume 22, pp. 333-432, 3rd edition, 1979, Wiley, for the definition of the properties and functions (emulsifying) of surfactants, in particular pp. 347-377 of this reference, for anionic and non-ionic surfactants.

Surfactants Promoting Direct Emulsions (Oil-in-Water; O/W)

Among the suitable surfactants promoting oil-in-water emulsions, mention may be made of the compounds which follow.

Non-Ionic Surfactants

In particular, at least one emulsifying surfactant having at 25° C. an HLB (hydrophilic-lipophilic balance) within the Griffin sense of greater than or equal to 8 may be used. The HLB value according to Griffin is defined in J. Soc. Cosm. Chem. 1954 (volume 5), pages 249-256.

An emulsifying surfactant having at 25° C. an HLB (hydrophilic-lipophilic balance) within the Griffin sense of less than 8 may also optionally be used.

The non-ionic surfactants may in particular be chosen from alkyl and polyalkyl esters of poly(ethylene oxide), oxyalkylenated alcohols, alkyl and polyalkyl ethers of poly (ethylene oxide), optionally polyoxyethylenated alkyl and polyalkyl esters of sorbitan, optionally polyoxyethylenated alkyl and polyalkyl ethers of sorbitan, alkyl and polyalkyl glycosides or polyglycosides, in particular alkyl and polyalkyl glucosides or polyglucosides, alkyl and polyalkyl esters of sucrose, optionally polyoxyethylenated alkyl and polyalkyl esters of glycerol, and optionally polyoxyethylenated alkyl and polyalkyl ethers of glycerol, and mixtures thereof.

1) Alkyl and polyalkyl esters of poly(ethylene oxide) that are preferably used are those with a number of ethylene oxide (EO) units ranging from 2 to 200. Examples that may be mentioned include stearate 40 EO, stearate 50 EO, stearate 100 EO, laurate 20 EO, laurate 40 EO and distearate 150 EO.

2) Alkyl and polyalkyl ethers of poly(ethylene oxide) that are preferably used are those with a number of ethylene oxide (EO) units ranging from 2 to 200. Examples that may be mentioned include cetyl ether 23 EO, oleyl ether 50 EO, phytosterol 30 EO, steareth 40, steareth 100 and beheneth 100.

3) Oxyalkylenated, in particular oxyethylenated and/or oxypropylenated, alcohols that are preferably used are those that can comprise from 1 to 150 oxyethylene and/or oxypropylene units, in particular containing from 20 to 100 oxyethylene units, in particular ethoxylated fatty alcohols, in particular of $C_8$-$C_{24}$ and preferably of $C_{12}$-$C_{18}$, such as stearyl alcohol ethoxylated with 20 oxyethylene units (CTFA name Steareth-20), for instance Brij 78 sold by the company Uniqema, cetearyl alcohol ethoxylated with 30 oxyethylene units (CTFA name Ceteareth-30), and the mixture of $C_{12}$-$C_{15}$ fatty alcohols comprising 7 oxyethylene units (CTFA name $C_{12}$-$C_{15}$ Pareth-7), for instance the product sold under the name Neodol 25-7® by Shell Chemicals; or in particular oxyalkylenated (oxyethylenated and/or oxypropylenated) alcohols containing from 1 to 15 oxyethylene and/or oxypropylene units, in particular ethoxylated $C_8$-$C_{24}$ and preferably $C_{12}$-$C_{18}$ fatty alcohols, such as stearyl alcohol ethoxylated with 2 oxyethylene units (CTFA name Steareth-2), for instance Brij 72 sold by the company Uniqema.

4) Optionally polyoxyethylenated alkyl and polyalkyl esters of sorbitan that are preferably used are those with a number of ethylene oxide (EO) units ranging from 0 to 100.

Examples that may be mentioned include sorbitan laurate 4 or 20 EO, in particular polysorbate 20 (or polyoxyethylene (20) sorbitan monolaurate) such as the product Tween 20 sold by the company Uniqema, sorbitan palmitate 20 EO, sorbitan stearate 20 EO, sorbitan oleate 20 EO, or the Cremophor products (RH 40, RH 60, etc.) from BASF.

5) Optionally polyoxyethylenated alkyl and polyalkyl ethers of sorbitan that are preferably used are those with a number of ethylene oxide (EO) units ranging from 0 to 100.

6) Alkyl and polyalkyl glucosides or polyglucosides that are preferably used are those containing an alkyl group comprising from 6 to 30 carbon atoms and preferably from 6 to 18 or even from 8 to 16 carbon atoms, and containing a glucoside group preferably comprising from 1 to 5 and in particular 1, 2 or 3 glucoside units. The alkylpolyglucosides may be chosen, for example, from decylglucoside (alkyl-$C_9/C_{11}$-polyglucoside (1.4)), for instance the product sold under the name Mydol 10® by the company Kao Chemicals or the product sold under the name Plantacare 2000 UP® by the company Henkel and the product sold under the name Oramix NS 10® by the company SEPPIC; caprylyUcapryl glucoside, for instance the product sold under the name Plantacare KE 3711® by the company Cognis or Oramix CG 110® by the company SEPPIC; laurylglucoside, for instance the product sold under the name Plantacare 1200 UP® by the company Henkel or Plantaren 1200 N® by the company Henkel; cocoglucoside, for instance the product sold under the name Plantacare 818 UP® by the company Henkel; caprylylglucoside, for instance the product sold under the name Plantacare 810 UP® by the company Cognis; and mixtures thereof.

7) Examples of alkyl and polyalkyl esters of sucrose that may be mentioned are Crodesta F150, sucrose monolaurate sold under the name Crodesta SL 40, and the products sold by Ryoto Sugar Ester, for instance sucrose palmitate sold under the reference Ryoto Sugar Ester P1670, Ryoto Sugar Ester LWA1695 or Ryoto Sugar Ester 01570.

8) Optionally polyoxyethylenated alkyl and polyalkyl esters of glycerol that are preferably used are those with a number of ethylene oxide (EO) units ranging from 0 to 100 and a number of glycerol units ranging from 1 to 30. Examples that may be mentioned include hexaglyceryl monolaurate and PEG-30 glyceryl stearate.

9) Optionally polyoxyethylenated alkyl and polyalkyl ethers of glycerol that are preferably used are those with a number of ethylene oxide (EO) units ranging from 0 to 100 and a number of glycerol units ranging from 1 to 30. Examples that may be mentioned include Nikkol Batyl Alcohol 100 and Nikkol Chimyl Alcohol 100.

Anionic Surfactants

The anionic surfactants may be chosen from alkyl ether sulfates, carboxylates, amino acid derivatives, sulfonates, isethionates, taurates, sulfosuccinates, alkylsulfoacetates, phosphates and alkyl phosphates, polypeptides, metal salts of $C_{10}$-$C_{30}$ and in particular $C_{12}$-$C_{20}$ fatty acids, in particular metal stearates, and mixtures thereof.

1) Examples of alkyl ether sulfates that may be mentioned include sodium lauryl ether sulfate (70/30 $C_{12}$-$C_{14}$) (2.2 EO) sold under the names Sipon AOS225 or Texapon N702 by the company Henkel, ammonium lauryl ether sulfate (70/30 $C_{12}$-$C_{14}$) (3 EO) sold under the name Sipon LEA 370 by the company Henkel, ammonium ($C_{12}$-$C_{14}$) alkyl ether (9 EO) sulfate sold under the name Rhodapex AB/20 by the company Rhodia Chimie, and the mixture of sodium magnesium lauryl oleyl ether sulfate sold under the name Empicol BSD 52 by the company Albright & Wilson.

2) Examples of carboxylates that may be mentioned include salts (for example alkali metal salts) of N-acylamino acids, glycol carboxylates, amido ether carboxylates (AECs) and polyoxyethylenated carboxylic acid salts.

The surfactant of glycol carboxylate type may be chosen from alkyl glycol carboxylics or 2-(2-hydroxyalkyloxy acetate), salts thereof and mixtures thereof. These alkyl glycol carboxylics comprise a linear or branched, saturated or unsaturated, aliphatic and/or aromatic alkyl chain containing from 8 to 18 carbon atoms. These carboxylics may be neutralized with mineral bases such as potassium hydroxide or sodium hydroxide.

Examples of surfactants of glycol carboxylic type that may be mentioned include sodium lauryl glycol carboxylate or sodium 2-(2-hydroxyalkyloxy acetate) such as the product sold under the name Beaulight Shaa® by the company Sanyo, Beaulight LCA-25N® or the corresponding acid form Beaulight Shaa (Acid form)®.

An example of an amido ether carboxylate (AEC) that may be mentioned is sodium lauryl amido ether carboxylate (3 EO) sold under the name Akypo Foam 30® by the company Kao Chemicals.

Examples of polyoxyethylenated carboxylic acid salts that may be mentioned include oxyethylenated (6 EO) sodium lauryl ether carboxylate (65/25/10 $C_{12\text{-}14\text{-}16}$) sold under the name Akypo Soft 45 NV® by the company Kao Chemicals, polyoxyethylenated and carboxymethylated fatty acids of olive oil origin sold under the name Olivem 400® by the company Biologia e Tecnologia, and oxyethylenated (6 EO) sodium tridecyl ether carboxylate sold under the name Nikkol ECTD-6 NEX® by the company Nikkol.

3) Amino acid derivatives that may in particular be mentioned include alkali metal salts of amino acids, such as:
   sarcosinates, for instance the sodium lauroyl sarcosinate sold under the name Sarkosyl NL 97® by the company Ciba or sold under the name Oramix L30® by the company SEPPIC, sodium myristoyl sarcosinate sold under the name Nikkol Sarcosinate MN® by the company Nikkol, and sodium palmitoyl sarcosinate sold under the name Nikkol Sarcosinate PN® by the company Nikkol;
   alaninates, for instance sodium N-lauroyl N-methyl amidopropionate sold under the name Sodium Nikkol Alaninate LN30® by the company Nikkol, or sold under the name Alanone ALE® by the company Kawaken, and triethanolamine N-lauroyl N-methyl alanine sold under the name Alanone Alta® by the company Kawaken;
   glutamates, for instance triethanolamine monococoyl glutamate sold under the name Acylglutamate CT-12® by the company Ajinomoto, or triethanolamine lauroyl glutamate sold under the name Acylglutamate LT-12® by the company Ajinomoto.
   aspartates, for instance the mixture of triethanolamine N-lauroyl aspartate and of triethanolamine N-myristoyl aspartate, sold under the name Asparack® by the company Mitsubishi;
   glycine derivatives (glycinates), for instance the sodium N-cocoyl glycinate sold under the names Amilite GCS-12® and Amilite GCK 12 by the company Ajinomoto;
   citrates, such as the oxyethylenated (9 mol) citric monoester of cocoyl alcohols sold under the name Witconol EC 1129 by the company Goldschmidt;
   galacturonates, such as the sodium dodecyl-D-galactoside uronate sold by the company Soliance.

4) Examples of sulfonates that may be mentioned include α-olefin sulfonates, for instance the sodium α-olefin sulfonate ($C_{14-16}$) sold under the name Bio-Terge AS-40® by the company Stepan, sold under the names Witconate AOS Protégé® and Sulframine AOS PH 12® by the company Witco or sold under the name Bio-Terge AS-40 CG® by the company Stepan, the sodium secondary olefin sulfonate sold under the name Hostapur SAS 30® by the company Clariant.

5) Isethionates that may be mentioned include acylisethionates, for instance sodium cocoylisethionate, such as the product sold under the name Jordapon CI P® by the company Jordan.

6) Taurates that may be mentioned include the sodium salt of palm kernel oil methyltaurate sold under the name Hostapon CT Pate® by the company Clariant; N-acyl N-methyltaurates, for instance the sodium N-cocoyl N-methyltaurate sold under the name Hostapon LT-SF® by the company Clariant or sold under the name Nikkol CMT-30-T® by the company Nikkol, and the sodium palmitoyl methyltaurate sold under the name Nikkol PMT® by the company Nikkol.

7) Examples of sulfosuccinates that may be mentioned include the oxyethylenated (3 EO) lauryl alcohol monosulfosuccinate (70/30 $C_{12}/C_{14}$) sold under the names Setacin 103 Special® and Rewopol SB-FA 30 K 4® by the company Witco, the disodium salt of a $C_{12}$-$C_{14}$ alkyl hemisulfosuccinate, sold under the name Setacin F Special Paste® by the company Zschimmer Schwarz, the oxyethylenated (2 EO) disodium oleamidosulfosuccinate sold under the name Standapol SH 135® by the company Henkel, the oxyethylenated (5 EO) laurylamide monosulfosuccinate sold under the name Lebon A-5000® by the company Sanyo, the oxyethylenated (10 EO) disodium salt of lauryl citrate monosulfosuccinate sold under the name Rewopol SB CS 50® by the company Witco, and the ricinoleic monoethanolamide monosulfosuccinate sold under the name Rewoderm S 1333® by the company Witco. Polydimethylsiloxane sulfosuccinates may also be used, such as disodium PEG-12 dimethicone sulfosuccinate sold under the name Mackanate-DC30 by the company MacIntyre.

8) Examples of alkyl sulfoacetates that may be mentioned include the mixture of sodium lauryl sulfoacetate and disodium lauryl ether sulfosuccinate, sold under the name Stepan-Mild LSB by the company Stepan.

9) Examples of phosphates and alkyl phosphates that may be mentioned include monoalkyl phosphates and dialkyl phosphates, such as the lauryl monophosphate sold under the name MAP 20® by the company Kao Chemicals, the potassium salt of dodecylphosphoric acid, the mixture of monoester and diester (predominantly diester) sold under the name Crafol AP-31® by the company Cognis, the mixture of octylphosphoric acid monoester and diester sold under the name Crafol AP-20® by the company Cognis, the mixture of ethoxylated (7 mol of EO) phosphoric acid monoester and diester of 2-butyloctanol, sold under the name Isofol 12 7 EO-Phosphate Ester® by the company Condea, the potassium or triethanolamine salt of mono($C_{12}$-$C_{13}$)alkyl phosphate sold under the references Arlatone MAP 230K-40® and Arlatone MAP 230T-60® by the company Uniqema, the potassium lauryl phosphate sold under the name Dermalcare MAP XC-99/09® by the company Rhodia Chimie, and the potassium cetyl phosphate sold under the name Arlatone MAP 160K by the company Uniqema.

10) The polypeptides are obtained, for example, by condensation of a fatty chain onto amino acids from cereals and in particular from wheat and oat. Examples of polypeptides that may be mentioned include the potassium salt of hydrolyzed lauroyl wheat protein, sold under the name Aminofoam W OR by the company Croda, the triethanolamine salt of hydrolyzed cocoyl soybean protein, sold under the name May-Tein SY by the company Maybrook, the sodium salt of lauroyl oat amino acids, sold under the name Proteol Oat by the company SEPPIC, collagen hydrolysate grafted onto coconut fatty acid, sold under the name Geliderm 3000 by the company Deutsche Gelatine, and soybean proteins acylated with hydrogenated coconut acids, sold under the name Proteol VS 22 by the company SEPPIC.

11) As metal salts of $C_{10}$-$C_{30}$ and in particular $C_{12}$-$C_{20}$ fatty acids, mention may be made in particular of metal stearates, such as sodium stearate and potassium stearate, and also polyhydroxystearates.

Cationic Surfactants

The cationic surfactants may be chosen from:
alkylimidazolidiniums such as isostearylethylimidonium ethosulfate,
ammonium salts, such as ($C_{12}$-$C_{30}$ alkyl)tri($C_1$-$C_4$ alkyl) ammonium halides, for instance N,N,N-trimethyl-1-docosanaminium chloride (or behentrimonium chloride).

Amphoteric Surfactants

The compositions according to the invention may also contain one or more amphoteric surfactants, for instance N-acylamino acids such as N-alkyl aminoacetates and disodium cocoamphodiacetate, and amine oxides such as stearamine oxide, or alternatively silicone surfactants, for instance dimethicone copolyol phosphates such as the product sold under the name Pecosil PS 100® by the company Phoenix Chemical.

Silicone Surfactants

According to a second embodiment, the composition comprises at least one silicone surfactant. Examples that may be mentioned include:
a) as non-ionic surfactants with an HLB of greater than or equal to 8 at 25° C., used alone or as a mixture; mention may be made in particular of:
dimethicone copolyol, such as the product sold under the name Q2-5220® by the company Dow Corning;
dimethicone copolyol benzoate, such as that sold under the names Finsolv SLB 101® and 201® by the company Fintex;
b) as non-ionic surfactants with an HLB of less than 8 at 25° C., used alone or as a mixture, mention may be made in particular of:
the mixture of cyclomethicone/dimethicone copolyol sold under the name Q2-3225C® by the company Dow Corning.

Surfactants Promoting Inverse Emulsions (Water-in-Oil; W/O)

As emulsifying surfactants that may be used for the preparation of the W/O emulsions, examples that may be mentioned include sorbitan alkyl esters or ethers; silicone surfactants, for instance dimethicone copolyols, such as the mixture of cyclomethicone and of dimethicone copolyol, sold under the name DC 5225 C by the company Dow Corning, and alkyldimethicone copolyols such as laurylmethicone copolyol sold under the name Dow Corning 5200 Formulation Aid by the company Dow Corning; cetyldimethicone copolyol, such as the product sold under the name Abil EM 90R by the company Goldschmidt, and the mixture of cetyldimethicone copolyol, of polyglyceryl isostearate (4 mol) and of hexyl laurate, sold under the name Abil WE 09 by the company Goldschmidt, or else phosphated surfactants.

One or more coemulsifiers may also be added thereto, which coemulsifiers may be chosen advantageously from the group comprising polyol alkyl esters.

Polyol alkyl esters that may in particular be mentioned include polyethylene glycol esters, for instance PEG-30 dipolyhydroxystearate, such as the product sold under the name Arlacel P135 by the company ICI.

A crosslinked elastomeric solid organopolysiloxane comprising at least one oxyalkylene group, such as the products obtained according to the procedure of Examples 3, 4 and 8 of document U.S. Pat. No. 5,412,004 and the examples of document U.S. Pat. No. 5,811,487, in particular the product of Example 3 (synthetic example) of patent U.S. Pat. No. 5,412,004, and as sold under the reference KSG 21 by the company Shin-Etsu, may also be used as surfactants for W/O emulsions.

According to one particularly preferred embodiment, an emulsion according to the invention, in particular a W/O emulsion, comprises at least one silicone surfactant, more particularly chosen from dimethicone copolyols.

A dimethicone copolyol that may be used according to the invention is an oxypropylenated and/or oxyethylenated polydimethylmethylsiloxane.

Dimethicone copolyols that may be used are those corresponding more particularly to formula (II) below:

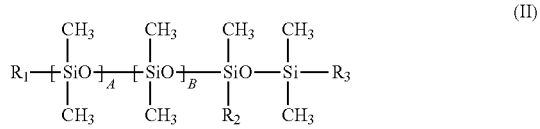
(II)

in which:
$R_1$, $R_2$ and $R_3$, independently of each other, represent a $C_1$-$C_6$ alkyl radical or a radical —$(CH_2)_x$—$(OCH_2CH_2)_y$—$(OCH_2CH_2CH_2)_z$—$OR_4$, at least one radical $R_1$, $R_2$ or $R_3$ not being an alkyl radical; $R_4$ being a hydrogen, a $C_1$-$C_3$ alkyl radical or a $C_2$-$C_4$ acyl radical;
A is an integer ranging from 0 to 200;
B is an integer ranging from 0 to 50; on condition that A and B are not simultaneously equal to zero;
x is an integer ranging from 1 to 6;
y is an integer ranging from 1 to 30; and
z is an integer ranging from 0 to 5.

According to one preferred embodiment, in the compound of formula (II), $R_1$=$R_3$=methyl radical, x is an integer ranging from 2 to 6 and y is an integer ranging from 4 to 30. $R_4$ is in particular a hydrogen.

Examples of compounds of formula (II) that may be mentioned include the compounds of formula (III):

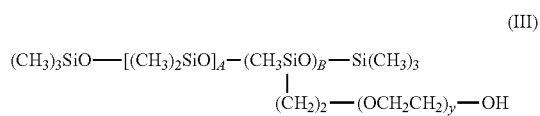
(III)

in which A is an integer ranging from 20 to 105, B is an integer ranging from 2 to 10 and y is an integer ranging from 10 to 20.

Examples of silicone compounds of formula (II) that may also be mentioned include the compounds of formula (IV):

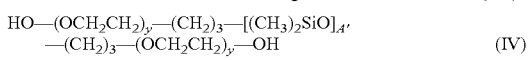

HO—$(OCH_2CH_2)_y$—$(CH_2)_3$—$[(CH_3)_2SiO]_{A'}$—$(CH_2)_3$—$(OCH_2CH_2)_y$—OH (IV)

in which A' and y are integers ranging from 10 to 20.

Dimethicone copolyols that may be used include those sold under the names DC 5329, DC 7439-146, DC 2-5695 and Q4-3667 by the company Dow Corning; KF-6013, KF-6015, KF-6016. KF-6017 and KF-6028 by the company Shin-Etsu.

The compounds DC 5329, DC 7439-146 and DC 2-5695 are compounds of formula (III) in which, respectively, A is 22, B is 2 and y is 12; A is 103, B is 10 and y is 12; A is 27, B is 3 and y is 12.

According to a particular embodiment, the silicone surfactant may be PEG polydimethylsiloxyethyl dimethicone, sold in particular by the company Shin-Etsu under the reference KF-6028, PEG-10 dimethicone sold in particular by the company Shin-Etsu under the reference KF-6017, and mixtures thereof.

The surfactant may also be chosen from non-ionic surfactants of the type of monoglycerolated or polyglycerolated fatty alcohols which can be represented by formula (V) below:

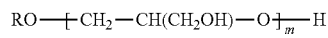

in which:
R represents a linear or branched, saturated or unsaturated radical comprising from 8 to 40 carbon atoms and preferably from 10 to 30 carbon atoms;
m represents a number ranging from 1 to 10.

As compounds of this type, mention may be made of lauryl alcohol comprising 4 mol of glycerol, isostearyl alcohol comprising 4 mol of glycerol, lauryl alcohol comprising 1.5 mol of glycerol, oleyl alcohol comprising 4 mol of glycerol, oleyl alcohol comprising 2 mol of glycerol, cetearyl alcohol comprising 2 mol of glycerol, cetearyl alcohol comprising 6 mol of glycerol, oleocetyl alcohol comprising 6 mol of glycerol, and octadecanol comprising 6 mol of glycerol.

The fatty alcohol can represent a mixture of fatty alcohols in the same way that the value of in represents a statistical value, which means that, in a commercial product, several types of polyglycerolated fatty alcohols can coexist in the form of a mixture.

Preferably, whatever the direction of the emulsion, the surfactant(s) is (are) chosen from non-ionic surfactants and silicone surfactants, or mixtures thereof.

Volatile Oils

According to one particular embodiment of the invention, the composition comprises at least one volatile oil.

The volatile oil may in particular be a silicone oil, a hydrocarbon-based oil, which is preferably non-polar, or a fluoro oil.

According to one embodiment, the volatile oil is a silicone oil and may be chosen in particular from silicone oils with a flash point ranging from 40° C. to 102° C., preferably with a flash point of greater than 55° C. and less than or equal to 95° C., and preferentially ranging from 65° C. to 95° C.

As volatile silicone oils that may be used in the invention, mention may be made of linear or cyclic silicones with a viscosity at ambient temperature of less than 8 centistokes (eSt) ($8 \times 10^{-6}$ m$^2$/s), and in particular containing from 2 to 10 silicon atoms and in particular from 2 to 7 silicon atoms, these silicones optionally comprising alkyl or alkoxy groups containing from 1 to 10 carbon atoms.

As volatile silicone oils that may be used in the invention, mention may be made in particular of dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

According to a second embodiment, the volatile oil is a fluoro oil, such as nonafluoromethoxybutane or perfluoromethylcyclopentane, and mixtures thereof.

According to a third embodiment, the volatile oil is a hydrocarbon-based oil, which is preferably non-polar.

The non-polar volatile hydrocarbon-based oil may have a flash point ranging from 40° C. to 102° C., preferably ranging from 40° C. to 55° C. and preferentially ranging from 40° C. to 50° C.

The hydrocarbon-based volatile oil may in particular be chosen from hydrocarbon-based volatile oils containing from 8 to 16 carbon atoms, and mixtures thereof, and in particular:
- branched $C_8$-$C_{16}$ alkanes such as $C_8$-$C_{16}$ isoalkanes (also known as isoparaffins), isododecane, isodecane and isohexadecane, and, for example, the oils sold under the trade name Isopar or Pennethyl,
- linear alkanes, for instance n-dodecane (C12) and n-tetradecane (C14) sold by Sasol under the respective references Parafol 12-97 and Parafol 14-97, and also mixtures thereof, the undecane-tridecane mixture (Cetiol UT), the mixtures of n-undecane (C11) and of n-tridecane (C13) obtained in Examples 1 and 2 of patent application WO 2008/155 059 from the company Cognis, and mixtures thereof.

According to one particular embodiment, the volatile oil(s) may be present in a content ranging from 0.1% to 30% by weight and in particular from 0.5% to 25% by weight, relative to the total weight of said composition.

Hydrophilic Gelling Polymers

The composition may also comprise at least one hydrophilic gelling polymer.

For the purposes of the present patent application, the term "hydrophilic gelling agent" is intended to mean a polymer that is capable of gelling the aqueous phase of the compositions according to the invention.

The gelling polymer that may be used according to the invention may in particular be characterized by its capacity to form in water, beyond a certain concentration C*, a gel characterized by oscillatory rheology ($\mu$=1 Hz) by a flow threshold $\tau_c$ at least equal to 10 Pa. This concentration C* may vary widely according to the nature of the gelling polymer under consideration.

By way of illustration, this concentration is between 1% and 2% by weight for an acrylamide/sodium acrylamido-2-methylpropanesulfonate copolymer as an inverse emulsion at 40% in polysorbate 80/I-C16, for instance the product sold under the name Simulgel 600 by the company SEPPIC, and is about 0.5% by weight for an AMPS/ethoxylated (25 EO) cetearyl methacrylate copolymer crosslinked with trimethylolpropane triacrylate (TMPTA) of the Aristoflex HMS type.

The gelling polymer may be present in the composition in an amount that is sufficient to adjust the stiffness modulus G* (1 Hz, 25° C.) of the composition to a value greater than or equal to 10 000 Pa and in particular ranging from 10 000 Pa to 100 000 Pa. The method for measuring the stiffness modulus G* (1 Hz, 25° C.) of the composition is described in greater detail hereinbelow.

If it is present, the gelling polymer is a hydrophilic polymer and is thus present in the aqueous phase of the composition.

More particularly, this gelling polymer may be chosen from:
- acrylic or methacrylic acid homopolymers or copolymers or salts and esters thereof and in particular the products sold under the names Versicol F or Versicol K by the company Allied Colloid, Ultrahold 8 by the company Ciba-Geigy, and polyacrylic acids of Synthalen K type, and salts, in particular sodium salts, of polyacrylic acids (corresponding to the INCI name sodium acrylate copolymer) and more particularly a crosslinked sodium polyacrylate (corresponding to the INCI name sodium acrylate copolymer (and) caprylic/capric triglyceride) sold under the name Luvigel EM by the company BASF,
- copolymers of acrylic acid and of acrylamide sold in the form of the sodium salt thereof under the name Reten by the company Hercules, the sodium polymethacrylate sold under the name Darvan No. 7 by the company Vanderbilt, and the sodium salts of polyhydroxycarboxylic acids sold under the name Hydagen F by the company Henkel,
- polyacrylic acid/alkyl acrylate copolymers, preferably modified or unmodified carboxyvinyl polymers; the copolymers most particularly preferred according to the present invention are acrylate/$C_{10}$-$C_{30}$-alkylacrylate copolymers (INCI name: Acrylates/$C_{10\text{-}30}$ Alkyl acrylate Crosspolymer) such as the products sold by the company Lubrizol under the trade names Pemulen TR1, Pemulen TR2, Carbopol 1382 and Carbopol EDT 2020, and even more preferentially Pemulen TR-2,
- AMPS (polyacrylamidomethylpropanesulfonic acid partially neutralized with aqueous ammonia and highly crosslinked) sold by the company Clariant,
- AMPS/acrylamide copolymers of Sepigel or Simulgel type sold by the company SEPPIC,
- polyoxyethylenated AMPS/alkyl methacrylate copolymers (crosslinked or non-crosslinked) of the Aristoflex HMS type sold by the company Clariant,
and mixtures thereof.

Other examples of hydrophilic gelling polymers that may be mentioned include:
- anionic, cationic, amphoteric or non-ionic chitin or chitosan polymers;
- cellulose polymers, other than the alkylcellulose mentioned in the film-forming agents, chosen from hydroxyethylcellulose, hydroxypropylcellulose, hydroxymethylcellulose, ethylhydroxyethylcellulose and carboxymethylcellulose, and also quaternized cellulose derivatives;
- vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam;
- polyvinyl alcohol;
- optionally modified polymers of natural origin, such as: galactomannans and derivatives thereof, such as konjac gum, gellan gum, locust bean gum, fenugreek gum, karaya gum, gum tragacanth, gum arabic, acacia gum, guar gum, hydroxypropyl guar, hydroxypropyl guar modified with sodium methylcarboxylate groups (Jaguar XC97-1, Rhodia), hydroxypropyltrimethylammonium guar chloride, and xanthan derivatives;

alginates and carrageenans;
glycoaminoglycans, hyaluronic acid and its derivatives;
deoxyribonucleic acid;
mucopolysaccharides such as hyaluronic acid or chondroitin sulfates, and mixtures thereof.

According to one preferred embodiment, the gelling polymer is chosen from acrylic or methacrylic acid homopolymers or copolymers or salts and esters thereof, polyacrylic acids and polyacrylic acid salts, or mixtures thereof.

According to one preferred embodiment, the gelling polymer is a sodium salt of polyacrylic acid, in particular a crosslinked sodium polyacrylate.

According to one particularly preferred embodiment, the gelling agent is chosen from associative polymers.

The term "associative polymer" is intended to mean any amphiphilic polymer comprising in its structure at least one fatty chain and at least one hydrophilic portion. The associative polymers in accordance with the present invention may be anionic, cationic, non-ionic or amphoteric.

Associative Anionic Polymers

Among the associative anionic polymers that may be mentioned are those comprising at least one hydrophilic unit, and at least one fatty-chain allyl ether unit, more particularly those of which the hydrophilic unit is formed by an unsaturated ethylenic anionic monomer, more particularly by a vinylcarboxylic acid and most particularly by an acrylic acid or a methacrylic acid or mixtures thereof, and of which the fatty-chain allyl ether unit corresponds to the monomer of formula (I) below:

$$CH_2=C(R')CH_2OB_nR \quad (I)$$

in which R' denotes H or $CH_3$, B denotes the ethylenoxy radical, n is zero or denotes an integer ranging from 1 to 100, R denotes a hydrocarbon-based radical chosen from alkyl, arylalkyl, aryl, alkylaryl and cycloalkyl radicals, comprising from 8 to 30 carbon atoms, preferably 10 to 24 and even more particularly from 12 to 18 carbon atoms.

Anionic amphiphilic polymers of this type are described and prepared, according to an emulsion polymerization process, in patent EP-0 216 479.

Among the associative anionic polymers that may also be mentioned are maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name Performa V 1608 by the company Newphase Technologies.

Among the associative anionic polymers, it is possible, according to one preferred embodiment, to use copolymers comprising among their monomers an α,β-monoethylenically unsaturated carboxylic acid and an ester of an α,β-monoethylenically unsaturated carboxylic acid and of an oxyalkylenated fatty alcohol.

Preferentially, these compounds also comprise as monomer an ester of an α,β-monoethylenically unsaturated carboxylic acid and of a $C_1$-$C_4$ alcohol.

Examples of compounds of this type that may be mentioned include Aculyn 22® sold by the company Röhm & Haas, which is a methacrylic acid/ethyl acrylate/oxyalkylenated stearyl methacrylate (comprising 20 EO units) terpolymer or Aculyn 28 (methacrylic acid/ethyl acrylate/oxyethylenated behenyl methacrylate (25 EO) terpolymer).

Associative anionic polymers that may also be mentioned include anionic polymers comprising at least one hydrophilic unit of unsaturated olefinic carboxylic acid type, and at least one hydrophobic unit exclusively of the ($C_{10}$-$C_{30}$) alkyl ester of an unsaturated carboxylic acid type. Examples that may be mentioned include the anionic polymers described and prepared according to patents U.S. Pat. Nos. 3,915,921 and 4,509,949.

Cationic Associative Polymers

Cationic associative polymers that may be mentioned include quaternized cellulose derivatives and polyacrylates bearing amine side groups.

The quaternized cellulose derivatives are, in particular:
quaternized celluloses modified with groups comprising at least one fatty chain, such as alkyl, arylalkyl or alkylaryl groups comprising at least 8 carbon atoms, or mixtures thereof,
quaternized hydroxyethylcelluloses modified with groups comprising at least one fatty chain, such as alkyl, arylalkyl or alkylaryl groups comprising at least 8 carbon atoms, or mixtures thereof.

The polyacrylates bearing quaternized or non-quaternized amine side groups contain, for example, hydrophobic groups of the steareth-20 (polyoxyethylenated (20) stearyl alcohol) type.

The alkyl radicals borne by the above quaternized celluloses or hydroxyethylcelluloses preferably comprise from 8 to 30 carbon atoms. The aryl radicals preferably denote phenyl, benzyl, naphthyl or anthryl groups.

Examples of quaternized alkylhydroxyethylcelluloses containing $C_8$-$C_{30}$ fatty chains that may be indicated include the products Quatrisoft LM 200, Quatrisoft LM-X 529-18-A, Quatrisoft LM-X 529-18B ($C_{12}$ alkyl) and Quatrisoft LM-X 529-8 ($C_{18}$ alkyl) sold by the company Amerchol and the products Crodacel QM, Crodacel QL ($C_{12}$ alkyl) and Crodacel QS ($C_{18}$ alkyl) sold by the company Croda.

Examples of polyacrylates bearing amino side chains that may be mentioned are the polymers 8781-121B or 9492-103 from the company National Starch.

Non-Ionic Associative Polymers

The non-ionic associative polymers may be chosen from:
celluloses modified with groups comprising at least one fatty chain (comprising at least 8 carbon atoms), for instance hydroxyethylcelluloses modified with groups comprising at least one fatty chain, such as alkyl groups, in particular of $C_8$-$C_{22}$, arylalkyl groups or alkylaryl groups, such as Natrosol Plus Grade 330 CS ($C_{16}$ alkyls) sold by the company Aqualon,
celluloses modified with alkylphenol polyalkylene glycol ether groups, such as the product Amercell Polymer HM-1500 (nonylphenol polyethylene glycol (15) ether) sold by the company Amerchol,
guars such as hydroxypropyl guar, modified with groups comprising at least one fatty chain such as an alkyl chain, in particular of $C_8$-$C_{22}$,
copolymers of vinylpyrrolidone and of fatty-chain hydrophobic monomers comprising in particular at least 8 carbon atoms,
copolymers of $C_1$-$C_6$ alkyl methacrylates or acrylates and of amphiphilic monomers comprising at least one fatty chain,
copolymers of hydrophilic methacrylates or acrylates and of hydrophobic monomers comprising at least one fatty chain, for example of $C_1$-$C_6$, for instance polyethylene glycol methacrylate/lauryl methacrylate copolymer,
associative polyurethanes.

Associative polyurethanes are non-ionic block copolymers comprising in the chain both hydrophilic blocks usually of polyoxyethylene nature (polyurethanes may then be referred to as polyurethane polyethers), and hydrophobic blocks that may be aliphatic sequences alone and/or cycloaliphatic and/or aromatic sequences.

In particular, these polymers comprise at least two hydrocarbon-based lipophilic chains containing from 8 to 30 carbon atoms, separated by a hydrophilic block, the hydrocarbon-based chains possibly being pendent chains or chains at the end of the hydrophilic block. In particular, it is possible for one or more pendent chains to be envisioned. In addition, the polymer may comprise a hydrocarbon-based chain at one end or at both ends of a hydrophilic block.

Associative polyurethanes may be block polymers, in triblock or multiblock form. The hydrophobic blocks may thus be at each end of the chain (for example: triblock copolymer containing a hydrophilic central block) or distributed both at the ends and in the chain (for example: multiblock copolymer). These polymers may also be graft polymers or star polymers. Preferably, the associative polyurethanes are triblock copolymers in which the hydrophilic block is a polyoxyethylene chain comprising from 50 to 1000 oxyethylene groups. In general, associative polyurethanes comprise a urethane bond between the hydrophilic blocks, whence arises the name.

According to one preferred embodiment, a non-ionic associative polymer of polyurethane type is used as gelling agent.

By way of example of polyurethane polyethers that may not be used in the invention, mention may be made of the polymer $C_{16}$-$OE_{120}$-$C_{16}$ from the company Servo Delden (under the name SER AD FX1100, which is a molecule containing a urethane function and having a weight-average molecular weight of 1300), OE being an oxyethylene unit.

Rheolate 205 bearing a urea function, sold by the company Rheox, or Rheolate 208 or 204, or alternatively Rheolate FX 1100 by Elementis, may also be used as associative polyurethane polymer. These associative polyurethanes are sold in pure form. The product DW 1206B from Röhm & Haas containing a $C_{20}$ alkyl chain and a urethane bond, sold at a solids content of 20% in water, may also be used.

Use may also be made of solutions or dispersions of these polymers, in particular in water or in aqueous-alcoholic medium. Examples of such polymers that may be mentioned include SER AD FX1010, SER AD FX1035 and SER AD 1070 from the company Servo Delden, and Rheolate 255, Rheolate 278 and Rheolate 244 sold by the company Rheox. It is also possible to use the products Aculyn 46, DW 1206F and DW 1206J, and also Acrysol RM 184 or Acrysol 44 from the company Röhm & Haas, or alternatively Borchigel LW 44 from the company Borchers, and mixtures thereof.

According to one preferred embodiment, if it is present, the hydrophilic gelling agent is chosen from:
optionally modified hydroxypropyl guar, in particular hydroxypropyl guar modified with sodium methylcarboxylate groups (Jaguar XC97-1, Rhodia) or hydroxypropyltrimethylammonium guar chloride,
vinyl polymers, such as polyvinyl alcohol,
anionic associative polymers derived from (meth)acrylic acid, such as the non-crosslinked copolymer obtained from methacrylic acid and steareth-20 methacrylate, sold under the name Aculyn 22 by Röhm & Haas,
non-ionic associative polymers of polyurethane polyether type, such as the Steareth-100/PEG-136/HDI copolymer sold under the name Rheolate FX 1100 by Elementis.

Amphoteric Associative Polymers

Among the associative amphoteric polymers of the invention, mention may be made of crosslinked or non-crosslinked, branched or unbranched amphoteric polymers, which may be obtained by copolymerization 1) of at least one monomer of formula (IVa) or (IVb):

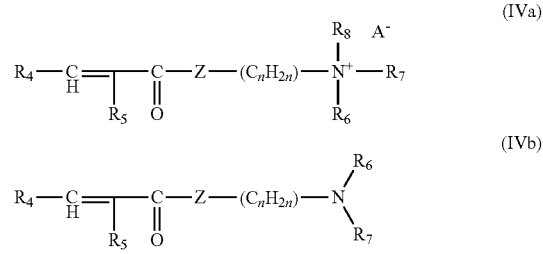

in which $R_4$ and $R_5$, which may be identical or different, represent a hydrogen atom or a methyl radical,
$R_6$, $R_7$ and $R_8$, which may be identical or different, represent a linear or branched alkyl radical containing from 1 to 30 carbon atoms,
Z represents a group NH or an oxygen atom,
n is an integer from 2 to 5,
$A^-$ denotes an anion derived from a mineral or organic acid, such as a methosulfate anion or a halide such as chloride or bromide.

2) of at least one monomer of formula (V):

in which $R_9$ and $R_{10}$, which may be identical or different, represent a hydrogen atom or a methyl radical;
$Z_1$ represents a group OH or a group NHC$(CH_3)_2CH_2SO_3H$;

3) of at least one monomer of formula (VI):

in which $R_9$ and $R_{10}$, which may be identical or different, represent a hydrogen atom or a methyl radical, X denotes an oxygen or nitrogen atom and $R_{11}$ denotes a linear or branched alkyl radical containing from 1 to 30 carbon atoms;

4) optionally at least one crosslinking or branching agent; at least one of the monomers of formula (IVa), (IVb) or (VI) comprising at least one fatty chain containing from 8 to 30 carbon atoms and said compounds of the monomers of formulae (IVa), (IVb), (V) and (VI) possibly being quaternized, for example with a $C_1$-$C_4$ alkyl halide or a $C_1$-$C_4$ dialkyl sulfate.

The monomers of formulae (IVa) and (IVb) of the present invention are preferably chosen from the group formed by:
dimethylaminoethyl methacrylate, dimethylaminoethyl acrylate,
diethylaminoethyl methacrylate, diethylaminoethyl acrylate,
dimethylaminopropyl methacrylate, dimethylaminopropyl acrylate,
dimethylaminopropylmethacrylamide or dimethylaminopropylacrylamide, optionally quaternized, for example with a $C_1$-$C_4$ alkyl halide or a $C_1$-$C_4$ dialkyl sulfate.

More particularly, the monomer of formula (IVa) is chosen from acrylamidopropyltrimethylammonium chloride and methacrylamidopropyltrimethylammonium chloride.

The compounds of formula (V) of the present invention are preferably chosen from the group formed by acrylic acid, methacrylic acid, crotonic acid, 2-methylcrotonic acid, 2-acrylamido-2-methylpropanesulfonic acid and 2-methacrylamido-2-methylpropanesulfonic acid. More particularly, the monomer of formula (V) is acrylic acid.

The monomers of formula (VI) of the present invention are preferably chosen from the group formed by $C_{12}$-$C_{22}$ and more particularly $C_{16}$-$C_{18}$ alkyl acrylates or methacrylates.

The crosslinking or branching agent is preferably chosen from N,N'-methylenebisacrylamide, triallylmethylammonium chloride, allyl methacrylate, n-methylolacrylamide, polyethylene glycol di methacrylates, ethylene glycol dimethacrylate, diethylene glycol dimethacrylate, 1,6-hexanediol dimethacrylate and allyl sucrose.

The polymers according to the invention may also contain other monomers such as non-ionic monomers and in particular $C_1$-$C_4$ alkyl acrylates or methacrylates.

The ratio of the number of cationic charges/anionic charges in these amphoteric polymers is preferably equal to about 1.

The weight-average molecular weights of the associative amphoteric polymers have a weight-average molecular mass of greater than 500, preferably between 10 000 and 10 000 000 and even more preferentially between 100 000 and 8 000 000.

Preferably, the associative amphoteric polymers of the invention contain from 1 mol % to 99 mol %, more preferentially from 20 mol % to 95 mol % and even more preferentially from 25 mol % to 75 mol % of compound(s) of formula (IVa) or (IVb). They also preferably contain from 1 mol % to 80 mol %, more preferentially from 5 mol % to 80 mol % and even more preferentially from 25 mol % to 75 mol % of compound(s) of formula (V). The content of compound(s) of formula (VI) is preferably between 0.1 mol % and 70 mol %, more preferentially between 1 mol % and 50 mol % and even more preferentially between 1 mol % and 10 mol %. The crosslinking or branching agent, when it is present, is preferably between 0.0001 mol % and 1 mol % and even more preferentially between 0.0001 mol % and 0.1 mol %.

Preferably, the mole ratio between the compound(s) of formula (IVa) or (IVb) and the compound(s) of formula (V) ranges from 20/80 to 95/5 and more preferentially from 25/75 to 75/25.

The associative amphoteric polymers according to the invention are described, for example, in patent application WO 98/44012.

The amphoteric polymers that are particularly preferred according to the invention are chosen from acrylic acid/acrylamidopropyltrimethylammonium chloride/stearyl methacrylate copolymers.

The gelling polymer(s) of the aqueous phase, if they are used, and in particular the associative polymers, may be present in the composition according to the invention in a total active material content ranging from 0.1% to 10% by weight and preferably from 0.5% to 5% by weight relative to the total weight of the composition.

Colorants

A composition in accordance with the present invention may comprise at least one coloring material (colorant), which may be chosen from water-soluble or water-insoluble, liposoluble or non-liposoluble, organic or inorganic colorants, and materials with an optical effect, and mixtures thereof.

For the purposes of the present invention, the term "colorant" is intended to mean a compound that is capable of producing a coloured optical effect when it is formulated in sufficient amount in a suitable cosmetic medium.

The water-soluble colorants used according to the invention are more particularly water-soluble dyes.

For the purposes of the invention, the term "water-soluble dye" is intended to mean any natural or synthetic, generally organic compound, which is soluble in an aqueous phase or water-miscible solvents and which is capable of colouring. In particular, the term "water-soluble" is intended to mean the capacity of a compound to be dissolved in water, measured at 25° C., to a concentration at least equal to 0.1 g/l (production of a macroscopically isotropic, transparent, coloured or colourless solution). This solubility is in particular greater than or equal to 1 g/l.

As water-soluble dyes that are suitable for use in the invention, mention may be made in particular of synthetic or natural water-soluble dyes, for instance FDC Red 4 (CI: 14700), DC Red 6 (Lithol Rubine Na; CI: 15850), DC Red 22 (CI: 45380), DC Red 28 (CI: 45410 Na salt), DC Red 30 (CI: 73360), DC Red 33 (CI: 17200), DC Orange 4 (CI: 15510), FDC Yellow 5 (CI: 19140), FDC Yellow 6 (CI: 15985), DC Yellow 8 (CI: 45350 Na salt), FDC Green 3 (CI: 42053), DC Green 5 (CI: 61570), FDC Blue 1 (CI: 42090).

As nonlimiting illustrations of sources of water-soluble dyes(s) that may be used in the context of the present invention, mention may be made in particular of those of natural origin, such as extracts of cochineal carmine, of beetroot, of grape, of carrot, of tomato, of annatto, of paprika, of henna, of caramel and of curcumin.

Thus, the water-soluble dyes that are suitable for use in the invention are in particular carminic acid, betanin, anthocyans, enocyanins, lycopene, β-carotene, bixin, norbixin, capsanthin, capsorubin, flavoxanthin, lutein, cryptoxanthin, rubixanthin, violaxanthin, riboflavin, rhodoxanthin, cantaxanthin and chlorophyll, and mixtures thereof.

They may also be copper sulfate, iron sulfate, water-soluble sulfopolyesters, rhodamine, betaine, methylene blue, the disodium salt of tartrazine and the disodium salt of fuchsin.

Some of these water-soluble dyes are in particular permitted for food use. Representatives of these dyes that may be mentioned more particularly include dyes of the carotenoid family, referenced under the food codes E120, E162, E163, E160a-g, E150a, E101, E100, E140 and E141.

According to one particularly preferred embodiment, the water-soluble dye(s) is (are) chosen from the disodium salt of brilliant yellow FCF sold by the company LCW under the name DC Yellow 6, the disodium salt of fuchsin acid D sold by the company LCW under the name DC Red 33, and the trisodium salt of Rouge Allura sold by the company LCW under the name FD & C Red 40.

The term "pigments" should be understood as meaning white or coloured, inorganic (mineral) or organic particles, which are insoluble in the liquid organic phase, and which are intended to colour and/or opacify the composition and/or the deposit produced with the composition.

The pigments may be chosen from mineral pigments, organic pigments and composite pigments (i.e. pigments based on mineral and/or organic materials).

The pigments may be chosen from monochromatic pigments, lakes, nacres, and pigments with an optical effect, for instance reflective pigments and goniochromatic pigments.

The mineral pigments may be chosen from metal oxide pigments, chromium oxides, iron oxides, titanium dioxide, zinc oxides, cerium oxides, zirconium oxides, manganese violet, Prussian blue, ultramarine blue and ferric blue, and mixtures thereof.

Organic lakes are organic pigments formed from a dye attached to a substrate.

The lakes, which are also known as organic pigments, may be chosen from the materials below, and mixtures thereof:
cochineal carmine;
organic pigments of azo dyes, anthraquinone dyes, indigoid dyes, xanthene dyes, pyrene dyes, quinoline dyes, triphenylmethane dyes or fluoran dyes. Among the organic pigments that may in particular be mentioned are those known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6;
the organic lakes may be insoluble sodium, potassium, calcium, barium, aluminium, zirconium, strontium or titanium salts of acidic dyes such as azo, anthraquinone, indigoid, xanthene, pyrene, quinoline, triphenylmethane or fluoran dyes, these dyes possibly comprising at least one carboxylic or sulfonic acid group.

The organic lakes may also be supported on an organic support such as rosin or aluminium benzoate, for example.

Among the organic lakes, mention may in particular be made of those known under the following names: D&C Red No. 2 Aluminium lake, D&C Red No. 3 Aluminium lake, D&C Red No. 4 Aluminium lake, D&C Red No. 6 Aluminium lake, D&C Red No. 6 Barium lake, D&C Red No. 6 Barium/Strontium lake, D&C Red No. 6 Strontium lake, D&C Red No. 6 Potassium lake, D&C Red No. 7 Aluminium lake, D&C Red No. 7 Barium lake, D&C Red No. 7 Calcium lake, D&C Red No. 7 Calcium/Strontium lake, D&C Red No. 7 Zirconium lake, D&C Red No. 8 Sodium lake, D&C Red No. 9 Aluminium lake, D&C Red No. 9 Barium lake, D&C Red No. 9 Barium/Strontium lake, D&C Red No. 9 Zirconium lake, D&C Red No. 10 Sodium lake, D&C Red No. 19 Aluminium lake, D&C Red No. 19 Barium lake, D&C Red No. 19 Zirconium lake, D&C Red No. 21 Aluminium lake, D&C Red No. 21 Zirconium lake, D&C Red No. 22 Aluminium lake, D&C Red No. 27 Aluminium lake, D&C Red No. 27 Aluminium/Titanium/Zirconium lake, D&C Red No. 27 Barium lake, D&C Red No. 27 Calcium lake, D&C Red No. 27 Zirconium lake, D&C Red No. 28 Aluminium lake, D&C Red No. 30 lake, D&C Red No. 31 Calcium lake, D&C Red No. 33 Aluminium lake, D&C Red No. 34 Calcium lake, D&C Red No. 36 lake, D&C Red No. 40 Aluminium lake, D&C Blue No. 1 Aluminium lake, D&C Green No. 3 Aluminium lake, D&C Orange No. 4 Aluminium lake, D&C Orange No. 5 Aluminium lake, D&C Orange No. 5 Zirconium lake, D&C Orange No. 10 Aluminium lake, D&C Orange No. 17 Barium lake, D&C Yellow No. 5 Aluminium lake, D&C Yellow No. 5 Zirconium lake, D&C Yellow No. 6 Aluminium lake, D&C Yellow No. 7 Zirconium lake, D&C Yellow No. 10 Aluminium lake, FD&C Blue No. 1 Aluminium lake, FD&C Red No. 4 Aluminium lake, FD&C Red No. 40 Aluminium lake, FD&C Yellow No. 5 Aluminium lake, FD&C Yellow No. 6 Aluminium lake.

Mention may also be made of liposoluble dyes, such as, for example, Sudan Red, DC Red 17, DC Green 6, β-carotene, soyabean oil, Sudan Brown, DC Yellow 11, DC Violet 2, DC Orange and quinoline yellow.

The chemical substances corresponding to each of the organic colorants cited above are mentioned in the publication "International Cosmetic Ingredient Dictionary and Handbook", 1997 edition, pages 371 to 386 and 524 to 528, published by The Cosmetic, Toiletries and Fragrance Association, the content of which is incorporated into the present patent application by way of reference.

The pigments may also have been subjected to a hydrophobic treatment.

The hydrophobic treatment agent may be chosen from silicones such as methicones, dimethicones and perfluoroalkylsilanes; fatty acids such as stearic acid; metal soaps such as aluminium dimyristate, the aluminium salt of hydrogenated tallow glutamate, perfluoroalkyl phosphates, perfluoroalkylsilanes, perfluoroalkylsilazanes, polyhexafluoropropylene oxides, polyorganosiloxanes comprising perfluoroalkyl perfluoropolyether groups and amino acids; N-acylamino acids or salts thereof; lecithin, isopropyl triisostearyl titanate, and mixtures thereof.

The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be aluminium, magnesium, calcium, zirconium, zinc, sodium or potassium salts. The amino acid may be, for example, lysine, glutamic acid or alanine.

The term "alkyl" mentioned in the compounds cited above denotes in particular an alkyl group containing from 1 to 30 carbon atoms and preferably containing from 5 to 16 carbon atoms.

Hydrophobically treated pigments are described in particular in patent application EP-A-1 086 683.

For the purposes of the present patent application, the term "nacre" is intended to mean coloured particles of any form, which may or may not be iridescent, in particular produced by certain molluscs in their shell, or alternatively synthesized, and which have a colour effect via optical interference.

Examples of nacres that may be mentioned include nacreous pigments such as titanium mica coated with an iron oxide, mica coated with bismuth oxychloride, titanium mica coated with chromium oxide, titanium mica coated with an organic dye in particular of the abovementioned type, and also nacreous pigments based on bismuth oxychloride. They may also be mica particles at the surface of which are superposed at least two successive layers of metal oxides and/or of organic colorants.

The nacres may more particularly have a yellow, pink, red, bronze, orangey, brown, gold and/or coppery colour or tint.

As illustrations of nacres that may be introduced as interference pigments into the first composition, mention may be made of the gold-coloured nacres sold in particular by the company Engelhard under the name Brilliant gold 212G (Timica), Gold 222C (Cloisonne), Sparkle gold (Timica), Gold 4504 (Chromalite) and Monarch gold 233X (Cloisoime); the bronze nacres sold in particular by the company Merck under the name Bronze fine (17384) (Colorona) and Bronze (17353) (Colorona) and by the company Engelhard under the name Super bronze (Cloisonne); the orange nacres sold in particular by the company Engelhard under the name Orange 363C (Cloisonne) and Orange MCR 101 (Cosmica) and by the company Merck under the name Passion orange (Colorona) and Matte orange (17449) (Microna); the brown nacres sold in particular by the company Engelhard under the name Nu-antique copper 340XB (Cloisonne) and Brown CL4509 (Chromalite); the nacres with a copper tint sold in particular by the company Engelhard under the name Copper 340A (Timica); the nacres with a red tint sold in particular by the company Merck under the name Sienna fine (17386) (Colorona); the nacres with a yellow tint sold in particular by the company Engelhard under the name Yellow (4502) (Chromalite); the red nacres with a gold tint sold in particular by the company Engelhard under the name Sunstone G012 (Gemtone); the pink nacres sold in particular by the company Engelhard under the name Tan opale G005 (Gemtone); the black nacres with a gold tint sold in particular by the company Engelhard under the name Nu antique bronze 240 AB (Timica), the blue nacres sold in particular by the company Merck under the name Matte blue (17433) (Microna), the white nacres with a silvery tint sold in particular by the company Merck under the name Xirona Silver, and the golden-green pink-orange nacres sold in particular by the company Merck under the name Indian summer (Xirona), and mixtures thereof.

Fillers

The composition according to the invention may optionally comprise at least one or more filler(s) of organic or mineral nature.

The term "filler" should be understood to mean colourless or white solid particles of any shape which are in a form that is insoluble and dispersed in the medium of the composition. These particles, of mineral or organic nature, can give body or rigidity to the composition and/or softness and uniformity to the makeup. They are different from colorants.

Among the fillers that may be used in the compositions according to the invention, mention may be made of silica, kaolin, bentone, starch, lauroyllysine, and fumed silica particles, optionally hydrophilically or hydrophobically treated, and mixtures thereof.

A composition used according to the invention may comprise one or more fillers in a content ranging from 0.1% to 15% by weight and in particular from 1% to 10% by weight relative to the total weight of the composition.

Additives

The composition according to the invention may furthermore comprise any of the ingredients conventionally used as additives in the cosmetics and dermatology field.

These additives are advantageously chosen from antioxidants, thickeners, sweeteners, basifying or acidifying agents and preserving agents, and mixtures thereof, and may be chosen advantageously from those proposed in Table 1 of the Codex Alimentarius.

As antioxidant, a composition in accordance with the invention may advantageously comprise at least one pentaerythrityl di-t-butyl hydroxycinnamate.

A composition according to the invention may also contain flavourings and/or fragrances.

As cosmetic active agents that may be used in the invention, mention may be made of sunscreens, vitamins A, E, C and B3, provitamins such as D-panthenol, calmatives such as α-bisabolol, Aloe vera, allantoin, plant extracts or essential oils, protective or restructuring agents, refreshing agents such as menthol and derivatives thereof, emollients, moisturizers, antiwrinkle active agents and essential fatty acids, and mixtures thereof.

The amounts of each of these various ingredients are those conventionally used in the fields under consideration, and range, for example, from 0.01% to 10% by weight relative to the total weight of the composition.

Water-Soluble Solvents

The composition may, where appropriate, comprise, besides water, at least one water-soluble solvent.

In the present invention, the term "water-soluble solvent" denotes a compound that is liquid at ambient temperature and water-miscible (miscibility with water of greater than 50% by weight at 25° C. and atmospheric pressure).

The water-soluble solvents that can be used may also be volatile.

Among the water-soluble solvents that may be used in the compositions in accordance with the invention, mention may be made in particular of monoalcohols containing from 1 to 5 carbon atoms, such as ethanol and isopropanol, glycols containing from 2 to 8 carbon atoms, such as ethylene glycol, propylene glycol, 1,3-butylene glycol and dipropylene glycol, $C_3$ and $C_4$ ketones and $C_2$-$C_4$ aldehydes.

When it (they) is (are) present, the content of water-soluble solvent(s) is at most 50% by weight relative to the weight of water, and preferably at most 30% by weight relative to the weight of water.

Needless to say, those skilled in the art will take care to select this or these optional additional compound(s), and/or the amount thereof, such that the advantageous properties of the composition according to the invention are not, or are not substantially, adversely affected by the envisaged addition.

The composition according to the invention may be manufactured via the known processes generally used in cosmetics or dermatology.

Application Device—Application Member

The compositions of the invention can in particular be applied to the area to be treated, for example the lips, by virtue of an application member which has a porous application surface. The application surface is suited to being impregnated with the composition according to the invention.

The application member may be entirely porous, i.e. the composition may cross from an internal surface of the application member to an external surface of the application member, or vice versa.

The application member may in particular consist of one or more open-cell or semi-open-cell foams.

Thus, the application member may be made up of at least two portions of foam, of different compressibilities, which can be adhesively bonded together.

The foam may be non-crosslinked or preferentially crosslinked.

Still preferentially, the foam(s) is (are) elastically compressible. The term "elastically compressible" is intended to mean that, starting from a position deformed by a pressure exerted on its surface, the foam returns to its initial shape when the pressure is released.

With such materials, the releasing of the composition on the surface to be treated takes place either by capillary action on contact with the lips, or by expulsion of the composition, from the pores of the applicator, in response to a slight deformation (by pressure) of said applicator on the surface to be treated.

The application member may have a cylindrical shape and may have a circular cross section. As a variant, the application member may have any other shape, for example conical, flattened-cone, nose-cone or prism shape, and can have an oval, rectangular or polygonal cross section. It may also comprise a bevelled portion and/or a concave portion forming a hollow on the application surface. The application member may be symmetrical or asymmetrical relative to a longitudinal plane of said application member.

The visible part of the application member may have a cross section which falls within a circle advantageously having a diameter of between 2 mm and 20 mm, and preferably between 5 30 mm and 15 mm. The visible part of the application member, in the non-compressed position, may be between 2 mm and 20 mm in height.

The application member may consist of several different materials, in particular of a stack of foams having different characteristics.

By way of example, the application member may consist of one or more foams chosen from polyether, polyester, polyurethane, polyester-polyurethane, NBR (natural butadiene rubber), SBR (synthetic butadiene rubber) or PVC (polyvinyl chloride) foams, or mixtures thereof, and quite particularly polyester-polyurethane, in particular the product S90 from Crest Foam Industries.

The density of the foam(s) forming the application member, measured according to standard ASTM D 3574-05, may advantageously be between 0.02 g·cm$^{-3}$ and 0.05 g·cm$^{-3}$, for example 0.03 g·cm$^{-3}$. This density makes it possible to release an appropriate amount of impregnated composition.

The average number of pores or cells of the foam(s) may advantageously be between 25 and 50 pores per centimetre, for example equal to 35 pores per centimetre. The average pore size may advantageously be between 0.2 mm and 0.5 mm. It should be noted that the evaluation of the average number of pores is conventionally carried out visually by counting. Preferably, the cells or pores communicate with one another omnidirectionally.

The hardness of the application surface of the applicator member, measured by means of an F-type durometer from Asker, may advantageously be between 10 Asker F and 70 Asker F.

At least one part of the surface of the application member may be covered with a flock, in particular based on polyamide, rayon, cotton, viscose or nylon fibres. The flock contributes to creating a store of product, immediately in the neighbourhood of the application surface. In addition, it makes it possible to impart more softness on application, in particular when the application member is made of wide-cell foam. Furthermore, the flock may contribute to the homogenization of the spreading of the composition to form a thin film.

The flock may consist of a mixture of fibres of various length and/or nature and/or diameter.

The length of the fibres may advantageously be between 0.2 mm and 1 mm, for example equal to 0.75 mm.

The fibre count grading unit may advantageously be between 0.3 dtex and 3.3 dtex, for example equal to 1.7 dtex.

As a variant, the application surface can be covered with a permeable coating of textile, perforated plastic or felt type.

In accordance with one advantageous variant of the invention, the device comprises a composition-dispensing mechanism which makes it possible to expel said composition from the container to the application member.

According to this variant, said dispensing mechanism advantageously comprises a composition-metering means.

Figure 2:
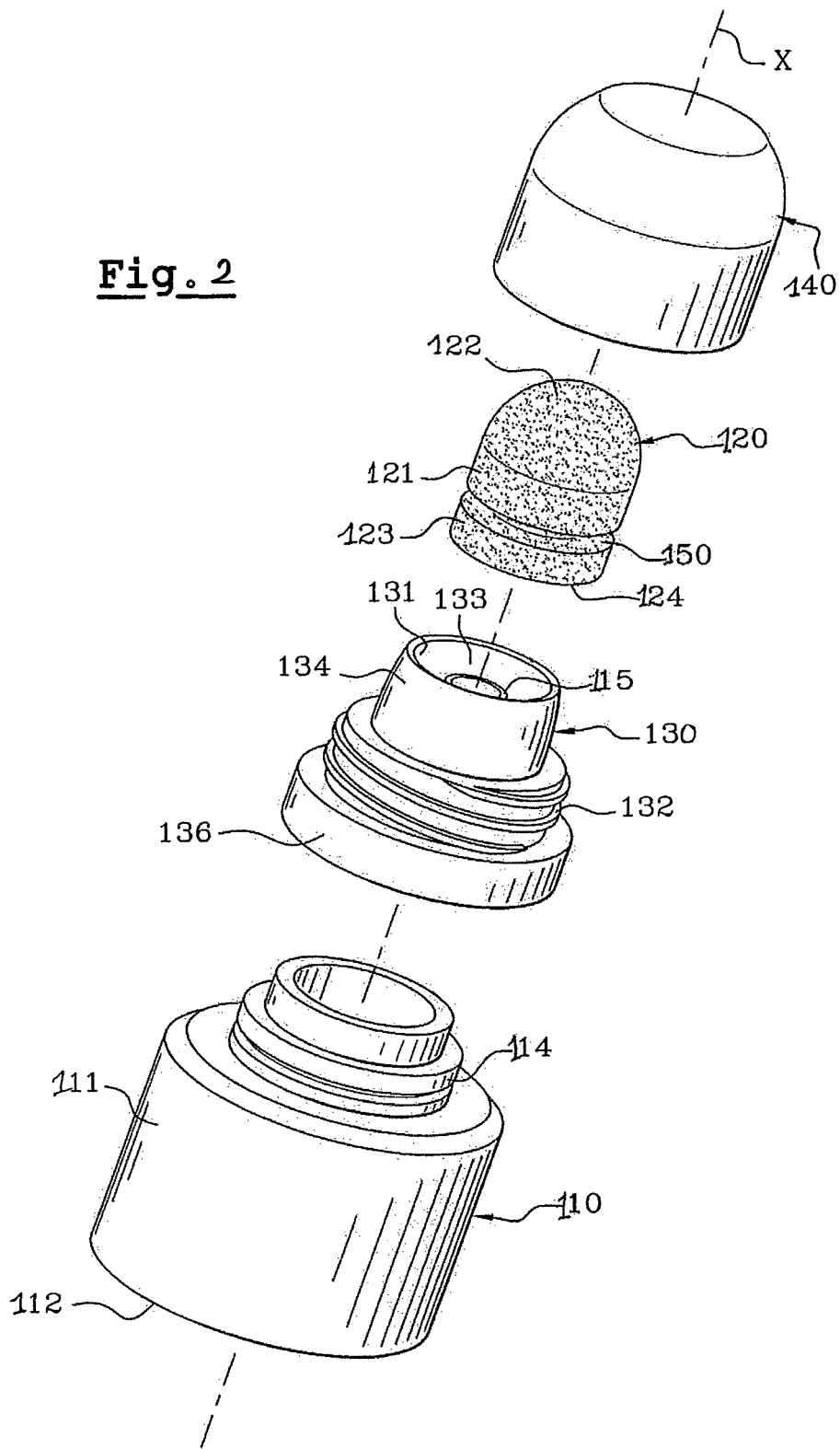
FIG. 2 is an exploded view of an application device according to a second embodiment.
Figure 3:
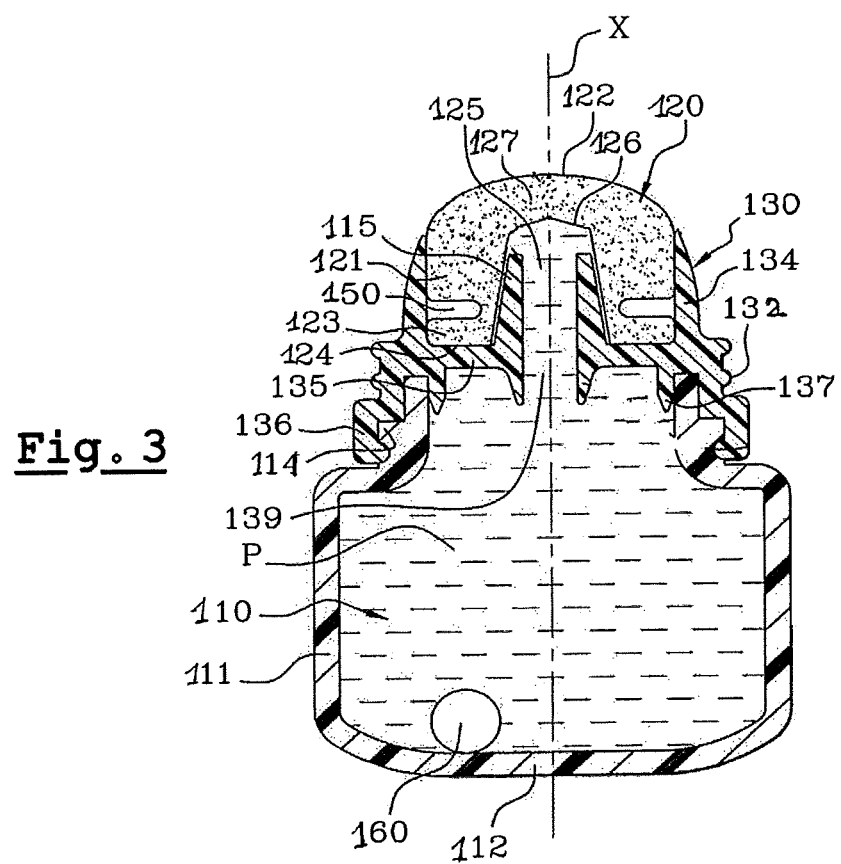
FIG. 3 is a sectional view of the device of FIG. 2.

Application devices that are particularly suited to this composition will be described with reference to the appended drawings, in which:

FIG. 1 is a sectional view of an application device according to a first embodiment;

FIG. 2 is an exploded view of an application device according to a second embodiment;

FIG. 3 is a sectional view of the device of FIG. 2.

According to a first embodiment represented in FIG. 1, the device 1 comprises a cylindrical polypropylene body 2 having a longitudinal axis X. The body 2 denotes a first housing 3 (container), delimited by a cylindrical skirt 19, a first end 18 of which is open, and a second end of which, opposite the first, is closed by a transverse wall 16 comprising passages which emerge to form a grille 42. The transverse wall 16 separates the first housing 3 from a second housing 6, located above the first housing 3.

The upper housing 6 has a bottom 7, in the shape of a hemisphere, into which the passages forming the grille 42 emerge. One end of the housing 6, opposite the bottom 7, forms a free edge 8 delimiting an opening 9. The external surface of the housing 6 comprises a screw thread 10 intended to cooperate with a corresponding screw thread 11 provided for on the internal surface of a skirt 12 of a stopper 13. As a variant, the stopper is reversibly snap-fastened onto the external surface of the housing 6.

The stopper 13 is rigidly connected to an applicator 14 correspondingly made to match the hemispherical profile defined by the bottom 7 of the housing 6. The application member 14 may be adhesively bonded, welded or crimped onto the cap 13.

The application member consists of an open-cell polyurethane foam. The density of the foam forming the application member, measured according to standard ASTM D 3574-05, is advantageously between 0.02 g·cm$^{-3}$ and 0.05 g·cm$^{-3}$, for example equal to 0.03 g·cm$^{-3}$.

According to one preferred variant, at least one part of the surface 14 of the application member is covered with a flock 15, in particular based on rayon, cotton, viscose or nylon fibres. The length of the fibres is advantageously between 0.2 mm and 1 mm, for example 0.75 mm. The fibre count grading unit is advantageously between 0.3 dtex and 3.3 dtex, for example equal to 1.7 dtex.

The application member 14 is proportioned relative to the housing 6 such that, when the stopper 13 is in the closed position, at least one portion of the application surface of the application member 14 is in contact with the bottom 7.

The application member 14 is proportioned such that, in this position, it is not appreciably axially compressed.

The composition of the invention is here referred to as product P. This product P is contained inside the housing 3 forming a container, the open end 18 of the housing 3 being closed via a dispensing mechanism 30. The latter is mounted by clip-fastening onto the body 2 of the housing 3, after filling with the product P inside the housing 3 through its open end 18. The mechanism 30 comprises an actuating wheel 31 mounted to rotate freely with respect to the body 2, via a bulge/groove arrangement. The wheel 31 is rigidly connected to a threaded rod 32 capable of axially driving a threaded piston 33, incapable of rotating inside the container, for example by virtue of a rib/notch assembly which prevents the piston from rotating inside the container. The mechanism may also comprise a metering means, such as a ratchet system, capable of periodically generating an audible sound, so as to inform the user of the amount of product dispensed.

As a variant, the mechanism associated with the first housing, for causing the product to exit, may be different; for example, the walls of the body 2 may be deformable in order to apply, by crimping, an overpressure in the container so as to expel the product through the grille.

To use this device, the user turns the actuating wheel through half or one turn, with the cap 13 in the closed position over the opening 9 of the housing 6, so as to cause a corresponding amount of product P to pass from the container to the applicator 14 contained in the housing 6, via the passage of the grille 42. The product is taken up by the applicator 14, in particular by capillary action. All that then remains is for the cap 13 to be unscrewed so that the application member can be extracted therefrom and for the product P to be applied by moving the application surface of the application member 14 over lips, in order to deposit the product impregnated in the application member.

According to a variant which is not illustrated, the application member 14 is axially oversized with respect to the housing 6. Thus, after having applied all the product contained on the application member 14, it is possible to reload the latter, without having to rescrew the cap fully onto the device 1, simply by introducing the application member 14 into the housing 6 through the opening 9, and picking up either residual product resulting from the previous actuating of the wheel 31, or product resulting from a further actuating of the wheel 31, in the absence of the application member 14.

According to a second embodiment represented in FIGS. 2 and 3, the device is in the form of an applicator bottle for a product P, and comprises mainly a container or reservoir 110 consisting of a body 111, one end of which is closed by a bottom 112. The other end of the reservoir 110 is surmounted by an application head which comprises an intermediate element 130 intended for mounting the head on the reservoir and an application member 120 housed in the intermediate element.

The intermediate element 130 comprises, on its external surface, means 132 (of screw thread or snap-fitting bead type) for enabling the removable mounting of a stopper 140 capable of covering the application member 120.

As a variant, a dispensing mechanism can be combined with the reservoir, for example a piston mechanism as previously described, or flexible walls making it possible to generate an overpressure in the reservoir in order to expel the product. Likewise, a ball 160 can be placed inside the reservoir so as to homogenize the product in order to facilitate the flow thereof and/or to facilitate the conveying thereof to the application member.

The internal wall of the intermediate element 130 defines a cylindrical internal housing 133 which rotates about an axis X. This housing 133 comprises a side wall 134 and a planar transverse wall 135 constituting the bottom of the housing. A fitting skirt 136 extends the side wall beyond the transverse wall, on the opposite side from the opening 131 of the intermediate element. The fitting skirt 136 is attached, by snap-fitting, onto the body of the reservoir, at the top of which a radial projection 114 is provided for, on the opposite side from the bottom 112.

This snap-fitting system can of course be replaced with any other system of attachment, in particular a screw attachment system. A scaling skirt 137 is advantageously provided for on the transverse wall 135 of the housing so as to come into leaktight contact with the inside of the reservoir.

The body 111 of the reservoir, the intermediate element 130 and also the stopper 140 are made of rigid material, for example of polyethylene. It is obvious that these three independent elements can each be made of a different material. It is thus possible to envisage using a flexible material for at least one part of the reservoir.

The housing 133 communicates with the inside of the reservoir via a passage 139 which passes through a shaft 115 extending along the axis of the housing. The shaft is made up of a single part with the transverse wall 135 from which it extends to a free end, located inside the housing 133. The shaft has a circular internal cross section, which is constant throughout its axial height, whereas its external cross section decreases to the free end.

The diameter of the shall is chosen according to the product contained in the reservoir, in such a way that the product coming from the reservoir can flow in the shaft, for example by simply shaking the assembly.

The application member 120 is mounted inside the housing 133 around the shaft 115.

The application member is in the form of a block of porous material(s), at least one part of which is elastically compressible.

According to one preferred embodiment, the application member is made up of a block of open-cell foam, in particular a block of polyurethane foam. Alternatively, the application member 120 may be made up of an axial succession of at least two portions of foam, of different compressibilities, which can be adhesively bonded together.

According to the example represented, the application member has a cylindrical shape and has a circular cross section. It is obvious that the application member can have any other shape, and can have any other cross section.

The application member 120 has a side wall 121, one end 122 of which constitutes a dome-shaped application surface.

Where appropriate, the application surface 122 can be covered with a flock. In this case, the flock can consist of hairs of various diameters and/or of various natures and/or of various heights, or of a mixture of such hairs.

On the opposite side from this application surface 122, the application member ends with a second open end 124 which comes into contact with the transverse wall 135 of the housing. The end 124 can be permanently attached to the intermediate element 130. Advantageously, this end is removably attached so as to make it possible to easily remove the application member in order, for example, to clean it. To this effect, the end 124 of the application member is covered with a permanent adhesive, for example an acrylic adhesive, which adheres more to the application member than to the wall 135.

A portion 123 of the side wall located on the side of the open end 124 acts as a support for the application member. The portion 123 acting as a support for the application member is separated from the rest of the application member by an annular groove 150 which defines a zone of smaller cross section. The annular groove 150 provided for on the periphery of the application member enables the zone of smaller cross section to have a greater compressibility than the rest of the application member. Thus, when a pressure is exerted on the application surface, the maximum compression of the zone of smaller cross section is obtained before obtaining the maximum compression of the application member.

When the application member is mounted in the housing 133, it occupies approximately the entire housing, the application member having a shape approximately complementary to the shape of the housing. The application member 120 has in particular an axial recess 125, the shape of which is adjusted so that the application member comes to press against the wall of the shaft, without being substantially laterally compressed by said shaft. Alternatively, the side wall of the application member can be at a distance from the shaft. When the application member is in the relaxed position, the axial recess 125 has an axial height which is substantially greater than the axial height of the shaft 115 so as to define an internal cavity inside the application member, between an internal surface 126 located facing the shaft and the free end of the shaft. The portion 127 of the application member located above the cavity has an axial thickness which is smaller than the thickness of the lateral edge 121 of the application member, measured perpendicular to the axis X. The cavity can thus constitute a store of product in proximity to the application surface, it being possible for the product to come into contact with the application member only in the cavity.

Typically, the application member has a diameter of between 2 mm and 20 mm, and preferably between 5 mm and 15 mm. Its height, in the non-compressed position, can range between 2 mm and 20 mm.

Generally, the application member 120 comprises pores or open cells which have an average size of between 0.3 mm and 0.5 mm. Preferably, the pores or cells communicate with one another omnidirectionally.

In order to use the application assembly according to the invention, the user shakes the packaging and application assembly in order to bring the product into the shaft and into the application member. As a variant, the user actuates a dispensing mechanism in order to bring the product to the application member. Product is then kept inside the block of foam 120 of the application member by capillary action. All that is then needed is to bring the application member 120 into contact with the area to be treated; a slight pressure can be applied so as to place the product present in the cells of the foam in proximity to the application surface 122. Product is then spread by passing the application surface 122 over the support to be treated, by simple capillary contact, so as to draw the product in the form of a film, under the action of the affinity of the product that is exerted between the application surface and the support to be treated, without the slightest pressure being appreciably exerted on the application assembly.

In the detailed description above, reference was made to preferred embodiments of the invention. It is obvious that variants can be introduced therein without departing from the spirit of the invention as claimed hereinafter.

In particular, the shape of the applicator may be different from the shape illustrated with reference to the embodiments that have just been described. Generally, the shape of the applicator is chosen according to the area to be treated. For example, in the case of an applicator for the lips, an applicator approximately in the shape of a cone, a nose-cone or a hemisphere will more particularly be used, the applicator optionally comprising a bevelled face.

Likewise, the applicator can be dissociated from a container containing the product without a dispensing mechanism. The device is then used by dipping the applicator in the container and then by applying the product to the lips by means of the applicator.

The example hereinafter is given as a non-limiting illustration of the field of the invention.

EXAMPLES

Example 1

1. Composition

The composition of which the ingredients are collated in the table below is prepared; the amounts are expressed in weight amount of starting material.

| Phase | Chemical name | Amount (%) |
|---|---|---|
| A | Oxyethylenated polydimethylsiloxane | 2 |
| A | Oxyethylenated polymethylcetyldimethylmethylsiloxane | 1 |
| A | Cyclohexadimethylsiloxane | 8.8 |
| A | Polyphenyltrimethylsiloxydimethylsiloxane | 14 |

-continued

| Phase | Chemical name | Amount (%) |
|---|---|---|
| A | Butyl acrylate copolymer containing dendritic silicone side chains: [tri(trimethylsiloxy)siloxyethyldimethylsiloxy]silylpropyl methacrylate in isododecane: 40/60 | 10 |
| B | Rutile titanium oxide treated with alumina/silica/trimethylolpropane | 1.82 |
| B | Calcium salt of lithol B red | 1.51 |
| B | Phloxin B disodium salt aluminium lake on alumina, aluminium benzoate | 1.26 |
| B | Brilliant yellow FCF aluminium lake on alumina | 2.05 |
| B | Black iron oxide | 1.36 |
| B | Cyclohexadimethylsiloxane | 10 |
| C | Water | 34.5 |
| C | 1,3-Butylene glycol | 6 |
| C | Magnesium sulfate•7 $H_2O$ | 0.7 |
| C | Non-denatured 96-degree ethyl alcohol | 5 |

2. Preparation Firstly, the ingredients of phase B were mixed together and the whole mixture was milled in an Exakt three-roll machine.

Secondly, phase A was mixed with stirring using a Moritz mixer for 10 minutes.

At the end of this operation, phase B prepared beforehand was added and the stirring was maintained for a further 20 minutes.

Moreover, aqueous phase C was prepared with magnetic stirring, and was subsequently added, to phase A, with stirring using a Moritz mixer, maintained until a smooth and homogeneous mixture was obtained.

These various steps were carried out at ambient temperature.

The viscosity of the composition, measured in accordance with the protocol explained in detail in the description, is 0.15 Pa·s.

The composition was then introduced into a device similar to FIGS. 2 and 3, the application member of which consists of the S90NR foam from the company Crest Foam Industries, covered with a flock from the company ERZI Flock Technik (0.75 mm; 1.7 dtex). The device makes it possible to apply a film to the lips, measured wet (therefore before drying), of 11.63±1.02 μm.

The composition applied does not migrate after one hour and the film wear is satisfactory.

Protocol for Measuring the Film Thickness:

This protocol is an in vitro measurement.

A square of Bioskin® synthetic skin of 3 cm/4 cm is prepared.

The skin square obtained is weighed.

The composition is applied by means of the device so as to obtain an even deposit covering the entire surface of the skin square.

The skin square thus made-up is weighed.

Thickness of the Film:

Thickness (cm)=volume of composition applied (g): density of the composition (g/cm³).

The density of the composition is 1.

The average thickness is given with three separate measurements.

Example 2

1. Composition

The composition of which the ingredients are collated in the table below is prepared; the amounts are expressed in weight amount of starting material.

| Phase | Chemical Name | Amount (%) |
|---|---|---|
| A | PEG-10 dimethicone | 2 |
| | Cetyl PEG/PPG-10/1 dimethicone | 1 |
| | Hydrogenated polyisobutene (Parleam ®) | 14 |
| | Acrylic acid/isobutyl acrylate/isobornyl acrylate copolymer (50/50 in isododecane) | 16 |
| | Isododecane | 2.8 |
| B | Titanium dioxide | 1.82 |
| | Red 7 | 1.51 |
| | Red 28 lake | 1.26 |
| | Yellow 6 lake | 2.05 |
| | Iron oxides | 1.36 |
| | Isododecane | 10 |
| C | Water | 34.5 |
| | Butylene glycol | 6 |
| | Magnesium sulfate | 0.7 |
| | Alcohol | 5 |

2. Preparation

Firstly, the ingredients of phase B were mixed together and the whole mixture was milled in an Exakt three-roll machine.

Secondly, phase A was mixed with stirring using a Moritz mixer for 20 minutes.

At the end of this operation, phase B prepared beforehand was added and the stirring was maintained for a further 15 minutes.

Moreover, aqueous phase C was prepared with magnetic stirring, and was subsequently added, to phase A, with stirring using a Moritz mixer, maintained until a smooth and homogeneous mixture was obtained (approximately 15 minutes).

These various steps were carried out at ambient temperature.

The resulting composition was very fluid and homogeneous. The viscosity of the composition, measured in accordance with the protocol explained in detail in the description, was 0.13 Pa.s.

The composition was then introduced into a device similar to FIGS. 2 and 3, the application member of which consists of the S90NR foam from the company Crest Foam Industries, covered with a flock from the company ERZI Flock Technik (0.75 mm; 1.7 dtex).

The device makes it possible to apply a film to the lips, measured wet (therefore before drying), of 8.75±2.59 µm.

The composition was very easily applied. The film was matt/satin, comfortable, with a good film wear, and did not migrate after one hour.

The composition was also introduced into a device similar to FIG. 1, the application member of which consists of the S90NR foam from the company Crest Foam Industries, covered with a flock from the company ERZI Flock Technik (0.75 mm; 1.7 dtex).

The device makes it possible to apply a film to the lips, measured wet (therefore before drying), of 5.55±0.48 µm.

The composition was very easily applied. The film was matt/satin, comfortable, with a good film wear, and no migration.

Example 3

1, Composition

The composition of which the ingredients are collated in the table below is prepared; the amounts are expressed in weight amount of starting material.

| Phase | nom chimique | Quantité (%) |
|---|---|---|
| A | PEG-10 dimethicone | 2 |
| A | Cetyl PEG/PPG-10/1 dimethicone | 1 |
| A | Cyclohexadimethylsiloxane | 8.8 |
| A | Trimethylsiloxyphenyl Dimethicone | 14 |
| A | Butyl acrylate copolymer containing dendritic silicone side chains: [tri(trimethylsiloxy)siloxyethyldimethylsiloxy]silylpropyl methacrylate in isododecane: 40/60 | 10 |
| B | Rutile titanium oxide treated with alumina/silica/trimethylolpropane | 1.82 |
| B | Calcium salt of lithol B red | 1.51 |
| B | Phloxin B disodium salt aluminium lake on alumina, aluminium benzoate | 1.26 |
| B | Brilliant yellow FCF aluminium lake on alumina | 2.05 |
| B | Black iron oxide | 1.36 |
| B | Cyclohexadimethylsiloxane | 10 |
| C | Water | 34.5 |
| C | 1,3-Butylene glycol | 6 |
| C | Magnesium sulfate•7 $H_2O$ | 0.7 |
| C | Ethyl alcohol | 5 |

The preparation was the same as the one described in example 1.

The composition was then introduced into a device similar to FIG. 1, the application member of which consists of the S90NR foam from the company Crest Foam Industries, covered with a flock from the company ERZI Flock Technik (0.75 mm; 1.7 dtex).

The applied film, measured wet (therefore before drying), was of 3.06±0.96 µm.

The composition was very easily applied. The film was matt/satin, comfortable, with a good film wear, and no migration.

As a comparison, the composition was also applied by using an applicator for gloss lip compositions (FLEXIBLE APPLICATORS FLOCKED: Complete lip gloss package using applicator 14030; GEKA GMBH).

The applied film, measured wet (therefore before drying), was of 16.11±2.55 µm and was more perceptible on the lip than the film applied according to the invention.

The invention claimed is:

1. An application device, comprising:
   a container;
   a composition for making up and/or caring for the lips (F), stored in the container, which is in the form of a liquid emulsion comprising:
   a) at least 8% by weight, relative to the total weight of the composition, of one or more non-volatile oils;
   b) at least one film-forming agent selected from the group consisting of alkylcellulose, silicone resin, and a vinyl polymer comprising a carbosiloxane dendrimer-based unit;
   c) at least 10% by weight of water relative to the total weight of the composition; and
   an application member that is suitable for applying the composition which has a porous application surface with one or more open-cell or semi-open cell foams, wherein the composition has a viscosity at 25° C. of between 0.005 and 15 Pa.s,
   and wherein the density of the foam(s) forming the application member, measured according to standard ASTM D 3574-05, is between 0.02 g.cm$^{-3}$ and 0.05 g.cm$^{-3}$.

2. The device of claim 1, wherein the non-volatile oil comprises at least one oil selected from the group consisting of non-volatile silicone oils, which may or may not be phenylated, non-volatile fluoro oils, polar and non-polar non-volatile hydrocarbon-based oils.

3. The device of claim 1, wherein a content of the non-volatile oil is between 10% and 30% by weight relative to the weight of the composition.

4. The device of claim 1, wherein the composition comprises the vinyl polymer containing at least one carbosiloxane dendrimer-based unit and having a molecular side chain containing a carbosiloxane dendrimer structure, and is the product of polymerization of:
(A) from 0 to 99.9 parts by weight of a vinyl monomer; and
(B) from 100 to 0.1 parts by weight of a carbosiloxane dendrimer of formula (I) below:

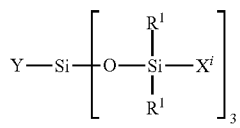
(I)

in which:
$R^1$ represents an aryl group containing from 5 to 10 carbon atoms or an alkyl group containing from 1 to 10 carbon atoms;
$X^i$ represents a silylalkyl group which, when i=1, is represented by formula (II):

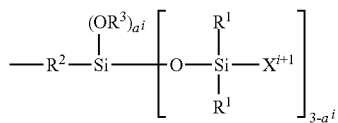
(II)

in which:
$R^1$ is as defined above in formula (I),
$R^2$ represents an alkylene radical containing from 2 to 10 carbon atoms,
$R^3$ represents an alkyl group containing from 1 to 10 carbon atoms,
$X^{i+i}$ is chosen from: a hydrogen atom, an alkyl group containing from 1 to 10 carbon atoms, an aryl group containing from 5 to 10 carbon atoms and a silylalkyl group defined above of formula (II) with i = i +1,
i is an integer from 1 to 10 which represents the generation of said silylalkyl group, and
$a^i$ is an integer from 0 to 3;
Y represents a radical-polymerizable organic group chosen from:

organic groups containing a methacrylic group or an acrylic group, said organic groups being represented by the formulae:

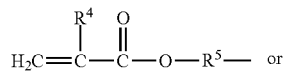 or

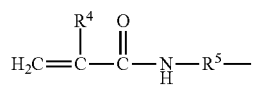

in which:
$R^4$ represents a hydrogen atom or an alkyl group containing from 1 to 10 carbon atoms; and
$R^5$ represents an alkylene group containing from 1 to 10 carbon atoms; and
organic groups containing a styryl group of formula:

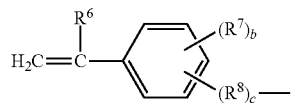

in which:
$R^6$ represents a hydrogen atom or an alkyl group containing from 1 to 10 carbon atoms;
$R^7$ represents an alkyl group containing from 1 to 10 carbon atoms;
$R^8$ represents an alkylene group containing from 1 to 10 carbon atoms;
b is an integer from 0 to 4; and
c is 0 or 1, such that, if c is 0, $-(R^8)_c-$ represents a bond.

5. The device of claim 4, wherein the carbosiloxane dendrimer is represented by the following formula:

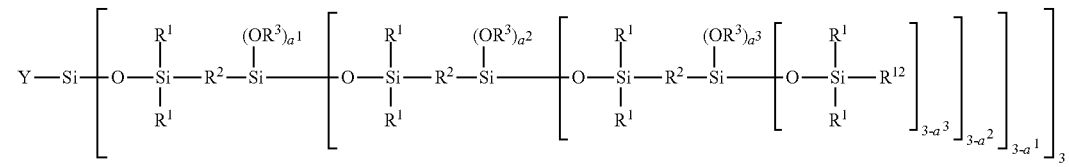

in which:
Y, $R^1$, $R^2$ and $R^3$ are as defined in claim 4;
$a^1$, $a^2$ and $a^3$ correspond to the definition of $a^i$ according to claim 4; and
$R^{12}$ is H, an aryl group containing from 5 to 10 carbon atoms or an alkyl group containing from 1 to 10 carbon atoms.

6. The device of claim 4, wherein the carbosiloxane dendrimer is represented by one of the following formulae:

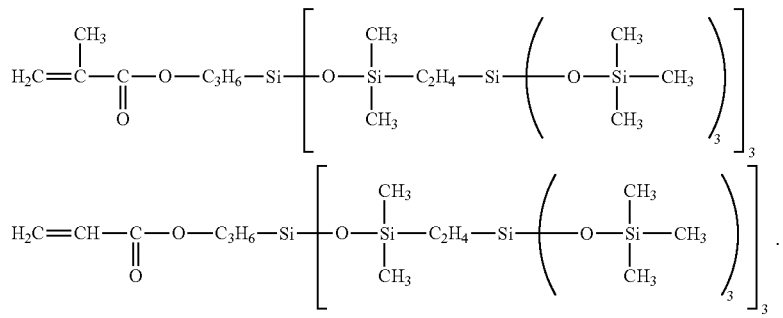

7. The device of claim 1, wherein the content of film-forming agent(s) represents from 1% to 20% by weight, relative to the total weight of the composition.

8. The device of claim 1, wherein the composition further comprises at least one volatile oil.

9. The device of claim 8, wherein the content of volatile oil(s) represents from 0.1% to 30% by weight relative to the total weight of the composition.

10. The device of claim 1, wherein the composition further comprises at least one surfactant.

11. The device of claim 10, wherein the content of surfactant(s) represents from 0.05% to 20% by weight relative to the total weight of the composition.

12. The device of claim 1, wherein the composition further comprises at least one colorant.

13. The device of claim 1, wherein the water content represents from 20% to 60% by weight relative to the total weight of the composition.

14. The device of claim 1, wherein the composition is in the form of an inverse (water-in-oil) emulsion.

15. The device of claim 1, wherein the application member consists of one or more foams chosen from polyether, polyester, polyurethane, polyester-polyurethane, NBR (natural butadiene rubber), SBR (synthetic butadiene rubber) or PVC (polyvinyl chloride) foams, or mixtures thereof.

16. The device of claim 1, wherein the average number of pores of the foam(s) is between 25 and 50 pores per centimetre.

17. The device of claim 1, wherein at least one part of the surface of the application member is covered with a flock.

18. The device of claim 17, wherein at least one part of the surface of the application member is covered with fibres having a length between 0.2 mm and 1 mm, and the fibre count grading unit between 0.3 dtex and 3.3 dtex.

19. The device of claim 1, further comprising a composition-dispensing mechanism which makes it possible to expel said composition from the container to the application member.

20. The device of claim 19, wherein the dispensing mechanism comprises a meter adapted to meter the composition.

21. A process for making up and/or caring for the lips, the process comprising applying the composition stored in a container with the application member of the device of claim 1 to the lips.

22. The process of claim 21, wherein the deposit of composition, measured before drying, ranges between 5 and 30 µm.

* * * * *

UNITED STATES PATENT AND TRADEMARK OFFICE
CERTIFICATE OF CORRECTION

PATENT NO. : 10,871,252 B2  
APPLICATION NO. : 15/872347  
DATED : December 22, 2020  
INVENTOR(S) : Lahousse et al.

It is certified that error appears in the above-identified patent and that said Letters Patent is hereby corrected as shown below:

In the Claims

In Column 74, Claim 1, Line 46, delete "(F)," and insert -- (P), --.

Signed and Sealed this
Twelfth Day of October, 2021

Drew Hirshfeld
*Performing the Functions and Duties of the*
*Under Secretary of Commerce for Intellectual Property and*
*Director of the United States Patent and Trademark Office*

UNITED STATES PATENT AND TRADEMARK OFFICE
CERTIFICATE OF CORRECTION

PATENT NO. : 10,871,252 B2  Page 1 of 1
APPLICATION NO. : 15/872347
DATED : December 22, 2020
INVENTOR(S) : Lahousse et al.

It is certified that error appears in the above-identified patent and that said Letters Patent is hereby corrected as shown below:

In the Claims

In Column 74, Claim 1, Line 46, delete "(F)," and insert -- (P), --.

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*